(12) United States Patent
Georgiev et al.

(10) Patent No.: US 6,759,211 B1
(45) Date of Patent: Jul. 6, 2004

(54) TUMOR GROWTH INHIBITION- AND APOPTOSIS-ASSOCIATED GENES AND POLYPEPTIDES AND METHODS OF USE THEREOF

(75) Inventors: Georgii Georgiev, Moscow (RU); Sergei Kiselev, Moscow (RU); Egor Prokhorchouk, Moscow (RU); Elinborg Ostermann, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 09/462,625

(22) PCT Filed: Jul. 10, 1998

(86) PCT No.: PCT/EP98/04287

§ 371 (c)(1),
(2), (4) Date: Jul. 28, 2000

(87) PCT Pub. No.: WO99/02686

PCT Pub. Date: Jan. 21, 1999

Related U.S. Application Data

(63) Continuation-in-part of application No. 08/893,764, filed on Jul. 11, 1997, now Pat. No. 6,172,211.

(51) Int. Cl.[7] .................................................. C12P 21/06
(52) U.S. Cl. ..................... 435/69.1; 536/23.5; 536/24.3; 530/350; 435/320.1; 435/325
(58) Field of Search .............................. 435/69.1, 320.1, 435/325, 70.1; 536/23.5, 24.3; 530/350

(56) References Cited

U.S. PATENT DOCUMENTS

| | | | |
|---|---|---|---|
| 5,521,291 A | 5/1996 | Curiel et al. | 530/391.7 |
| 5,547,932 A | 8/1996 | Curiel et al. | 435/65 |
| 5,578,461 A | 11/1996 | Sherwin et al. | 435/69.1 |
| 6,172,211 B1 | 1/2001 | Georgiev et al. | 536/23.5 |

FOREIGN PATENT DOCUMENTS

| | | |
|---|---|---|
| EP | 0 394 827 A1 | 10/1990 |
| WO | WO 90/14092 | 11/1990 |
| WO | WO 93/09222 | 5/1993 |
| WO | WO 94/12650 | 6/1994 |
| WO | WO 97/18454 | 5/1997 |
| WO | WO 97/29765 | 8/1997 |
| WO | WO 9729765 A1 * | 8/1997 |

OTHER PUBLICATIONS

Korobko, EV, et al, Jun. 1998, [Secretion of the cytotoxic protein Tag7 in response to treatment of cells with lipopolysaccharide] [Article in Russian], Dokl. Akad. Nau., vol. 360, No. 6, pp. 838–840.*

Prokhorchuk, EB, et al, Jun. 1998, [Genome organization and chromosome localization of a novel ligand of the tumor necrosis factor family][Article in Russian], Dokl.Akad. Nauk., vol. 360, No. 5, pp. 699–701.*

Bonaldo, MF, et al, Genome Res. 6 (9), 791–806 (1996), Database GenBank, Accession No. BE654595, Ul–M–AJ1–agz–e–04–0–Ul.r1 NIH_BMAP_MOB_N Mus musculus cDNA clone.*

Selsted, ME, WO9729765–A1 (Aug. 21, 1997), Database Geneseq, Accession No. AAW23723, Murine granulocyte peptide A precursor (antimicrobial MGP–A) (see USPTO Search Report US–09–462–625–1.mg, result No. 2).*

Prokhortchouk, EB, Direct Submision (Apr. 01, 1997), Database GenBank, Accession No. Y12088, *Mus. musculus* tag7 gene, exon 1.*

NCI–CGAP, Unpublished (1997), Database GenBank, Accession No. AI507116, vj82f09.x1 Soares_mammary_gland_NbMMG *Mus musculus* cDNA clone IMAGE:935561 3' similar to gb:X86374 *M. musculus* mRNA for TAG7 protein (MOUSE).*

Schibler, KR, et al, Nov. 1997, Isolation and characterization of a novel gene up–regulated by granulocyte colony stimulating factor in a murine progenitor cell line, Blood, vol. 90, No. 10 SUPPL. 1 Part 2, pp. 152B (meeting abstract).*

Kustikova, OS, et al, 1996, Cloning of the tag7 gene expressed in metastatic mouse tumors, Russ. J. Genet. (Translation of Genetika (Moscow)), vol. 32, No. 5, pp. 540–546.*

Marra, M, et al, Unpublished (1996), Database GenBank, Accession No. AA015317, mh22a05.r1 Soares mouse placenta 4NbMP13.5 14.5 *Mus. musculus* cDNA clone IMAGE:443216 5' similar to gb:X86374 *M. musculus* mRNA for TAG7 protein.*

De Tullio, R, Direct Submission (May 19, 1997), Database GenBank, Accession No. Y13591, *Rattus norvegicus* mRNA for calpastatin, clone RNCAST23.*

(List continued on next page.)

*Primary Examiner*—Yvonne Eyler
*Assistant Examiner*—Stephen L. Rawlings
(74) *Attorney, Agent, or Firm*—Sterne, Kessler, Goldstein & Fox P.L.L.C.

(57) ABSTRACT

The present invention is generally directed to the identification of mouse and human genes that inhibit the growth of a tumor and induce apoptosis in cancer cells, and to polypeptides encoded by such genes. In particular, the invention concerns the nucleotide sequence of one such tumor-inhibiting gene, tag7, and the amino acid sequence of a polypeptide encoded by tag7. The invention also provides isolated nucleic acid molecules comprising tag7 polynucleotides, and vectors and host cells comprising these isolated nucleic acid molecules. The invention also provides methods of producing tag7 polynucleotides using these nucleic acid molecules, vectors and host cells, tag7 polypeptides made by three methods and antibodies that specifically bind to the tag7 polypeptide. The invention also concerns methods of inhibiting tumor growth and inducing tumor cell apoptosis, and methods of cancer therapy, using the present tag7 nucleic acid molecules and polypeptides.

39 Claims, 26 Drawing Sheets

OTHER PUBLICATIONS

Marra, M, et al, Unpublished (1996), Database GenBank, Accession No. AA238752, my35e09.r1 Barstead mouse pooled organs MPLRB4 *Mus. musculus* cDNA clone IMAGE:697855 5' similar to gb:X86374 *M. musculus* mRNA for TAG7 protein.*

Kang, D, et al, Direct Submission (Jul. 08, 1998), Database GenBank, Accession No. AF076482, *Mus. musculus* peptidoglycan recognition protein precursor (Pgrp) mRNA, complete cds.*

Kustikova, O, et al, Clonine and preliminary characterization of new gene tag7, Pharmacology & Toxicology, vol. 77, No. SUPPL. 2, pp. 38 (meeting abstract).*

Marra, M, et al, Unpublished (1996), Database GenBank, Accession No. AA238564, my35f04.r1 Barstead mouse pooled organs MPLRB4 *Mus. cusculus* cDNA clone IMAGE:697855 5' similar to gb:X86374 *M. musculus* mRNA for TAG7 protein.*

Aggarwal, B.B. et al., "Primary Structure of Human Lymphotoxin Derived from 1788 Lymphoblastoid Cell Line," *J. Biol. Chem.* 260:2334–2344 (1985).

Armentano, D. et al., "Expression of human factor IX in rabbit hepatocytes by retrovirus–mediated gene transfer: Potential for gene therapy of hemophilia," *Proc. Natl. Acad. Sci. USA* 87:6141–6145 (1990).

Armitage, R.J., "Tumor necrosis factor receptor superfamily members and their ligands," *Curr. Opin. Immunol.* 6:407–413 (1994).

Armitage, R.J. et al., "Identification of a source of biologically active CD40 ligand," *Eur. J. Immunol.* 22:2071–2076 (1992).

Axelrod, J.H. et al., "Phenotypic correction of factor IX deficiency in skin fibroblasts of hemophilic dogs," *Proc. Natl. Acad. Sci. USA* 87:5173–5177 (1990).

Barnett, S.C. and Eccles, S.A., "Studies of mammary carcinoma metastasis in a mouse model system. I: Derivation and characterization of cells with different metastatic properties during tumour progression in vivo," *Clin. Expl. Metast.* 2:15–36 (1984).

Basset, P. et al., "A novel metalloproteinase gene specifically expresed in stromal cells of breast carcinomas," *Nature* 348:699–704 (1990).

Bernhard, E.J. et al., "Direct evidence linking expression of matrix metalloproteinase 9 (92–kDa gelatinase/collagenase) to the metastatic phenotype in transformed rat embryo cells," *Proc. Natl Acad. Sci. USA* 91:4293–4297 (1994).

Blankenstein, T. et al., "Tumor Suppression after Tumor Cell–targeted Tumor Necrosis Factor αGene Transfer," *J. Exp. Med.* 173:1047–1052 (1991).

Bontempo, F.A. et al., "Liver Transplantation in Hemophilia A," *Blood* 69(6):1721–1724 (1987).

Browning, J. and Ribolini, A., "Studies on the Different Effects of Tumor Necrosis Factor and Lymphotoxin on the Growth of Several Human Tumor Lines," *J. Immunol.* 143:1859–1867 (1989).

Browning, J.L. et al., "Lymphotoxin β, a Novel Member of the TNF Family That Forms a Heteromeric Complex with Lymphotoxin in the Cell Surface," *Cell* 72:847–856 (1993).

Cohen, J.J. and Duke, R.C., "Apoptosis and Programmed Cell Death in Immunity," *Annu. Rev. Immunol.* 10:267–293 (1992).

de Kossodo, S. et al., "Tumor Necrosis Factor α Is Involved in Mouse Growth and Lymphoid Tissue Development," *J. Exp. Med.* 176:1259–1264 (1992).

Drumm, M.L. et al., "Correction of the Cystic Fibrosis Defect In Vitro by Retrovirus–Mediated Gene Transfer," *Cell* 62:1227–1233 (1990).

Ebralidze, A.K. et al, "Isolation of cDNA Clones which are Specifically Transcribed in Metastatic Tumor Cells," *Genetika (USSR)* 25:932–936 (1989).

Fidler, I.J. and Hart, I.R., "Biological Diversity in Metastatic Neoplasms: Origins and Implications," *Science* 217:998–1003 (1982).

Fink, J.K. et al., "Correction of glucocerebrosidase deficiency after retroviral–mediated gene transfer into hematopoietic progenitor cells from patients with Gaucher disease," *Proc. Natl. Acad. Sci.* 87:2334–2338 (1990).

Gardner, R.L., "Mouse chimaeras obtained by the injection of cells into the blastocyst," *Nature* 220:596–597 (1968).

Golstein, P. et al., "Cell Death Mechanisms and the Immune System," in *Immunol. Rev.* 121:29–65 (1991).

Hagen, T.J. et al., NCBI Entrez, GenBank Report, Accession No. M29288, (Feb. 1994).

Hagen, T.J. and Shimkets, I.J., "Nucleotide sequence and transcriptional products of the csg locus of *Myxococcus xanthus*," *J. Bacteriol.* 172:15–23 (1990).

Harrington, E.A. et al., "c–Myc–induced apoptosis in fibroblasts in inhibited by specific cytokines," *EMBO J.* 13(14):3286–3295 (1994).

Hock, H. et al., "Mechanisms of rejection induced by tumor cell–targeted gene transfer of interleukin 2, interleukin 4, interleukin 7, tumor necrosis factor, or interferon γ," *Proc. Natl. Acad. Sci. USA* 90:2774–2778 (1993).

Ishibashi, K. et al., "Tumor Necrosis Factor–β in the Serum of Adult T–Cell Leukemia With Hypercalcemia," *Blood* 77(11):2451–2455 (1991).

Kang, D. et al., "A peptidoglycan recognition protein in innate immunity conserved from insects to humans," *Proc. Natl. Acad. Sci. USA* 95:10078–10082 (Aug. 1998).

Kerbell, R.S., "Growth dominance of the metastatic cancer cell: cellular and molecular aspects," *Advances in Cancer Research* 55:87–131 (1990).

Keski–Oja, J. and Moses, H.L., "Growth Inhibitory Polypeptides in the Regulation of Cell Proliferation," *Med. Biol.* 65:13–20 (1987).

Kiselev, S.L. et al., "Molecular cloning and characterization of the mouse tag7 gene encoding a novel cytosine," *J. Biol. Chem.* 273:18633–18639 (Jul. 1998).

Kono, D.H. et al., "Lupus susceptibility loci in New Zealand mice," *Proc. Natl. Acad. Sci. USA* 91:10168–10172 (1994).

Kustikova, O. et al., "Cloning and preliminary characterization of new gene tag7," *Pharm. Toxicol.* 77(Suppl. II):38 (1995).

Kustikova, O. et al., "Cloning of the tag7 Gene Expressed in Metastatic Mouse Tumors," *Genetika (USSR)* 32:621–628 (May 1996).

Kustikova, O. et al., NCBI Entrez Nucleotide, Genbank Report, Accession No. X86374 (Jul. 1998).

Larrick, J.W. and Wright, S.C., "Cytotoxic mechanism of tumor necrosis factor–α," *FASEB J.* 4:3215–3223 (1990).

Law, P.K. et al., "Dystrophin production induced by myoblast transfer therapy in Duchenne muscular dystrophy," *Lancet* 336:114–115 (1990).

Liang, P. and Pardee, A.B., "Differential display of eukaryotic messenger RNA by means of the polymerase chain reaction," *Science* 257:967–971 (1992).

Liotta, L.A. et al., "Tumor Invasion and the Extracellular Matrix," *Lab. Invest.* 49:636–649 (1983).

Marra, M. et al., NCBI Entrez–Nucleotide, GenBank Report, Accession No. AA238564 (Mar. 1997).

Morel, L. et al., "Polygenic Control of Susceptibility to Murine Systemic Lupus Erythematosus," *Immunity* 1:219–229 (1994).

Morgan, J.E. et al., "Normal Myogenic Cells from Newborn Mice Restore Normal Histology to Degenerating Muscles of the mdx Mouse," *J. Cell Biol.* 111:2437–2449 (1990).

Nedospasov, S.A. et al., "The genes for tumor necrosis factor (TNF–alpha) and lymphotoxin (TNF–beta) are tandemly arranged on chromosome 17 of the mouse," *Nucl. Acids Res.* 14:7713–7725 (1986).

Ohta, M. et al., "Two forms of transforming growth factor–β distinguished by multipotential haematopoietic progenitor cells," *Nature* 329:539–541 (1987).

Palmer, T.D. et al., "Production of Human Factor IX in Animals by Genetically Modified Skin Fibroblasts: Potential Therapy for Hemophilia B," *Blood* 73:438–445 (1989).

Partridge, T.A. et al., "Conversion of mdx myofibres from dystrophin–negative to –positive by injection of normal myoblasts," *Nature* 337:176–179 (1989).

Paul, N.L. and Ruddle, N.H., "Lymphotoxin," *Ann. Rev. Immunol.* 6:407–438 (1988).

Pimentel, E., *Handbook of Growth Factors. vol. I: General Basic Aspects*, CRC Press, Boca Raton, FL, pp. 28–34 (1994).

Pimentel, E., *Handbook of Growth Factors, vol. II: Hematopoietic Growth Factors and Cytokines*, CRC Press, Boca Raton, FL, pp. 241–278 (1994).

Pokholok, D.K. et al., "Cloning and expression analysis of the murine lymphotoxin β gene," *Proc. Natl. Acad. Sci. USA* 92:674–678 (1995).

Qin, Z. and Blankenstein, "Tumor Growth Inhibition Mediated by Lymphotoxin: Evidence of B Lymphocyte Involvement in the Antitumor Response," *Canc. Res.* 55:4747–4751 (1995).

Qin, Z. et al., "Human Lymphotoxin Has at Least Equal Antitumor Activity in Comparison to Human Tumor Necrosis Factor But Is Less Toxic in Mice," *Blood* 85(10):2779–2785 (1995).

Rich, D.P. et al., "Expression of cystic fibrosis transmembrane conductance regulator corrects defective chloride channel regulation in cystic fibrosis airway epithelial cells," *Nature* 347:358–363 (1990).

Rosenberg, S.A. et al., "A New Approach to the Adoptive Immunotherapy of Cancer with Tumor–Infiltrating Lymphocytes,× Infiltrating Lymphocytes," *Science* 233:1318–1321 (1986).

Rosenberg, S.A. et al., "Use of Tumor–Infiltrating Lymphocytes and Interleukin–2 in the Immunotherapy of Patients with Metastatic Melanoma," *N. Engl. J. Med.* 319:1676–1680 (1988).

Rosenberg, S.A. et al., "Gene Transfer into Humans— Immunotherapy of Patients with Advanced Melanoma, Using Tumor–Infiltrating Lymphocytes Modified by Retroviral Gene Transduction," *N. Engl. J. Med.* 323:570–578 (1990).

Rubin, B.Y. et al., "Nonhematopoietic Cells Selected for Resistance to Tumor Necrosis Factor Produce Tumor Necrosis Factor," *J. Exp. Med.* 164:1350–1355 (1986).

Sarin, A. et al., "Cytotoxic Effect of TNF and Lymphotoxin on T Lymphoblasts," *J. Immunol.* 155:3716–3718 (1995).

Sato, H. et al., "A matrix metalloproteinase expressed on the surface of invasive tumour cells," *Nature* 370:61–65 (1994).

Schirrmacher, V., "Cancer Metastasis: Experimental Approaches, Theoretical Concepts, and Impacts for Treatment Strategies," *Adv. Cancer Res.* 43:1–73 (1985).

Senin, V.M. et al., "A New Line of Metastatic Murine Carcinosarcoma," *Experim. Oncol. (USSR)* 5:35–39 (1983).

Senin, V.M. et al., "New Organotropic–Metastatic Transplanted Tumors of Mice and Their Use for Studying Laser Effects on Dissemination," *Vestn. Akad. Med. Nauk (SSSR)* 0:85–91 (1984).

Sheehan, K.C.F. et al., "Generation and Characterization of Hamster Monoclonal Antibodies that Neutralize Murine Tumor Necrosis Factors," *J. Immunol.* 142:3884–3893 (1989).

Smith, C.A. et al., "The TNF Receptor Superfamily of Cellular and Viral Proteins: Activation, Costimulation, and Death," *Cell* 76:959–962 (1994).

Sonnenberg, A. et al., "In Vitro Differentiation and Progression of Mouse Mammary Tumor Cells," *Cancer Res.* 46:5913–5922 (1986).

Sorge, J. et al., "Complete correction of the enzymatic defect of type I Gaucher disease fibroblasts by retroviral–mediated gene transfer," *Proc. Natl. Acad. Sci. USA* 84:906–909 (1987).

Spies, T. et al., "Genes for the tumor necrosis factors α and β are linked to the human major histocompatibility complex," *Proc. Natl. Acad. Sci.* 83:8699–8702 (1986).

Spriggs, D.R. et al., "Tumor Necrosis Factor Expression in Human Eipthelial Tumor Cell Lines," *J. Clin. Invest.* 81:455–460 (1988).

Stetler–Stevenson, W.G. et al., "Tumor cell interactions with the extracellular matrix during invasion and mitastasis," *Annu. Rev. Cell Biol.* 9:541–573 (1993).

Tanaka, M. et al., "Expression of the functional soluble form of human Fas ligand in activated lymphocytes," *EMBO J.* 14:1129–1135 (1995).

Toh, Y. et al., "A Novel Candidate Metastasis–associated Gene, mta1, Differentially Expressed in Highly Metastatic Mammary Adenocarcinoma Cell Line," *J. Biol. Chem.* 269:22958–22963 (1994).

Traunecker, A. et al., "Soluble CD4 molecules neutralize human immunodeficiency virus type 1," *Nature* 331:84–86 (Jan. 1988).

Vassalli, P., "The Pathophysiology of Tumor Necrosis Factors," *Ann. Rev. Immunol.* 10:411–452 (1992).

Wiley, S.R. et al., "Identification and Characterization of a New Member of the TNF Family that Induces Apoptosis," *Immunity* 3:673–682 (1995).

Wolf, C. et al., "Stromelysin 3 belongs to a subgroup of proteinases expressed in breast carcinoma fibroblastic cells and possibly implicated in tumor progression," *Proc. Natl. Acad. Sci. USA* 90:1843–1847 (1993).

Zhang, L. et al., "Gene Expression Profiles in Normal and Cancer Cells," *Science* 276:1268–1271 (May 1997).

\* cited by examiner

Fig. 1

```
ATG TTG TTT GCC TGT GCT CTC CTT GCC CTC CTG GGT CTG GCA ACC TCC
Met Leu Phe Ala Cys Ala Leu Leu Ala Leu Leu Gly Leu Ala Thr Ser
 1               5                  10                  15

TGC AGT TTC ATC GTG CCC CGC AGT GAG TGG AGG GCC CTG CCA TCC GAG
Cys Ser Phe Ile Val Pro Arg Ser Glu Trp Arg Ala Leu Pro Ser Glu
             20                  25                  30

TGC TCT AGC CGC CTG GGG CAC CCA GTT CGC TAC GTG GTG ATC TCA CAC
Cys Ser Ser Arg Leu Gly His Pro Val Arg Tyr Val Val Ile Ser His
         35                  40                  45

ACA GCC GGC AGC TTC TGC AAC AGC CCG GAC TCC TGT GAA CAG CAG GCC
Thr Ala Gly Ser Phe Cys Asn Ser Pro Asp Ser Cys Glu Gln Gln Ala
     50                  55                  60

CGC AAT GTG CAG CAT TAC CAC AAG AAT GAG CTG GGC TGG TGC GAT GTA
Arg Asn Val Gln His Tyr His Lys Asn Glu Leu Gly Trp Cys Asp Val
 65                  70                  75                  80

GCC TAC AAC TTC CTT ATT GGA GAG GAC GGT CAT GTC TAT GAA GGC CGA
Ala Tyr Asn Phe Leu Ile Gly Glu Asp Gly His Val Tyr Glu Gly Arg
                 85                  90                  95

GGC TGG AAC ATC AAG GGT GAC CAC ACA GGG CCC ATC TGG AAT CCC ATG
Gly Trp Asn Ile Lys Gly Asp His Thr Gly Pro Ile Trp Asn Pro Met
            100                 105                 110

TCT ATT GGC ATC ACC TTC ATG GGG AAC TTC ATG GAC CGG GTA CCC GCA
Ser Ile Gly Ile Thr Phe Met Gly Asn Phe Met Asp Arg Val Pro Ala
        115                 120                 125

AAG CGG GCC CTC CGT GCT GCC CTA AAT CTT CTG GAA TGT GGG GTG TCT
Lys Arg Ala Leu Arg Ala Ala Leu Asn Leu Leu Glu Cys Gly Val Ser
    130                 135                 140

CGG GGC TTC CTG AGA TCC AAC TAT GAA GTC AAA GGA CAC CGG GAT GTG
Arg Gly Phe Leu Arg Ser Asn Tyr Glu Val Lys Gly His Arg Asp Val
145                 150                 155                 160

CAA AGC ACT CTC TCT CCA GGT GAC CAA CTC TAT CAG GTC ATC CAA AGC
Gln Ser Thr Leu Ser Pro Gly Asp Gln Leu Tyr Gln Val Ile Gln Ser
                    165                 170                 175

TGG GAA CAC TAC CGA GAG TGA
Trp Glu His Tyr Arg Glu
                180
```

Fig. 12a
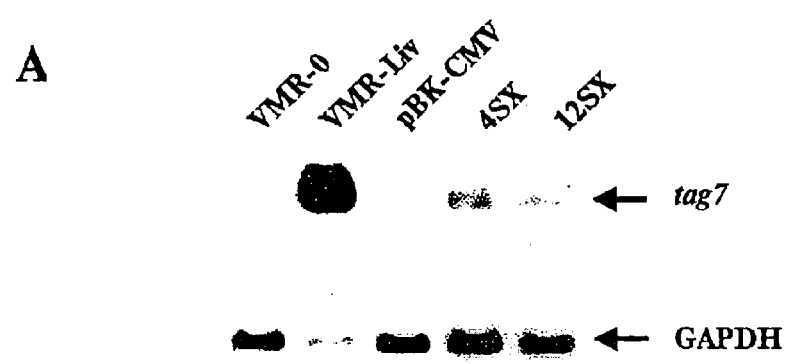
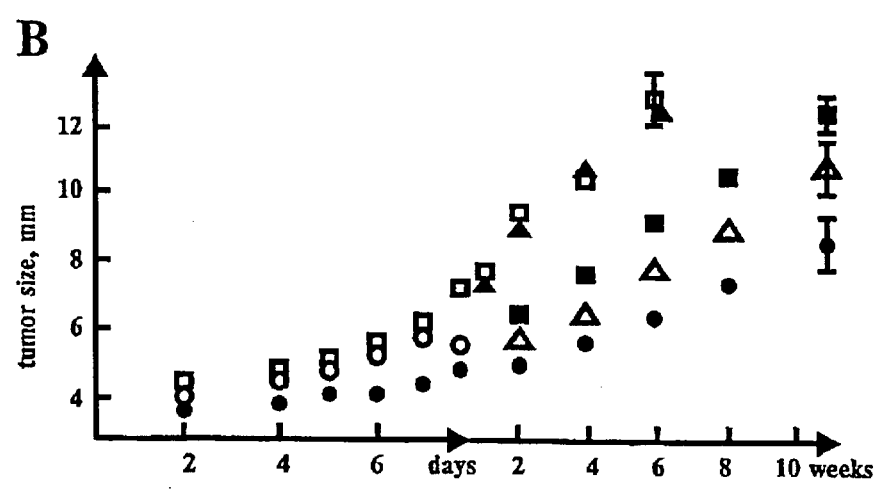

Fig. 12b
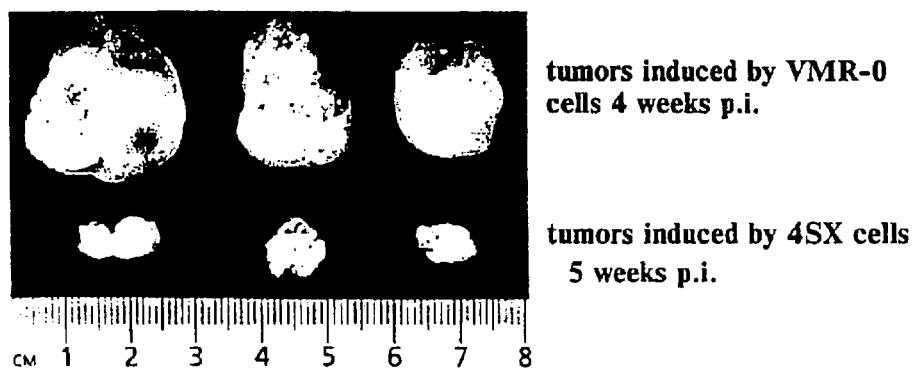
C
tumors induced by VMR-0 cells 4 weeks p.i.
tumors induced by 4SX cells 5 weeks p.i.
D ← Tag7
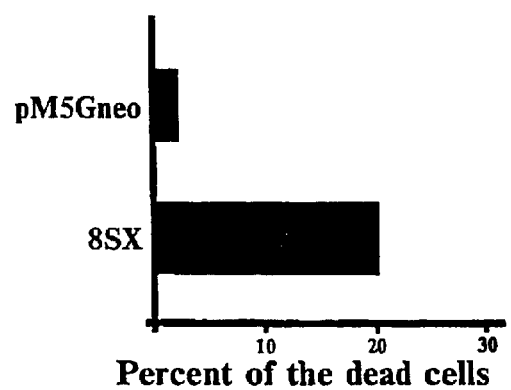
Percent of the dead cells Fig. 15a
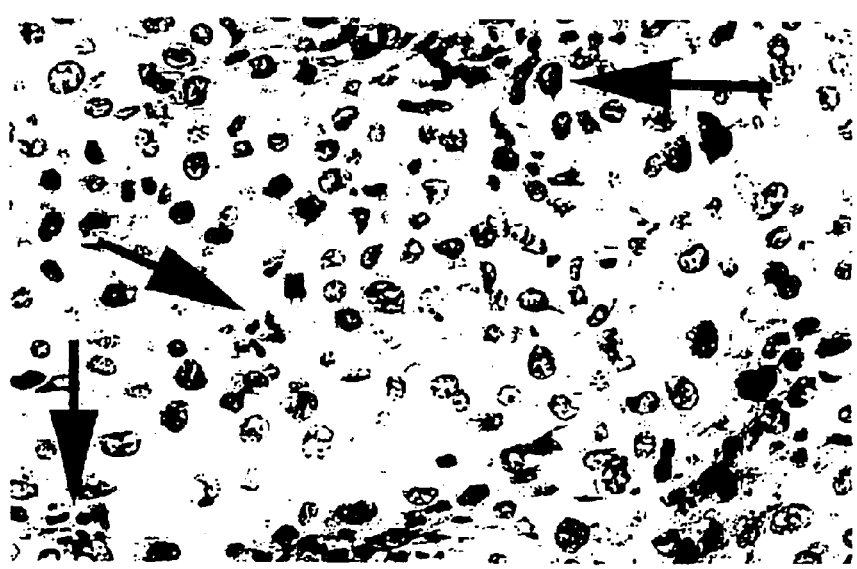

Fig. 16
A
B
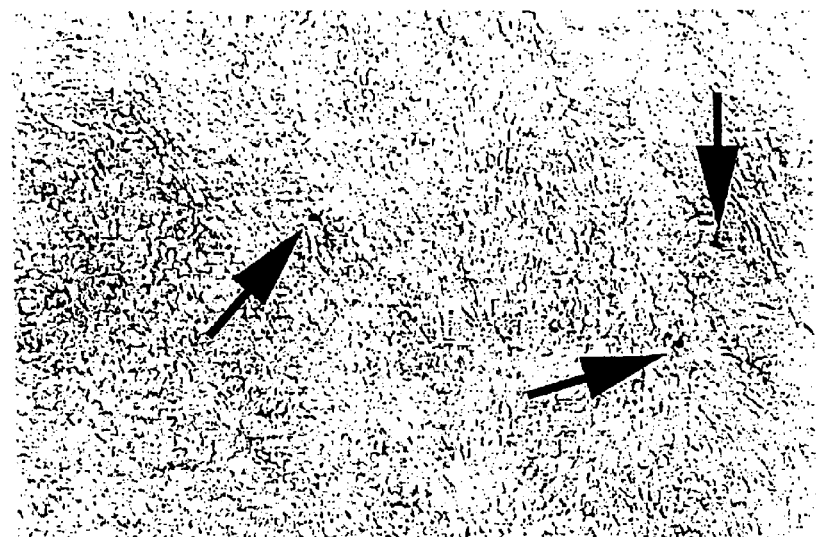

TUMOR GROWTH INHIBITION- AND APOPTOSIS-ASSOCIATED GENES AND POLYPEPTIDES AND METHODS OF USE THEREOF

CROSS-REFERENCE TO RELATED APPLICATIONS

This application is a U.S. National Phase of International Application No. PCT/EP98/04287, filed Jul. 10, 1998, published in English as WO 99/02686 on Jan. 21, 1999, and a continuation-in-part of U.S. application Ser. No. 08/893,764, filed Jul. 11, 1997, now U.S. Pat. No. 6,172,211.

BACKGROUND OF THE INVENTION

1. Field of the Invention

The present invention is in the fields of molecular biology, cancer biology and medical therapeutics. The invention is generally directed to the identification of genes that inhibit the growth of, and induce apoptosis in, cancer cells, and to polypeptides encoded by such genes. In particular, the invention concerns the nucleotide sequence of one such tumor-inhibiting gene, tag7, the amino acid sequence of a polypeptide encoded by tag7, antibodies that specifically bind to the tag7 gene product, and methods of inhibiting cancer cell growth and of cancer therapy using the tag7 gene and gene product.

2. Related Art

Tumor Metastasis

The metastasis of tumor cells is a complex process which includes a complex cascade of events. Included among these events are the proliferation of tumor cells and blocking of the apoptosis mechanism (Harrington, E. A., et al., *EMBO J.* 13:3286–3295 (1994)), the spread of the tumor cells into surrounding tissues, the penetration of tumor cells into the blood and lymphatic circulations, and the attachment and multiplication of tumor cells at a new site (Schirmacher, A. E., *Adv. Cancer Res.* 43:1–42 (1985); Liotta, L. A., et al., *Lab. Invest.* 49:636–649 (1983)). While the molecular mechanisms of the induction of the metastatic phenotype remain poorly studied, it is likely that activation and/or inactivation of a variety of regulatory and structural genes occur as a tumor becomes metastatic. Several genes whose expression correlates with the metastatic potential of tumors have been described (Yasushi, T., et al., *J. Biol. Chem.* 269(37):22958–22963 (1994); Ebralidze, A. K., et al., *Genetika (USSR)* 25(5):932–936 (1989); Wolf, C., et al., *Proc. Natl. Acad. Sci. USA* 90:1843–1847 (1993); Bernhard, E. J., et al., *Proc. Natl. Acad. Sci. USA* 91:4293–4297 (1994); Sato, H., et al., *Nature* 370:61–65 (1994)).

It has been suggested that the population of cells within a given tumor may be heterogeneous with respect to their metastatic potential (Fidler, I. J., and Hart, I. R., *Science* 217:998–1001 (1982)). This suggestion offers the possibility of obtaining related tumors that differ markedly in metastatic potential from one parent tumor. For example, tumors that are transplantable to mice and that have a varying frequency and organ-specificity of metastasis have been obtained (Senin, V. M., *Vestn. Akad. Med. Nauk. SSSR* 0(5):85–91 (1984)) as a result of selection for the metastasis character.

Tumor-inhibiting Polypeptides

A number of polypeptides naturally produced by mammalian cells have been shown to have anti-tumor activity (i.e., inducing growth arrest, apoptosis and/or differentiation of cancer cells). For example, combinations of certain cytokines, such as interleukins and colony-stimulating factors, have been reported to induce terminal differentiation and concomitant growth arrest of particular types of tumor cells and cell lines (reviewed by Pimental E., in: *Handbook of Growth Factors*, Vol. 1, Boca Raton, Fla.: CRC Press, pp. 28–34 (1994)). In addition, transforming growth factor β (TGF-β) and the interferons are known to be potent growth inhibitors for tumor cells under certain conditions in vivo and in vitro (Keski-Oja, J., and Moses, H. L., *Med. Biol.* 66:13–20 (1987); Ohta, M., et al., *Nature* 329:539–541 (1987)). Other natural mammalian polypeptides having a variety of tumoricidal activities, such as the induction of apoptosis in certain tumor cells, include the tumor necrosis factors (TFNs) (reviewed by Pimental, E., in: *Handbook of Growth Factors*, Vol. 3, Boca Raton, Fla.: CRC Press, pp. 241–278 (1994)).

Recently, a family of TNF-related cytokines and their receptors with somewhat common structural features has been identified. This family includes the TNF, LT-α, LT-β, Fas, CD27, CD40, OX-40, and nerve growth factor (NGF) receptor-ligand systems (Smith, C., et al., *Cell* 76:959–962 (1994); Armitage, R. J., *Curr. Opin. Immunol.* 6:407–413 (1994)). With the exception of NGF, all of these TNF-related cytokines are thought to be involved in the regulation of the immune System TNF and lymphotoxin-alpha (LT-α or TNF-β) are related cytokines involved in many regulatory activities (Vassalli, P., *Ann. Rev. Immunol.* 10: 411–452 (1992); Paul, N., and Ruddle, N., *Ann. Rev. Immunol.* 6:407–438 (1988)) but their roles in the immune system, while apparently critical, remain enigmatic (de Kossodo, S., et al., *J. Exp. Med.* 176:1259–1264 (1992)). TNF is synthesized in response to various insults by a variety of cell types; this is generally regarded as one of the primary events in the inflammatory cascade, including a potent antitumor effect on mice (Blankenstein, T., et al., *J. Exp. Med* 173:1047–1052 (1991)). Activated macrophages are the major source of membrane-bound TNF, although it is also produced by activated lymphocytes and several other cell types. In contrast, LT-α is produced specifically by lymphocytes and exists in membrane-associated form only via a trimeric complex with LT-β (Browning, J., et al., *Cell* 72:847–855 (1993)). LT-β shows a spectrum of activities similar to that of TNF in in vitro systems, but is less potent (Browning, J., and Ribolini, A., *J. Immunol.* 143:1859–1867 (1989)). Both TNF and LT-α induce apoptosis in various systems (Cohen, J. J., et al., *Ann. Rev. Immunol.* 10:267–293 (1992); Golstein, P., et al., *Immunol. Rev.* 121:29–65 (1991); Sarin, A., et al., *J. Immunol.* 155:3716–3718 (1995)). Recently, tumor growth inhibition mediated by LT-α has been reported (Qin, Z., and Blankenstein, T., *Cancer Res.* 55:4747–4751 (1995)).

TNF and LT-α are also released by a number of tumor cells of various origins, such as mouse fibrosarcomas, human epithelial cell lines and T-cell leukemia cells and cell lines (Rubin, B. Y., et al., *J. Exp. Med.* 164:1350–1355 (1986); Spriggs, D. R., et al., *J. Clin. Invest.* 81:455–460 (1988); Ishibashi, K., et al., *Blood* 77:2451–2455 (1991)). The genes encoding TNF, LT-α and LT-β lie closely spaced within the class III region of the major histocompatibility complex (MHC) (Spies, T., et al., *Proc. Natl. Acad. Sci. USA* 83:8699–8702 (1986); Nedospasov, S. A., et al., *Nucl. Acids Res.* 14:7713–7725 (1986); Gardner, S. M., et al., *J. Immunol.* 139:476–483 (1987)). These genes are thought to be evolutionarily related and are though to have formed the locus by tandem gene duplications, although the opposite orientation of LT-β transcription suggests that more complex evolutionary events may have taken place. Recently, another novel TNF family member has been cloned and designated as TNF-related apoptosis-inducing ligand (TRAIL) (Wiley, S. R., et al., *Immunity* 3:673–682 (1995)).

BRIEF SUMMARY OF THE INVENTION

The present invention generally relates to tumor-inhibiting genes and polypeptides, and methods of treating cancers using these genes and polypeptides. Specifically, the invention provides isolated tag7 nucleic acid molecules comprising a polynucleotide having a nucleotide sequence at least about 65% (more preferably at least about 70%, at least about 75%/o, at least about 80%, at least about 85%, at least about 90%, at least about 95% or at least about 99%) identical to a reference sequence selected from the group consisting of:

(a) the nucleotide sequence set forth in SEQ ID NO:1;

(b) a nucleotide sequence encoding the tag7 polypeptide having the complete amino acid sequence set forth in SEQ ID NO:2;

(c) the nucleotide sequence encoding the mature tag7 polypeptide having the amino acid sequence at positions about 20–182 in SEQ ID NO:2;

(d) a nucleotide sequence of a polynucleotide which hybridizes under stringent conditions to a polynucleotide having the nucleotide sequence set forth in SEQ ID NO:1;

(e) a nucleotide sequence of a polynucleotide which hybridizes under defined conditions to a polynucleotide having the nucleotide sequence set forth in SEQ ID NO:1; and (f) a nucleotide sequence complementary to any of the nucleotide sequences in (a), (b), (c), (d) or (e), or a fragment thereof.

The invention is also directed to an isolated nucleic acid molecule comprising a polynucleotide which hybridizes under stringent conditions to a polynucleotide having a nucleotide sequence identical to that of the isolated nucleic acid molecules described above, which may or may not encode a polypeptide having tag7 activity.

The invention is also directed to an isolated nucleic acid molecule comprising a polynucleotide which hybridizes under defined conditions to a polynucleotide having a nucleotide sequence identical to that of the isolated nucleic acid molecules described above, which may or may not encode a polypeptide having tag7 activity.

In a preferred embodiment, the invention is directed to isolated tag7 nucleic acid molecules comprising a polynucleotide having (a) the nucleotide sequence set forth in SEQ ID NO;3;

(b) a nucleotide sequence encoding the human tag7 polypeptide having the complete amino acid sequence set forth in SEQ ID NO:4;

(c) a nucleotide sequence of a polynucleotide which hybridizes under stringent conditions to a polynucleotide having the nucleotide sequence set forth in SEQ ID NO:3;

(d) a nucleotide sequence of a polynucleotide which hybridizes under defined conditions to a polynucleotide having the nucleotide sequence set forth in SEQ ID NO:3; and (e) a nucleotide sequence complementary to any of the nucleotide sequences in (a), (b), (c) or (d), or a fragment thereof.

The invention also provides vectors, particularly expression vectors, comprising these isolated nucleic acid molecules, and host cells comprising these isolated nucleic acid molecules or vectors. Preferred host cells of the invention include, but are not limited to, bacterial cells, yeast cells, animal cells (especially mammalian cells or insect cells) and plant cells.

The invention also relates to methods for producing an isolated tag7 polypeptide, comprising culturing the above-described host cells under conditions sufficient to allow the expression of a tag7 polypeptide, and isolating the polypeptide. The invention is also directed to isolated tag7 polypeptides produced according to these methods.

The invention also is directed to isolated tag7 polypeptides having an amino acid sequence at least about 65% (more preferably at least about 70%, at least about 75%, at least about 80%, at least about 85%, at least about 90%, at least about 95% or at least about 99%) identical to a reference sequence selected from the group consisting of:

(a) the amino acid sequence encoded by an isolated nucleic acid molecule having a nucleotide sequence as set forth in SEQ ID NO:1;

(b) the complete amino acid sequence of the tag7 polypeptide as set forth in SEQ ID NO:2;

(c) the amino acid sequence of a tag7 polypeptide encoded by a polynucleotide which hybridizes under stringent conditions to a polynucleotide having a nucleotide sequence as set forth in SEQ ID NO:1; and (d) the amino acid sequence of a tag7 polypeptide encoded by a polynucleotide which hybridizes under defined conditions to a polynucleotide having a nucleotide sequence as set forth in SEQ ID NO:1, or a fragment thereof In a preferred embodiment, the invention is directed to a human tag7 polypeptide having (a) the amino acid sequence encoded by an isolated nucleic acid molecule having a nucleotide sequence as set forth in SEQ ID NO:3;

(b) the amino acid sequence of the tag7 polypeptide as set forth in SEQ ID NO:4; or a fragment thereof.

The invention also relates to pharmaceutical compositions comprising one or more of the above-described isolated tag7 polypeptides or fragments thereof and a pharmaceutically acceptable carrier or excipient therefor.

The invention also relates to methods of producing an isolated tag7-specific antibody comprising immunizing an animal with the above-described isolated tag7 polypeptides, and isolating a tag7-specific antibody from the animal. The invention is also directed to isolated tag7-specific antibodies produced by these methods. The antibodies of the invention may be polyclonal or monoclonal antibodies, and may be detectably labeled or immobilized on a solid support.

The invention also relates to methods of inhibiting the growth of a mammalian tumor, such as a human tumor. In one preferred embodiment, such methods of the invention may comprise contacting a mammalian cell with a composition comprising one or more isolated tag7 polypeptides, wherein the isolated tag7 polypeptide has an amino acid sequence at least about 65% identical (more preferably at least about 70%, at least about 75%, at least about 80%, at least about 85%, at least about 90%, at least about 95% or at least about 99% identical) to a reference sequence selected from the group consisting of:

(a) the amino acid sequence encoded by an isolated nucleic acid molecule having a nucleotide sequence as set forth in SEQ ID NO:1;

(b) the complete amino acid sequence of the tag7 polypeptide as set forth in SEQ ID NO:2;

(c) the amino acid sequence of the mature tag7 polypeptide having the amino acid sequence as set forth at positions 20 to 182 in SEQ ID NO:2;

(d) the amino acid sequence encoded by a polynucleotide which hybridizes under stringent conditions to a polynucleotide having a nucleotide sequence as set forth in SEQ ID NO:1; and (e) the amino acid sequence encoded by a polynucleotide which hybridizes under defined conditions to a polynucleotide having a nucleotide sequence as set forth in SEQ ID NO:1, wherein the contacting of the mammalian cell with the tag7 polypeptide inhibits the growth of the cell.

In a preferred embodiment of this method, the mammalian tumor is a human tumor, and human cells are contacted with a composition comprising human tag7 polypeptide having the amino acid encoded by an isolated nucleic acid molecule having a nucleotide sequence as set forth in SEQ ID NO:3; or a fragment thereof.

In another preferred embodiment, the invention relates to methods of inhibiting the growth of a mammalian tumor comprising introducing into a mammalian cell a nucleic acid molecule comprising a polynucleotide having a nucleotide sequence at least about 65% (more preferably at least about 70%, at least about 75%, at least about 80%, at least about 85%, at least about 90%, at least about 95% or at least about 99%) identical to a reference sequence selected from the group consisting of:

(a) the nucleotide sequence set forth in SEQ ID NO:1;

(b) a nucleotide sequence encoding the tag7 polypeptide having the complete amino acid sequence set forth in SEQ ED NO:2;

(c) a nucleotide sequence encoding the mature tag7 polypeptide having the amino acid sequence at positions 20 to 182 in SEQ ED NO:2;

(d) the nucleotide sequence of a nucleic acid molecule encoding a tag7 polypeptide, comprising a polynucleotide which hybridizes under stringent conditions to a polynucleotide having a nucleotide sequence as set forth in SEQ ID NO:1; and (e) the nucleotide sequence of a nucleic acid molecule encoding a tag7 polypeptide, comprising a polynucleotide which hybridizes under defined conditions to a polynucleotide having a nucleotide sequence as set forth in SEQ ID NO:1, wherein the introduction of the isolated nucleic acid molecule into the mammalian cell inhibits the growth of the tumor.

In a preferred embodiment, the invention relates to methods of inhibiting the growth of a human tumor comprising introducing into a human cell a nucleic acid molecule comprising the human tag7 polynucleotide having the nucleotide sequence as set forth in SEQ ID NO: 3 or a fragment thereof.

According to the invention, the above-described tumor may be induced to undergo apoptosis through the action of the present methods. Preferred mammalian tumors inhibited from growing according to the methods of the invention include human tumor cells, particularly carcinoma cells (including but not limited to liver carcinoma cells, ovarian carcinoma cells, breast carcinoma cells, cervical carcinoma cells, lung carcinoma cells, prostatic carcinoma cells, gastric carcinoma cells, bladder carcinoma cells, testicular carcinoma cells, colorectal carcinoma cells, pancreatic carcinoma cells, oral cavity carcinoma cells, squamous cell carcinoma cells, head and neck carcinoma cells and teratocarcinoma cells), sarcoma cells (including but not limited to Kaposi's sarcoma cells, fibrosarcoma cells and osteosarcoma cells), melanoma cells and leukemia cells.

The invention also relates to methods for treating a cancer in an animal (particularly a mammal such as a human) suffering therefrom. In one preferred embodiment, such methods may comprise administering to the animal a composition comprising one or more isolated tag7 polypeptides, wherein the isolated tag7 polypeptide has an amino acid sequence at least about 65% (more preferably at least about 70%, at least about 75%, at least about 80%, at least about 85%, at least about 90%, at least about 95% or at least about 99%) identical to a reference sequence selected from the group consisting of:

(a) the amino acid sequence encoded by an isolated nucleic acid molecule having a nucleotide sequence as set forth in SEQ ID NO:1;

(b) the complete amino acid sequence of the tag7 polypeptide as set forth in SEQ ID NO:2;

(c) the amino acid sequence of the mature tag7 polypeptide having the amino acid sequence as set forth at positions 20 to 182 in SEQ ID NO:2;

(d) an amino acid sequence encoded by an isolated nucleic acid molecule comprising a polynucleotide which hybridizes under stringent conditions to a polynucleotide having a nucleotide sequence as set forth in SEQ ID NO.1; and (e) an amino acid sequence encoded by an isolated nucleic acid molecule comprising a polynucleotide which hybridizes under defined conditions to a polynucleotide having a nucleotide sequence as set forth in SEQ ID NO:1, wherein the treatment inhibits the progression or growth, or induces the remission, of the cancer.

In another preferred embodiment, such methods of the invention may comprise introducing into the animal a nucleic acid molecule comprising a polynucleotide having a nucleotide sequence at least about 65% (more preferably at least about 70%, at least about 75%, at least about 80%, at least about 85%, at least about 90%, at least about 95% or at least about 99%) identical to a reference sequence selected from the group consisting of:

(a) the nucleotide sequence set forth in SEQ D) NO:1;

(b) a nucleotide sequence encoding the tag7 polypeptide having the complete amino acid sequence set forth in SEQ ID NO:2;

(c) a nucleotide sequence encoding the mature tag7 polypeptide having the amino acid sequence at positions 20 to 182 in SEQ ID NO:2;

(d) the nucleotide sequence of a polynucleotide which hybridizes under stringent conditions to a polynucleotide having the nucleotide sequence set forth in SEQ ID NO:1; and (e) the nucleotide sequence of a polynucleotide which hybridizes under defined conditions to a polynucleotide having the nucleotide sequence set forth in SEQ ID NO:1, wherein the treatment inhibits the progression or growth, or induces the remission, of the cancer.

In a preferred embodiment, such methods may comprise administering to a human a composition comprising an isolated human tag7 polynucleotide having a nucleotide sequence set forth in SEQ ID NO: 3, or one or more fragments thereof.

In another preferred embodiment, the invention relates to methods of treating a cancer in an animal suffering therefrom comprising administering to the animal one or more of the above-described pharmaceutical compositions comprising one or more isolated tag7 polypeptides of the invention.

According to the invention, the isolated tag7 polypeptides used in the above-described methods preferably have amino acid sequences at least 95% identical to the above-described reference sequences. The tag7-containing compositions used in the above-described methods may further comprise a pharmaceutically acceptable carrier or excipient for the isolated tag7 polypeptide.

Also according to the invention, the polynucleotides used in the above-described methods preferably have nucleic acid sequences at least about 65% (more preferably at least about 70%, at least about 75%, at least about 80%, at least about 85%, at least about 90%, at least about 95% or at least about 99%) identical to the above-described reference sequences, and may be contained in a vector or a virion, which may be derived from an adenovirus or an adeno-associated virus.

The animal suffering from the cancer treated by the methods of the invention may be a mammal such as a human. The cancer treated by these methods may include, without limitation, a carcinoma (such as a a liver carcinoma, an ovarian carcinoma, a breast carcinoma, a cervical carcinoma, a lung carcinoma, a prostatic carcinoma, a gastric carcinoma, a bladder carcinoma, a testicular carcinoma, a colorectal carcinoma, a pancreatic carcinoma, an oral cavity carcinoma, a squamous carcinoma, a head and neck carcinoma or a teratocarcinoma), a sarcoma (such as a Kaposi's sarcoma, a fibrosarcoma or an osteosarcoma), a melanoma or a leukemia.

Other preferred embodiments of the present invention will be apparent to one of ordinary skill in light of the following drawings and description of the invention, and of the claims.

BRIEF DESCRIPTION OF THE DRAWINGS

FIG. 1 depicts the nucleotide sequence of the coding segment of the cloned tag7 cDNA (SEQ ID NO:1) and the amino acid sequence (SEQ ID NO:2) of the tag7 polypeptide encoded by this coding sequence.

(A): Autoradiograph of Northern blot analysis of total RNA isolated from the indicated healthy mouse tissues.

(B–E): In situ hybridization of adult mouse tissue sections with $^{35}$S-labeled tag7 cRNA probes; (B): hippocampus and dentate gyrus of brain; (C): cerebellum; (D): intestine; (E): intestine digested with RNase prior to hybridization.

Figure 9:
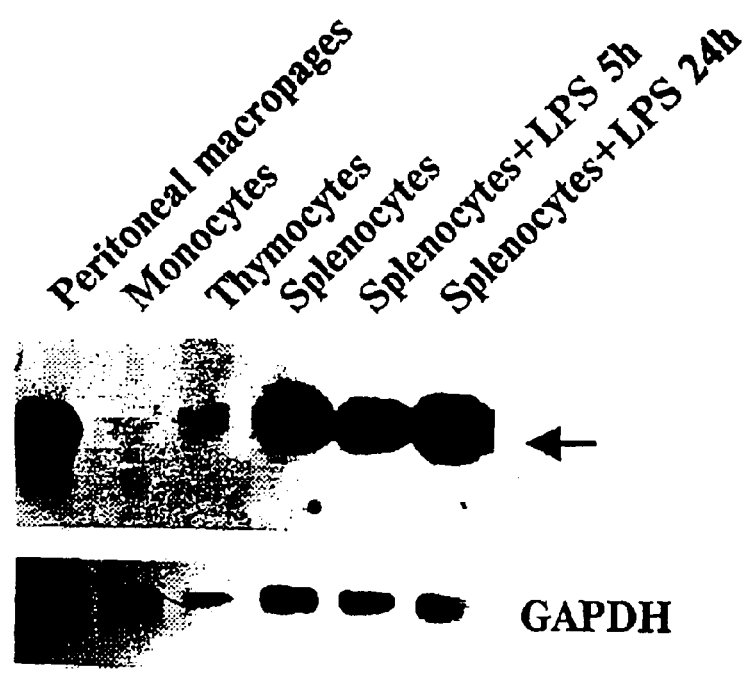

FIG. 9 is an autoradiograph of a Northern blot analysis of tag7 transcription in mouse lymphoid and hematopoietic cells cultured in media alone or in media containing lipopolysaccharide (LPS).

Figure 10:
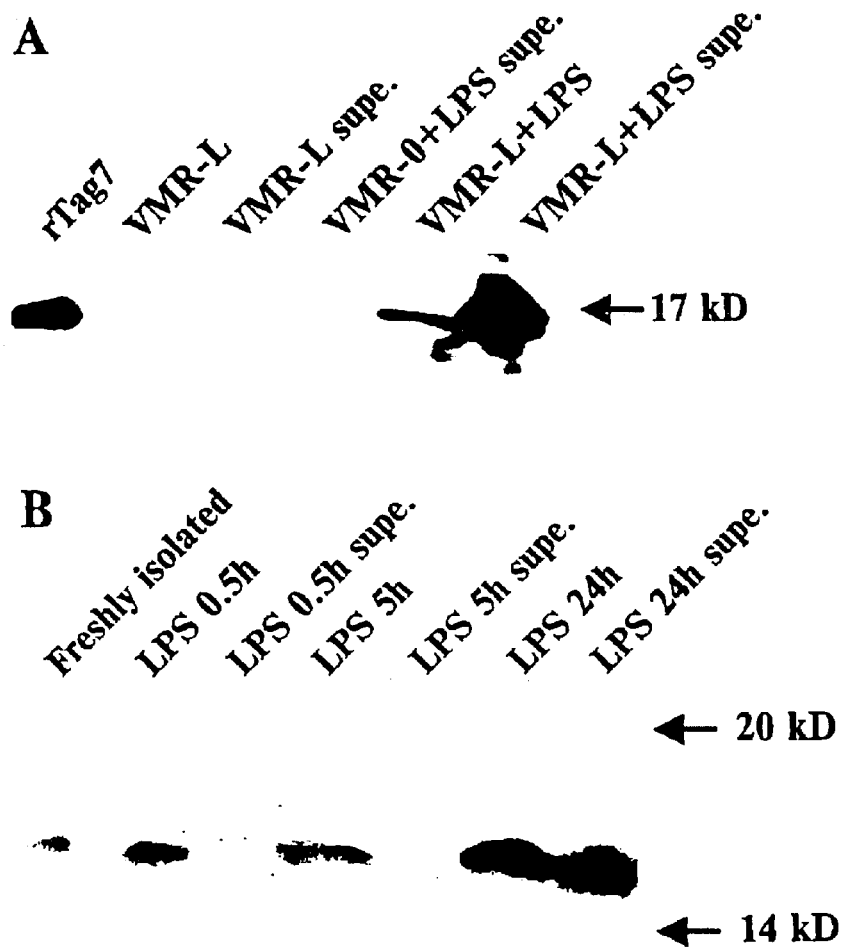

FIG. 10 is a photograph of a Western blot analysis of soluble and cell-associated forms of tag7 in various mouse cells.

(A): Cell-associated tag7. Total cell lysates and conditioned media ("supe.") of LPS-induced and uninduced VMR-L and VMR-0 mouse tumor cells were immunoprecipitated with anti-tag7 antibodies and analyzed by Western blotting, using recombinant tag7 (rTag7) as a control.

(B): Soluble tag7. Mouse splenocytes were stimulated with lipopolysaccharide for various times and lysates or supernatants were immunoprecipitated and blotted with anti-tag7 antibodies as above. Sizes of molecular mass makers are indicated by the arrows.

Figure 11:
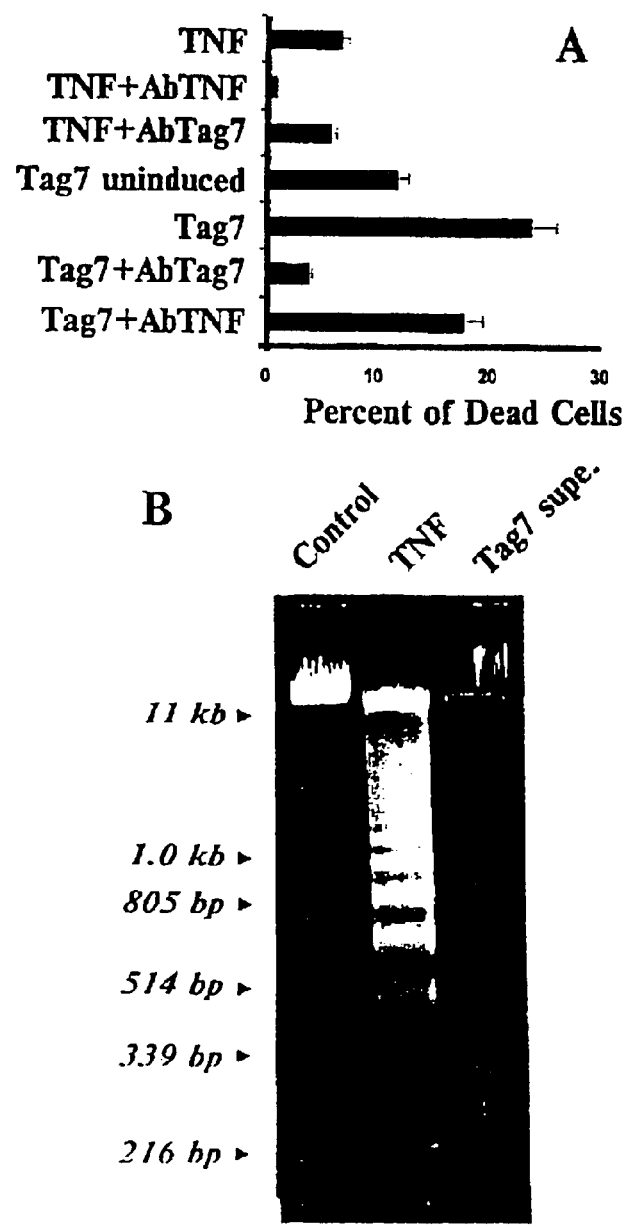

FIG. 11 is a composite bar graph (A) and photograph of an ethidium bromide-stained agarose gel (B) indicating that soluble tag7 protein induces cell death and DNA fragmentation in L929 cells.

(A): L929 cells were cultured in the presence of tag7 (LPS-stimulated VMR-L cell-conditioned media) or tumor necrosis factor (TNF), with or without anti-tag7 antibodies, and examined for cell death by trypan blue staining (conditioned medium and TNF) or lactate dehydrogenase release (TNF). Results indicate the means of five separate experiments, and error bars represent the standard deviations.

B): Photograph of ethidium bromide-stained 1.8% agarose gel electrophoresis of DNA from L929 cells that were treated with LPS alone ("control") or that were treated with TNF or supernatants of LPS-stimulated VMR-L cells ("Tag7 supe."). Position of DNA sizing markers are shown at the left.

FIG. 12 refers to in vivo tumor growth inhibition by genetically modified VMR-0 cells.

(A): Northern blot hybridization of total RNA isolated from transfected and parental cells, probed with 32P-labeled tag7 cDNA.

(B): Graph of tumor growth rate, indicating growth of cells (open boxes-parental tumor cells VMR-0, closed tiangles—mock-transfected VMR-0, open circles—suppression of 4SX growth by injection of antiTag7 polyclonal antibodies in the site of cells, closed boxes—bystander effect of coinjection of parental (VMR-0) and tag7-modified tumor cells (4SX), open triangles—growth rate of the clone 12SX, closed circles—growth rate of the clone 4SX.C—parental and modified (clone 4SX) tumors, dissected from singeneic animals.)

(C): Photographs indicating the size of the tumors formed by parental cells and by tag7-modified tumor cells (D):Detection of Tag7 protein by Western blot analysis (upper panel) and cytotoxicity of cell culture medium (lower panel).

Figure 13:
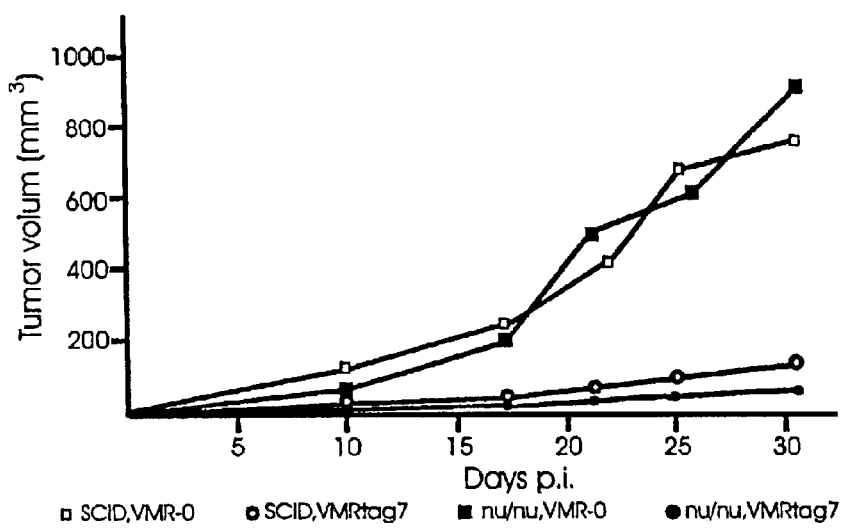

FIG. 13 shows the analysis of transformed tumor cells analyzed in nude (T cell deficient) and SCID (T and B cell deficient) mice. The tumor size was monitored during a 40 day period.

Figure 14:
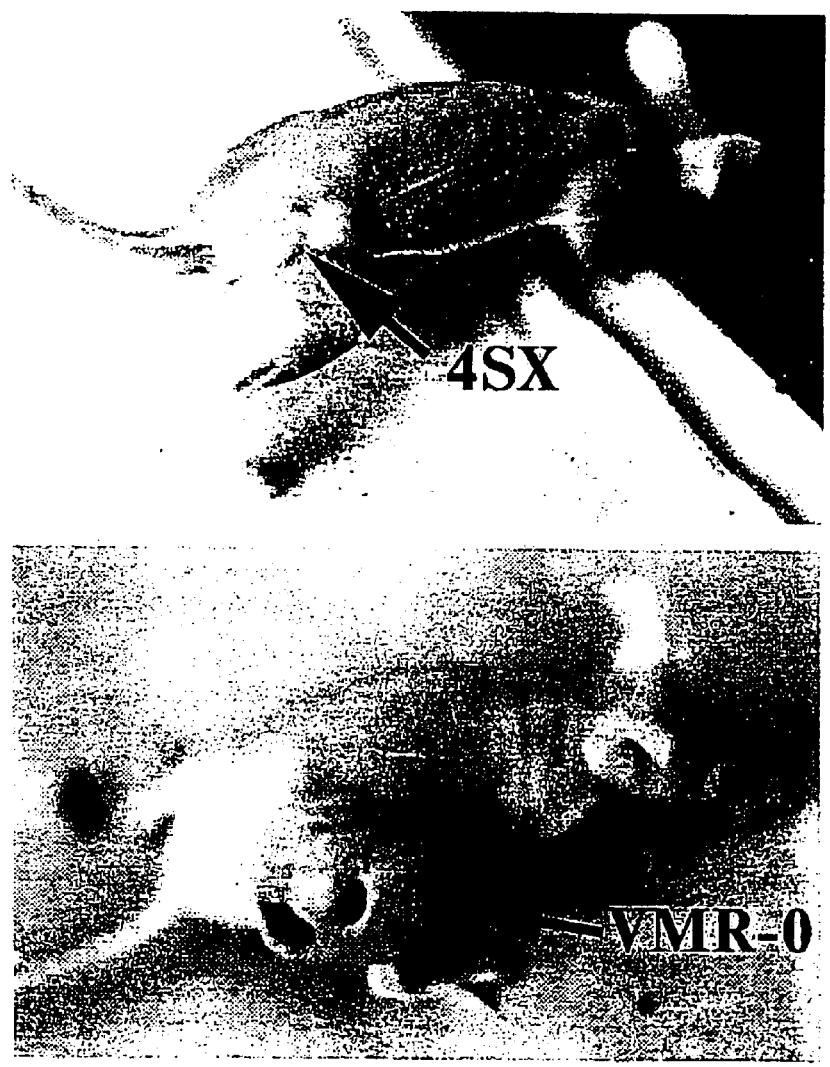

FIG. 14 shows photographs of nude mice challenged with tag7 expressing cells (4SX; upper panel)and with parental VMR-0 cells (lower panel).

FIG. 15 Histological and electron microscopy analysis (A) shows a histological section of a tumor formed by parental cells (VMR-0 cells), eosin/hematoxilyn stained (B) shows electron microscopy pictures of mitotic cells in a tumor formed by parental cells (VMR-0 cells)

(C) shows electron microscopy pictures of apoptotic cells in a tumor formed by tag7-modified cells (4SX cells).

FIG. 16: Immunohistochemical analysis. Identification of effector cells.

(A) tag7 producing tumors (4SX)

(B) Parental tumors (VMR-0)

Figure 17:
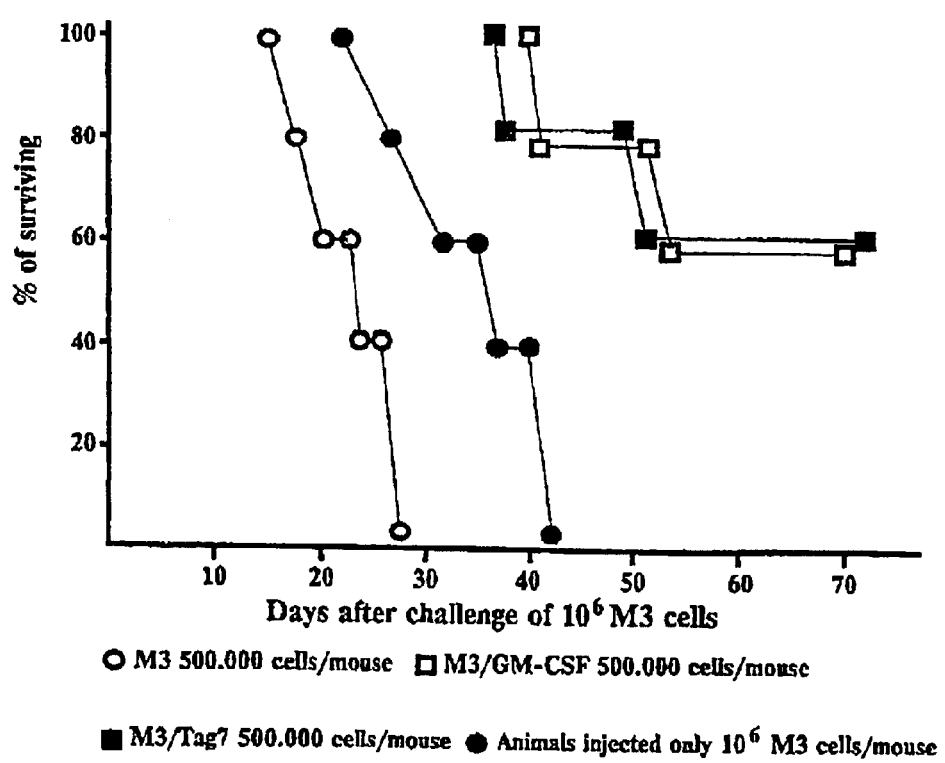

FIG. 17: Induction of protective immunity by transient expression of tag7 in mouse melanoma M3 cells. Survival rate of DBA/2 mice.

Figure 18:
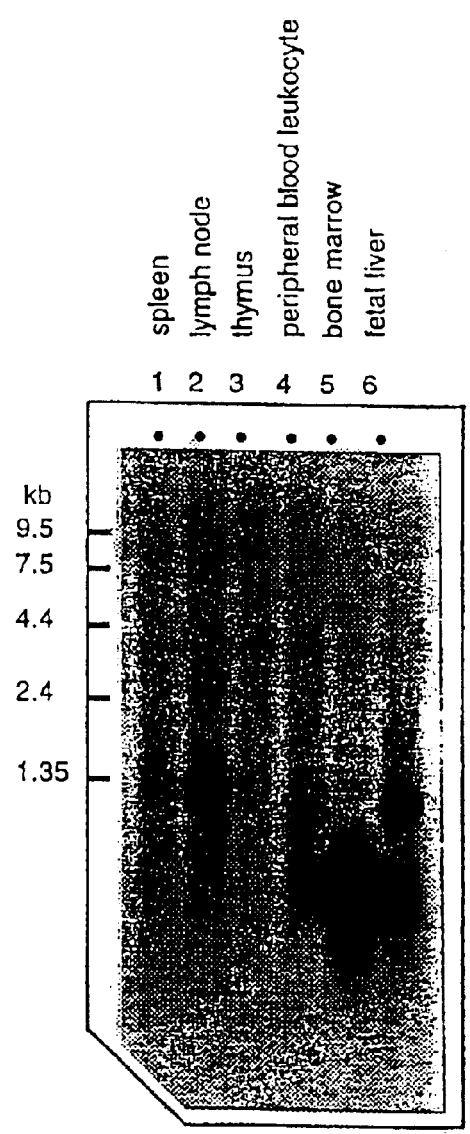

FIG. 18 is an autoradiograph of a Northern blot hybridization of total RNA isolated from various human organs probed with $^{32}$P-labeled DNA of the murine tag7 clone, demonstrating the expression of a homologue of tag7 in various human tissues.

Figure 19:
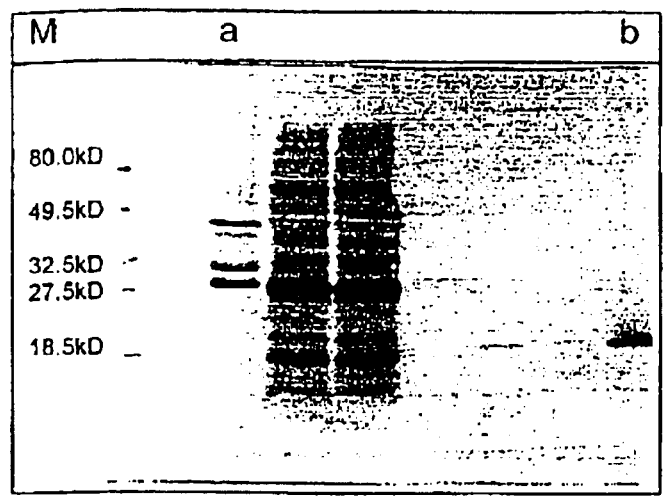

FIG. 19 shows the detection of tag 7 expressed as GST-tag7 fusion protein.

Figure 20:

FIG. 20 shows the immunohistochemical analysis of a lung adenocarcinoma with anti-Tag-7 antibodies.

DETAILED DESCRIPTION OF THE INVENTION

Overview

Two tumor lines of mouse mammary gland adenocarcinoma (VMR-0, having a low metastatic potential, and VMR-L, metastasizing to the liver at a high frequency) were used in the present invention to identify genes having a varied level of expression in tumors at various stages of progression. A previously undescribed gene expressed in the VMR-L tumor line, which has been named tag7, was obtained using the "differential RNA display" technique (Liang, P., and Pardee, A. B., Science 257:967–971 (1992)) and was characterized structurally. Although the tag7 gene was initially isolated from murine tissues, the present invention also provides a human homologue of tag7 that is expressed in human cells and tissues. It will therefore be understood by one of ordinary skill in the art that the term "tag7" as used herein refers to isolated tag7 nucleic acid molecules, polynucleotides, polypeptides and antibodies that may be of murine or human origin, and that the present invention thus encompasses tag7 nucleic acid molecules, polynucleotides, polypeptides and antibodies of murine and human origin.

Nucleic Acid Molecules

Unless otherwise indicated, all nucleotide sequences determined by sequencing a DNA molecule herein were determined using manual DNA sequencing such as dideoxy sequencing, according to methods that are routine to one of ordinary skill in the art (Sanger, F., and Coulson, A. R., *J. Mol. Biol.* 94:444 448 (1975); Sanger, F., et al., *Proc. Natl. Acad. Sci. USA* 74:5463–5467 (1977)), or by automated sequencing such as by using an Applied Biosystems Automated Sequenator according to the manufacturer's instructions. All amino acid sequences of polypeptides encoded by DNA molecules determined herein were predicted by conceptual translation of a DNA sequence determined as above. Therefore, as is known in the art for any DNA sequence determined by these approaches, any nucleotide sequence determined herein may contain some errors. Nucleotide sequences determined by such methods are typically at least about 90% identical, more typically at least about 95% to at least about 99.9% identical to the actual nucleotide sequence of the sequenced DNA molecule. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and ). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to a tag7 RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in FIG. 1, a nucleic acid molecule of the present invention encoding a tag7 polypeptide may be obtained using standard cloning and screening procedures, such as those for cloning cDNAs using mRNA as starting material. As used herein, a "tag7 polypeptide" means a polypeptide or fragment thereof that is encoded by a polynucleotide comprising the nucleotide sequence shown in FIG. 1 (SEQ ID NO:1), or that has an amino acid sequence as set forth in FIG. 1 (SEQ ID NO:2). Preferred cloning and screening methods used in the invention include PCR-based cloning methods, such as reverse transcriptase-PCR (RT-PCR) using primers such as those described in the Examples below. Illustrative of the invention, the determined nucleotide'sequence of the coding segment (549 base pairs) of the tag7 cDNA is shown in FIG. 1 (SEQ ID NO:1). The predicted 182 amino acid tag7 polypeptide encoded by this coding sequence has an amino acid sequence as set forth in FIG. 1 (SEQ ID NO:2), and a deduced molecular weight of about 20 KDa.

The present invention also provides the mature form(s) of the tag7 polypeptide of the present invention. Polypeptides secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein; that is, the cleavage pattern is inherent in the amino acid sequence of the polypeptide. As described in detail in the Examples below, the predicted tag7 polypeptide has an N-terminal hydrophobic region of between about 10 and about 30 amino acids that is homologous to the signal sequences of certain proteins, suggesting that the tag7 polypeptide may be a transmembrane or secretory protein. Therefore, the present invention provides a nucleic acid molecule encoding the mature tag7 polypeptide having the amino acid sequence encoded by a polynucleotide having a nucleic acid sequence as set forth in FIG. 1 (SEQ ID NO:1). By a mature tag7 polypeptide having the amino acid sequence encoded by a polynucleotide having a nucleic acid sequence as set forth in FIG. 1 (SEQ ID NO:1), is meant the mature form(s) of the tag7 polypeptide produced by expression in a mammalian cell (e.g., COS cells, as described below) of a polynucleotide having a nucleic acid sequence as set forth in FIG. 1 (SEQ ID NO:1). As indicated below, the mature tag7 polypeptide may or may not differ from the predicted "mature" tag7 polypeptide shown in FIG. 1 (SEQ ID NO:2; amino acids from about 20 to about 182) depending on the accuracy of the predicted cleavage site based on computer analysis.

In the case of a secretory protein, the predicted cleavage site may be preliminarily determined by applying rules previously described (Heijne et al., Eur. J. Biochem. 133:17–21 (1992)), and/or by computer analysis. According to the hydrophilicity plot obtained for the tag7 polypeptide (FIG. 2), the cleavage site for tag7 is situated at approximately amino acid residue number 20, although depending on the accuracy of this analysis the cleavage site may be expected to be anywhere from about amino acid 10 to about amino acid 30. As will be familiar to the skilled artisan, the location of the cleavage site, which defines the length of the signal peptide (in a secreted protein) or the membrane-anchoring region (in a transmembrane protein), can be confirmed by N-terminal sequencing of the tag7 protein (natural or recombinantly produced).

As one of ordinary skill will appreciate, due to the possibilities of sequencing errors, as well as the variability of cleavage sites for signal sequences in different known proteins, the actual tag7 polypeptide encoded by the polynucleotide depicted in FIG. 1 (SEQ ID NO:1) comprises about 182 amino acids, but may be anywhere in the range of about 150 to about 190 amino acids; and the actual N-terminal hydrophobic signal sequence of this protein is about 20–22 amino acids, but may be anywhere in the range of about 10 to about 30 amino acids.

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the antisense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells, and those DNA molecules purified (partially or substantially) from a solution whether produced by recombinant DNA or synthetic chemistry techniques. Isolated RNA molecules include in vivo or in vitro RNA transcripts of the DNA molecules of the present invention. However, it is intended that "isolated" as used herein does not include the tag7 cDNA present in a cDNA library or in a preparation of purified or isolated genomic DNA containing the tag7 gene or a portion thereof in admixture with one or more other cDNA molecules or DNA fragments.

The nucleic acid molecules of the present invention further include genetic constructs comprising one or more tag7 DNA sequences operably linked to regulatory DNA sequences (which may be heterologous regulatory sequences), such as promoters or enhancers as described below, wherein upon expression of these DNA sequences in host cells, preferably in bacterial, fungal (including yeast), plant or animal (including insect or mammalian) cells, one or more tag7 polypeptides are produced In such constructs, the regulatory sequences may be operably linked to a tag7 polynucleotide encoding mature lag7 polypeptide or any of its variants, precursors, fragments or derivatives described herein, which may include one or more polynucleotides having a nucleic acid sequence that is complementary to substantially all or a portion of a nucleic acid molecule having a nucleic acid sequence as shown in FIG. 1 (SEQ ID NO:1) or set forth in SEQ ID NO: 3. As used herein, the term "substantially all" of a nucleic acid molecule or a polypeptide means a portion of the nucleic acid molecule or polypeptide that contains greater than about 90%, 91%, 92%, 93%, 94%, 95%, 96%, 97%, 98% or 99%, of the nucleotide sequence shown in SEQ ID NO:1 or in SEQ ID NO:3 or of the polypeptide sequence shown in SEQ ID NO:2 or in SEQ ID NO:4. As used herein, the terms "a portion" or "a fragment" of a nucleic acid molecule or a polypeptide means a segment of a polynucleotide or a polypeptide comprising at least 15, and more preferably at least 20, contiguous nucleotides or amino acids of a reference polynucleotide or polypeptide (for example, the polynucleotide and polypeptide shown in FIG. 1 (SEQ ID NOs:1, 2, 3 and 4)), unless otherwise specifically defined below.

Isolated nucleic acid molecules of the present invention include (a) DNA molecules encoding a tag7 polypeptide, the DNA molecules having a nucleotide sequence corresponding to that depicted in FIG. 1 (SEQ ID NO:1) or in SEQ ID NO: 3; (b) DNA molecules comprising the coding sequence for the tag7 polypeptide shown in FIG. 1 (SEQ ED NO:2) or in SEQ ID NO: 4; and (c) DNA molecules which comprise a sequence substantially different from those described above but which, due to the degeneracy of the genetic code, still encode the tag7 polypeptide. Since the genetic code is well known in the art, it is routine for one of ordinary skill in the art to produce the degenerate variants described above without undue experimentation.

In another aspect, the invention provides an isolated nucleic acid molecule having a nucleotide sequence as set forth in FIG. 1 (SEQ ID NO:1) or in SEQ ID NO:3, or a nucleic acid molecule having a sequence complementary to substantially all or a portion of such a nucleic acid molecule. Such isolated molecules, particularly DNA molecules, are useful as probes for gene mapping, by in situ hybridization with chromosomes, and for detecting expression of the tag7 gene in animal (especially mammalian, including human) tissue, particularly in tumor tissues and cells, for instance, by Northern blot analysis.

Nucleic acid molecules of the present invention which encode a tag7 polypeptide may include, but are not limited to, those encoding the amino acid sequence of the mature polypeptide by itself; the coding sequence for the mature polypeptide and additional coding sequences, such as those encoding the about 20-amino acid leader or secretory sequence, such as a pre-, or pro- or prepro-protein sequence; the coding sequence of the mature polypeptide, with or without the aforementioned additional coding sequences, together with additional, non-coding sequences, including for example introns and non-coding 5' and 3' sequences, such as the transcribed, untranslated regions (UTRs) or other 5' flanking sequences that may play a role in transcription (e.g., via providing ribosome—or transcription factor-binding sites), mRNA processing (e.g. splicing and poly-adenylation signals) and stability of mRNA; the coding sequence for the mature tag7 polypeptide operably linked to a regulatory DNA sequence, particularly a heterologous regulatory DNA sequence such as a promoter or enhancer; and the coding sequence for the mature tag7 polypeptide linked to one or more coding sequences which code for amino acids that provide additional functionalities. Thus, the sequence encoding the polypeptide may be fused to a marker sequence, such as a sequence encoding a peptide which facilitates purification of the fused polypeptide. In certain embodiments of this aspect of the invention, the marker amino acid sequence may be a hexa-histidine peptide, such as the tag provided in a pQE vector (Qiagen, Inc.), among others, many of which are commercially available. As described for instance in Gentz et al., *Proc. Natl. Acad. Sci. USA* 86:821–824 (1989), hexa-histidine provides for convenient purification of the fusion protein. The "HA" tag is another peptide useful for purification which corresponds to an epitope derived from the influenza hemagglutinin protein, which has been described by Wilson et al., *Cell* 37:767 (1984). Yet another useful marker peptide for facilitation of purification of tag7 is glutathione S-transferase (GST) encoded by the pGEX fusion vector (see, e.g., Winnacker, *From Genes lo Clones*, New York: VCH Publishers, pp. 451–481 (1987)). As discussed below, other such fusion proteins include the tag7 fused to immunoglobulin Fc at the N- or C-terminus.

The present invention further relates to variants of the nucleic acid molecules of the present invention, which encode portions, analogs or derivatives of the tag7 polypeptide. Variants may occur naturally, such as a natural allelic variant. By an "allelic variant" is intended one of several alternate forms of a gene occupying a given locus on a chromosome of an organism (see Lewin, B., Ed., *Genes II*, John Wily & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the tag7 protein or portions thereof. Also especially preferred in this regard are conservative substitutions.

Further embodiments of the invention include isolated nucleic acid molecules comprising a polynucleotide having a nucleotide sequence at least about 65% identical, and more preferably at least about 70%, at least about 75%, at least about 80%, at least about 85%, at least about 90%, at least about 95%, at least about 96%, at least about 97%, at least about 98% or at least about 99% identical, to:

(a) the nucleotide sequence as set forth in FIG. 1 (SEQ ID NO:1);

(b) a nucleotide sequence encoding the full-length tag7 polypeptide having the complete amino acid sequence in FIG. 1 (SEQ ID NO:2), including the predicted N-terminal signal sequence;

(c) a nucleotide sequence encoding the mature tag7 polypeptide (full-length polypeptide with the signal sequence removed), which may, for example, have the amino acid sequence depicted at positions about 20–182 in FIG. 1 (SEQ ID NO:2);

(d) the nucleotide sequence of a tag7-encoding polynucleotide which hybridizes under stringent hybridization conditions to a polynucleotide having a nucleotide sequence identical to that of the above-described isolated nucleic acid molecules;

(e) the nucleotide sequence of a tag7-encoding polynucleotide which hybridizes under defined hybridization conditions to a polynucleotide having a nucleotide sequence identical to that of the above-described isolated nucleic acid molecules; or (f) a nucleotide sequence complementary to substantially all or a portion of any of the nucleotide sequences in (a), (b), (c), (d) or (e) above, or a fragment thereof.

By "stringent hybridization conditions" as used herein is meant overnight incubation at 42° C. in a solution comprising: 50% formamide, 5×SSC (1×SSC=150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By "defined hybridization conditions" as used herein is intended prehybridization at 65° C. for two hours in Church buffer (0.5 M sodium phosphate (pH 7.2), 7% SDS, 1 mM EDTA), denaturation at 95° C. for five minutes, addition of fresh Church buffer for hybridization at 55° C., and washing three times at 50° C. for 15 minutes each in Church wash buffer (40 mM sodium phosphate (pH 7.2), 1%SDS), or equivalent hybridization conditions in SSC or SSPE, as described in standard protocols (see, e.g., *Molecular Cloning, A Laboratory Manual*, 2nd Ed., Sambrook, J., et al., eds., Cold Spring Harbor, N.Y.: Cold Spring Harbor Laboratory Press (1989), the entire disclosure of which is hereby incorporated herein by reference).

By a polynucleotide having a nucleotide sequence at least, for example, 65% "identical" to a reference nucleotide sequence encoding a tag7 polypeptide is intended that the nucleotide sequence of the polynucleotide is identical to the reference sequence except that the polynucleotide sequence may include up to 35 point mutations per each 100 nucleotides of the reference nucleotide sequence encoding the tag7 polypeptide. In other words, to obtain a polynucleotide having a nucleotide sequence at least 65% identical to a reference nucleotide sequence, up to 5% of the nucleotides in the reference sequence may be deleted or substituted with another nucleotide, or a number of nucleotides up to 35% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least about 65%, 70%, 75%, 80%, 85%, 90%, 95%, 96%, 97%, 98% or 99% identical to, for instance, the nucleotide sequence shown in FIG. 1 (SEQ ID NO:1) or in SEQ ID NO: 3, can be determined conventionally using known computer programs such as FASTA (Heidelberg, Germany), BLAST (Washington, D.C.) or BESTFIT (Wisconsin Sequence Analysis Package, Version 8 for Unix, Genetics Computer Group, University Research Park, 575 Science Drive, Madison, Wis. 53711), which employs a local homology algorithm (Smith and Waterman, *Advances in Applied Mathematics* 2:482–489 (1981)) to find the best segment of homology between two sequences. When using FASTA, BLAST, BESTFIT or any other sequence alignment program to determine whether a particular sequence is, for instance, 65% identical to a reference sequence according to the present invention, the parameters are set such that the percentage of identity is calculated over the full length of the reference nucleotide sequence and that gaps in homology of up to 35% of the total number of nucleotides in the reference sequence are allowed, The present invention is directed to nucleic acid molecules at least about 65%, 70%, 75%, 80%, 85%, 90%, 95%, 96%, 97%, 98% or 99% identical to the nucleic acid sequence shown in FIG. 1 (SEQ ID NO:1) or in SEQ ID NO: 3, and fragments thereof, irrespective of whether they encode a polypeptide having tag7 activity. This is because even where a particular nucleic acid molecule does not encode a polypeptide having tag7 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having tag7 activity include, inter alia. (1) isolating the tag7 gene or allelic variants thereof in, a genomic DNA library; (2) in situ hybridization (e.g., "FISH") to metaphase chromosomal spreads to provide precise chromosomal location of the tag7 gene, as described for human gene localization in Verma et al., *Human Chromosomes: A Manual of Basic Techniques*, Pergamon Press, New York (1988); and (3) Northern blot analysis for detecting tag7 mRNA expression in specific tissues.

Of course, due to the degeneracy of the genetic code, one of ordinary skill inn the art will immediately recognize that a large number of the nucleic acid molecules having a sequence at least about 65%, 70%, 75%, 80%, 85%, 90%, 95%, 96%, 97%, 98%, or 99% identical to the nucleic acid sequence shown in FIG. 1 (SEQ ID NO:1) or in SEQ ID NO: 3, and fragments thereof, will encode a polypeptide having tag7 polypeptide structure and/or activity. In fact, since degenerate variants of these nucleotide sequences all encode the same polypeptide, this will be clear to the skilled artisan even without performing the above described comparison assay. It will be further recognized by one of ordinary skill in the art tat, for such nucleic acid molecules that are not degenerate variants, a reasonable number will also encode a polypeptide having tag7 polypeptide structure and/or activity. This is because the skilled artisan is fully aware of amino acid substitutions that are either less likely or unlikely to significantly affect protein function (e.g., replacing one aliphatic amino acid with a second aliphatic amino acid). For example, guidance concerning how to make phenotypically silent amino acid substitutions is provided in Bowie, J. U., et al., *Science* 247:1306–1310 (1990), and the references cited therein.

As noted above, the invention also provides fragments of the above-described nucleic acid molecules. Preferred nucleic acid fragments of the present invention include isolated nucleic acid molecules encoding epitope-bearing portions of the tag7 polypeptide. In particular, such nucleic acid fragments of the present invention include nucleic acid molecules encoding: a polypeptide comprising amino acid residues from about 20 to about 40 in FIG. 1 (SEQ ID NO:2); a polypeptide comprising amino acid residues from about 55 to about 75 in FIG. 1 (SEQ ID NO:2); a polypeptide comprising amino acid residues from about 90 to about 110 in FIG. 1 (SEQ ID NO:2); and a polypeptide having an amino acid sequence consisting essentially of amino acid residues from about 145 to about 160 in FIG. 1 (SEQ ID NO:2). The inventors have determined that the above polypeptide fragments are antigenic regions of the predicted tag7 polypeptide. Methods for determining other such epitope-bearing portions of the tag7 polypeptide, which may also be used to determine epitope-bearing regions of the human tag7 polypeptide, are described in detail below.

In another aspect, the invention provides an isolated nucleic acid molecule comprising a polynucleotide which hybridizes under stringent hybridization conditions to substantially all or a portion of the polynucleotide in a nucleic acid molecule of the invention described above, for instance, a nucleic acid molecule having a nucleotide sequence as set forth in FIG. 1 (SEQ ID NO:1) or in SEQ ID NO: 3.

In another aspect, the invention provides an isolated nucleic acid molecule comprising a polynucleotide which hybridizes under defined hybridization conditions to substantially all or a portion of the polynucleotide in a nucleic acid molecule of the invention described above, for instance, a nucleic acid molecule having a nucleotide sequence as set forth in FIG. 1 (SEQ ID NO:1) or, preferably, as set forth in SEQ ID NO: 3, and which encodes a polypeptide with tag7 activity, preferably a human tag7 polypeptide.

By a polynucleotide which hybridizes to a "portion" of a polynucleotide is intended a polynucleotide (either DNA or RNA) hybridizing to at least about 15 nucleotides, and more preferably at least about 20 nucleotides, still more preferably at least about 30 nucleotides, and even more preferably about 30–70 nucleotides of the reference polynucleotide. These hybridizing polynucleotides are useful as diagnostic probes and primers as discussed above and in more detail below.

Of course, polynucleotides hybridizing to a larger portion of the reference polynucleotide (e.g., a nucleic acid molecule consisting of the tag7 coding sequence, having the nucleotide sequence set forth in FIG. 1 (SEQ ID NO:1) or in SEQ ID NO: 3), for instance, a portion about 50–500 nucleotides in length, or even to the entire length of the reference polynucleotide, are also useful as probes according to the present invention, as are polynucleotides corresponding to most, if not all, of the nucleotide sequence of the nucleotide sequence as shown in FIG. 1 (SEQ ID NO:1) or in SEQ ID NO: 3. By a portion of a polynucleotide of "at least 20 nucleotides in length," for example, is intended 20 or more contiguous nucleotides from the nucleotide sequence of the reference polynucleotide (e.g., the nucleotide sequence as shown in FIG. 1 (SEQ ID NO:1) or in SEQ ID NO: 3.). As indicated, such portions are useful diagnostically either as a probe according to conventional DNA hybridization techniques or as primers for amplification of a target sequence by the polymerase chain reaction (PCR), as described, for instance, in Molecular Cloning, A Laboratory Manual, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a determined nucleotide sequence encoding a tag7 polypeptide is provided in FIG. 1 (SEQ ID NO:1) or in SEQ ID NO: 3., generating polynucleotides which hybridize to a portion of the tag7 cDNA molecule would be routine to the skilled artisan For example, restriction endonuclease cleavage or shearing by sonication of the tag7 cDNA clone could easily be used to generate DNA portions of various sizes which are polynucleotides that hybridize to a portion of the tag7 cDNA molecule. Alternatively, the hybridizing polynucleotides of the present invention could be generated synthetically according to known techniques. Thus, while the present invention relates to tag7 nucleic acid molecules and polypeptides from mouse and human, one of ordinary skill could easily generate and/or isolate homologues of the tag7 nucleic acid molecules and polypeptides of the invention from other organisms (particularly other mammals) using the tag7 nucleotide sequence (SEQ ID NO:1) and amino acid sequence (SEQ ID NO:2) described herein and routine molecular biology methods, e.g., screening of cDNA libraries, that are well-known in the art and described in standard protocols (see, e.g., *Molecular Cloning, A Laboratory Manual*, 2nd Ed., Sambrook, J., et al., eds., Cold Spring Harbor, N.Y.: Cold Spring Harbor Laboratory Press (1989)). For example, a cDNA library suitable for obtaining a nucleic acid molecule encoding a human homologue of tag7 hereinafter referred to as "human tag7") is a bone marrow cDNA library. Bone marrow libraries and other human tissue cDNA and genomic libraries are commercially available, for example from Clontech (Palo Alto, Calif.).

Vectors and Host Cells

The present invention also relates to genetic constructs comprising the isolated nucleic acid molecules of the invention, or fragments thereof operably linked to regulatory DNA sequences as described in detail below, vectors which comprise these genetic constructs or the isolated DNA molecules of the present invention, and host cells which comprise these vectors. In addition, the invention relates to the production of tag7 polypeptides or fragments thereof by recombinant techniques using these vectors and host cells.

Vectors comprising the genetic constructs or the isolated DNA molecules or fragments of the present invention may be introduced into host cells using well-known techniques such as infection, transduction, transfection, electroporation and transformation. The vector may be, for example, a phage, plasmid, viral or retroviral vector, and is preferably an expression vector as described below. Retroviral vectors may be replication-competent or -defective. In the latter case, viral propagation generally will occur only in complementing host cells.

The polynucleotides may be joined to a vector containing a selectable marker for propagation in a host. Generally, a plasmid vector is introduced into mammalian or avian cells in a precipitate, such as a calcium phosphate precipitate, or in a complex with a charged lipid (e.g., LIPO-FECTAMINE™; Life Technologies, Inc.; Rockville, Md.) or in a complex with a virus (such as an adenovirus; see U.S. Pat. Nos. 5,547,932 and 5,521,291) or components of a virus (such as viral capsid peptides). If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, by a complementing vector or by the vector itself upon introduction into the host.

In certain preferred embodiments in this regard, the vectors provide for specific expression, which may be inducible and/or cell type-specific. Particularly preferred among such expression vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophages, yeast episomes, yeast chromosomal elements, viruses such as baculoviruses, papovaviruses, vaccinia viruses, adenoviruses, fowl pox viruses, pseudorabies viruses and retroviruses, and vectors derived from combinations thereof, such as cosmids and phagemids.

In one embodiment, an isolated nucleic acid molecule of the invention or fragment thereof may be operably linked to an appropriate regulatory sequence, preferably a promoter such as the phage lambda PL promoter, promoters from T3, T7 and SP6 phages, the *E. coli* lac, trp and tac promoters, the SV40 early and late promoters and promoters of retroviral LTRs and derivatives thereof, to name a few. Other suitable promoters will be known to the skilled artisan The expression constructs will further contain sites for transcription initiation, termination and, in the transcribed region, a ribosome binding site for translation. The coding portion of the mature transcripts expressed by the constructs will preferably include a translation initiation codon (AUG) at the beginning and a termination codon (UAA, UGA or UAG) appropriately positioned at the end of the polypeptide to be translated.

As indicated above, the expression vectors will preferably include at least one selectable marker. Such markers include dihydrofolate reductase (dhfr) or neomycin (neo) resistance for eukaryotic cell culture and tetracycline (tet) or ampicillin (amp) resistance genes for culturing in *E. coli* and other bacteria Representative examples of appropriate hosts include, but are not limited to, bacterial cells, such as Escherichia spp. cells (particularly *E. coli*), Bacillus spp. cells particularly *B. cereus*, *B. subtilis* and *B. megaterium*), Streptomyces spp. cells, Salmonella spp. cells (particularly *S. typhimurium*) and Xanthomonas spp. cells; fungal cells, including yeast cells such as Saccharomyces spp. cells; insect cells such as Drosophila S2, Spodoptera Sf9 or Sf21 cells and Trichoplusa High-Five cells; other animal cells particularly mammalian cells and most particularly human cells) such as CHO, COS, VERO, HeLa, Bowes melanoma cells and HepG2 and other liver cell lines; and higher plant cells. Appropriate culture media and conditions for the above-described host cells are known in the art.

Among vectors preferred for use in bacteria include pQE70, pQE6 and pQE-9, available from Qiagen; pBS vectors, Phagescript vectors, Bluescript vectors, pNH8A, pNH16a, pNH18A and pNH46A, available from Stratagene; pcDNA3 available from Invitrogen; and pGEX, pTrxfus, pTrc99a, pET-5, pET-9, pKK223-3, pKK233-3. pDR540 and pRIT5 available from Pharmacia Among preferred eukaryotic vectors are pWLNEO, pSV2CAT, pOG44, pXT1, pBK and pSG available from Stratagene; and pSVK3, pBPV, pMSG and pSVL available from Pharmacia Other suitable vectors will be readily apparent to the skilled artisan.

Among known bacterial promoters suitable for use in the present invention include the *E. coli* lacI and lacZ promoters, the T3, T7 and SP6 phage promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection, nucleic acid-coated microprojectile bombardment or other methods. Such methods are described in many standard laboratory manuals, such as Davis et al., *Basic Methods In Molecular Biology* (1986).

In some embodiments, the isolated polynucleotides of the present invention may be operably linked to a regulatory genetic sequence, which may be a homologous or a heterologous regulatory genetic sequence (such as an enhancer, promoter or repressor), to form a genetic construct. Genetic constructs according to this aspect of the invention are intended to encompass not only those comprising a polynucleotide encoding mature tag7 protein operably linked to a regulatory DNA sequence, but also those constructs comprising one or more regulatory sequences operably linked to a tag7 polynucleotide fragment which does not encode tag7 protein, but which contains a sufficient portion of the tag7 nucleotide sequence (a "targeting fragment") to target the genetic construct to the native tag7 locus upon introduction into a host cell wherein the tag7 gene may be inactive due to repression or mutation. These constructs may be inserted into a vector as above, and the vectors introduced into a host cell, the genome of which comprises the target gene, by any of the methods described above. The tag7 polynucleotide will then integrate into the host cell genome by homologous recombination. In the case of a construct comprising a homologous or heterologous regulatory sequence linked to a targeting tag7 polynucleotide fragment, the regulatory sequence will be targeted to the native tag7 locus in the host cell, and will amplify or de-repress (if the regulatory sequence comprises, for example, a promoter or enhancer) or will inhibit or repress (if the regulatory sequence comprises, for example, a repressor or otherwise integrates into the native regulatory sequence to inhibit or repress (i.e., "knock out")) the expression of the native tag7 gene in the host cell, thereby increasing or decreasing the level of tag7 gene expression. Alternatively, such gene targeting may be carried out using genetic constructs comprising the above described tag7 targeting fragment in the absence of a regulatory sequence; such an approach may be used, for example, to correct or introduce point mutations in the tag7 gene (see Steeg, C.M., et al., *Proc. Natl. Acad. Sci. USA* 87(12):4680–4684 (1990) for a description of the use of such approaches to correcting point mutations in other mammalian genes). Such methods of producing genetic constructs, introducing genes of interest into a host cell via homologous recombination and producing the encoded polypeptides are generally described in U.S. Pat. No. 5,578,461; WO 94/12650 (U.S. application Ser. No. 07/985,586); WO 93/09222 (U.S. application Ser. No. 07/911,535); and WO 90/14092 (U.S. application Ser. No. 07/353,909), the disclosures of which are expressly incorporated herein by reference in their entireties.

Transcription of the DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers. In an alternative embodiment of the invention, transcriptional activation of the tag7 gene may be enhanced by inserting one or more concatamerized elements from the native human or tag7 promoter into the vector.

For secretion of the translated polypeptide into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The tag7 polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among other purposes, is a familiar and routine technique in the art A preferred fusion protein comprises a heterologous region from an immunoglobulin that is useful to solubilize proteins. For example, EP 0 464 533 discloses fusion proteins comprising various portions of constant (Fc) region of immunoglobulin molecules together with another human protein or part thereof. In many cases, the Fc portion of a fusion protein is thoroughly advantageous for use in therapy and diagnosis and thus results, for example, in improved pharmacokinetic properties (EP 0 232 262). On the other hand, for some uses it would be desirable to be able to delete the Fc part after the fusion protein has been expressed, detected and purified in the advantageous manner described. This is the case when the Fc portion proves to be a hindrance to use in therapy, diagnosis or further manufacturing, for example when the fusion protein is to be used as an antigen for immunizations for the preparation of antibodies.

The tag7 polypeptide can be recovered and purified from recombinant cell cultures by well-known methods including ammonium sulfate or ethanol precipitation, acid extraction, anion or cation exchange chromatography, lectin chromatography, gel filtration, hydrophobic interaction chromatography, affinity chromatography and hydroxylapatite chromatography. Most preferably, high performance liquid chromatography ("HPLC") is employed for purification Polypeptides of the present invention include naturally purified products, products of chemical synthetic procedures, and products produced by recombinant techniques from a prokaryotic or eukaryotic host, including, for example, bacterial, yeast, insect, mammalian, avian and higher plant cells. Depending upon the host employed in a recombinant production procedure, the polypeptides of the present invention may be glycosylated or may be non-glycosylated. In addition, tag7 polypeptides of the invention may also include an initial modified methionine residue, in some cases as a result of host-mediated processes.

Tag7 Polypeptides and Fragments

The invention further provides an isolated tag7 polypeptide having the amino acid sequence encoded by a polynucleotide having the nucleotide sequence set forth in FIG. 1 (SEQ ID NO:1), an isolated tag7 polypeptide having the amino acid sequence encoded by a polynucleotide having the nucleotide sequence set forth SEQ ID NO:3, the complete amino acid sequence in FIG. 1 (SEQ ID NO:2), the amino acid sequence of the mature tag7 polypeptide having the amino acid sequence set forth at positions about 20–182 in FIG. 1 (SEQ ID NO:2), the amino acid sequence encoded by a polynucleotide which hybridizes under stringent hybridization conditions to a polynucleotide having a nucleotide sequence as set forth in SEQ ID NO:1, the amino acid sequence encoded by a polynucleotide which hybridizes under defined hybridization conditions to a polynucleotide having a nucleotide sequence as set forth in SEQ ID NO:1, or a peptide or polypeptide comprising a portion or a fragment of the above polypeptides. As used herein, the terms "peptide" and "oligopeptide" are considered synonymous (as is commonly recognized) and each term can be used interchangeably as the context requires to indicate a chain of at least two amino acids coupled by (a) peptidyl linkage(s). The term "polypeptide" is used herein to denote chains comprising ten or more amino acid residues. As is commonly recognized in art, all oligopeptide and polypeptide formulas or sequences herein are written from left to right and in the direction from amino terminus to carboxy terminus.

It will be recognized by those of ordinary skill in the art that some amino acid sequences of the tag7 polypeptide can be varied without significant effect on the structure or function of the polypeptide. If such differences in sequence are contemplated, it should be remembered that there will be critical areas on the protein which determine structure and activity. In general, it is possible to replace residues which form the tertiary structure, provided that residues performing a similar function are used. In other instances, the type of residue may be completely unimportant if the alteration occurs at a non-critical region of the polypeptide.

Thus, the invention further includes variants of the tag7 polypeptide, including allelic variants, which show substantial tag7 polypeptide structural homology or activity, or which include regions of the tag7 polypeptide such as the portions discussed below. Such mutants may include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typical conservative substitutions are the replacements, one for another, among the aliphatic amino acids Ala, Val, Leu and Ile; interchange of the hydroxylated residues Ser and Thr; exchange of the acidic residues Asp and Glu; substitution between the amidated residues Asn and Gln; exchange of the basic residues Lys and Arg; and replacements among the aromatic residues Phe and Tyr.

Thus, the fragment, derivative or analog of the polypeptide of FIG. 1 (SEQ ID NO:2), or of the polypeptide of SEQ ID NO: 4 or that encoded by a polynucleotide having a nucleic acid sequence as set forth in FIG. 1 (SEQ ID NO:1) or in SEQ ID NO: 3, may be (i) one in which one or more of the amino acid residues are substituted with a conserved or non-conserved amino acid residue (preferably a conserved amino acid residue), and such substituted amino acid residue may be encoded by the genetic code or may be an amino acid (e.g., desmosine, citrulline, ornithine, etc.) that is not encoded by the genetic code; (ii) one in which one or more of the amino acid residues includes a substituent group (e.g., a phosphate, hydroxyl, sulfate or other group) in addition to the normal "R" group of the amino acid; (iii) one in which the mature polypeptide is fused with another compound, such as a compound to increase the half-life of the polypeptide (for example, polyethylene glycol), or (iv) one in which additional amino acids are fused to the mature polypeptide, such as an immunoglobulin Fc region peptide, a leader or secretory sequence, a sequence which is employed for purification of the mature polypeptide (such as GST) or a proprotein sequence. Such fragments, derivatives and analogs are intended to be encompassed by the present invention, and are within the scope of those skilled in the art from the teachings herein and the state of the art at the time of invention.

The polypeptides of the present invention are preferably provided in an isolated form, and preferably are substantially purified. A recombinantly produced version of the tag7 polypeptide can be substantially purified by the one-step method described in Smith and Johnson, Gene 67:31–40 (1988). As used herein, the term "substantially purified" means a preparation of tag7 polypeptide wherein at least 50%, preferably at least 70%, and more preferably at least 80%, 85%, 90%, 91%, 92%, 93%, 94%, 95%, 96%, 97%, 98% or 99% of contaminating proteins (i.e., those that are not tag7 proteins) have been removed from the preparation.

The polypeptides of the present invention include those which are at least about 65% identical, more preferably at least about 70%, at least about 75%, at least about 80%, at least about 85%, at least about 90%, at least about 95%, at least about 96%, at least about 97%, at least about 98% or at least about 99% identical, to the polypeptide encoded by a polynucleotide having a nucleic acid sequence as set forth in FIG. 1 (SEQ ID NO:1) or in SEQ ID NO: 3, to the polypeptide having the complete amino acid sequence shown in FIG. 1 (SEQ ID NO:2), or in SEQ ID NO: 4, to the mature tag7 polypeptide having the amino acid sequence set forth at positions about 20–182 in FIG. 1 (SEQ ID NO:2), to a polypeptide encoded by a polynucleotide hybridizing under stringent conditions to a polynucleotide having the nucleotide sequence set forth in SEQ ID NO:1, or to a polypeptide encoded by a polynucleotide hybridizing under defined conditions to a polynucleotide having the nucleotide sequence set forth in SEQ ID NO:1. The present polypeptides also include portions or fragments of the above-described polypeptides with at least 30 amino acids and more preferably at least 50 amino acids.

By a polypeptide having an amino acid sequence at least, for example, 65% "identical" to a reference amino acid sequence of a tag7 polypeptide is intended that the amino acid sequence of the polypeptide is identical to the reference sequence except that the polypeptide sequence may include up to 35 amino acid alterations per each 100 amino acids of the reference amino acid of the tag7 polypeptide. In other words, to obtain a polypeptide having an amino acid sequence at least 65% identical to a reference amino acid sequence, up to 35% of the amino acid residues in the reference sequence may be deleted or substituted with another amino acid, or a number of amino acids up to 35% of the total amino acid residues in the reference sequence may be inserted into the reference sequence. These alterations of the reference sequence may occur at the amino (N-) or carboxy (C-) terminal positions of the reference amino acid sequence or anywhere between those terminal positions, interspersed either individually among residues in the reference sequence or in one or more contiguous groups within the reference sequence.

The polypeptides of the present invention can be used as molecular weight markers on SDS-PAGE gels or on molecular sieve gel filtration columns using methods well known to those of skill in the art. In addition, as described in detail below, the polypeptides of the present invention can be used to raise polyclonal and monoclonal antibodies which are useful in assays for detecting tag7 protein expression, as antagonists capable of inhibiting tag7 protein function, in therapeutic approaches to inhibiting or delaying the metastasis of a tumor, or for the isolation of tag7 protein.

In another aspect, the present invention provides a peptide or polypeptide comprising an epitope-bearing portion of a polypeptide of the invention, which may be used to raise antibodies, particularly monoclonal antibodies, that bind specifically to a tag7 polypeptide of the invention. The epitope of this polypeptide portion is an immunogenic or antigenic epitope of a polypeptide of the invention. An "immunogenic epitope" is defined as a part of a protein that elicits an antibody response when the whole protein is the inmmunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes (see, e.g., Geysen et al., *Proc. Natl. Acad. Sci. USA* 81:3998–4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, e.g., Sutcliffe, J. G., et al., *Science* 219:660–666 (1983)). Peptides capable of eliciting protein-reactive sera are frequently represented in the primary sequence of a protein, can be characterized by a set of simple chemical rules, and are not confined to the immunodominant regions of intact proteins (i.e., immunogenic epitopes) or to the amino or carboxy termini. Peptides that are extremely hydrophobic and those of six or fewer residues generally are ineffective at inducing antibodies that bind to the mimicked protein; longer peptides, especially those containing proline residues, usually are effective (Sutcliffe, J. G., et al., *Science* 219:660–666 (1983)).

Epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); sequences containing proline residues are particularly preferred.

Non-limiting examples of epitope-bearing polypeptides or peptides that can be used to generate tag7-specific antibodies include a polypeptide having an amino acid sequence consisting essentially of amino acid residues from about 20 to about 40 in FIG. 1 (SEQ ID NO:2), a polypeptide having an amino acid sequence consisting essentially of amino acid residues from about 55 to about 75 in FIG. 1 (SEQ MD NO:2), a polypeptide having an amino acid sequence consisting essentially of amino acid residues from about 90 to about 110 in FIG. 1 (SEQ ID NO:2), and a polypeptide having an amino acid sequence consisting essentially of amino acid residues from about 145 to about 160 in FIG. 1 (SEQ ID NO:2). Other epitope-bearing polypeptides or peptides that may be used to generate tag7-specific antibodies will be apparent to one of ordinary skill in the art based on the hydrophilicity plot of the tag7 polypeptide shown in FIG. 2.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis (see, e.g., U.S. Pat. No. 4,631,211; Houghten, R. A., *Proc. Natl. Acad. Sci. USA* 82:5131–5135 (1985)).

As one of skill in the art will appreciate, tag7 polypeptides of the present invention and epitope-bearing fragments thereof may be immobilized onto a solid support, by techniques that are well-known and routine in the art. By "solid support" is intended any solid support to which a peptide can be immobilized. Such solid supports include, but are not limited to nitrocellulose, diazocellulose, glass, polystyrene, polyvinylchloride, polypropylene, polyethylene, dextran, Sepharose, agar, starch, nylon, beads and microtitre plates. Linkage of the peptide of the invention to a solid support can be accomplished by attaching one or both ends of the peptide to the support. Attachment may also be made at one or more internal sites in the peptide. Multiple attachments (both internal and at the ends of the peptide) may also be used according to the invention. Attachment can be via an amino acid linkage group such as a primary amino group, a carboxyl group, or a sulfhydryl (SH) group or by chemical linkage groups such as with cyanogen bromide (CNBr) linkage through a spacer. For non-covalent attachments, addition of an affinity tag sequence to the peptide can be used such as GST (Smith, D. B., and Johnson, K. S., *Gene* 67:31 (1988)), polyhistidines (Hochuli, E., et al., *J. Chromatog.* 411:77 (1987)), or biotin. Such affinity tags may be used for the reversible attachment of the peptide to the support. Such immobilized polypeptides or fragments may be useful, for example, in isolating antibodies directed against tag7, as described below.

As one of skill in the art will also appreciate, tag7 polypeptides of the present invention and the epitope-bearing fragments thereof described above can be combined with parts of the constant domain of immunoglobulins (Ig), resulting in chimeric or fusion polypeptides. These fusion polypeptides facilitate purification and show an increased half-life in vivo EP 0 394 827; Traunecker et al., *Nature* 331:84–86 (1988)).

Anti-tag7 Antibodies

Epitope-bearing peptides and tag7 polypeptides of the invention may be used to produce antibodies directed against tag7 according to methods well-known in the art. See, for instance, Sutcliffe, J. G., et al., *Science* 219:660–666 (1983); Wilson et al., *Cell* 37:767 (1984); and Bittle, F. J., et al., *J. Gen. Virol.* 66:2347–2354 (1985). Antibodies specific for tag7 can be raised against the intact tag7 polypeptide or one or more antigenic polypeptide fragments thereof, such as the epitope-bearing fragments of tag7 described above. These polypeptides or fragments may be presented together with a carrier protein (e.g., albumin) to an animal system (such as rabbit or mouse) or, if they are long enough (at least about 25 amino acids), without a carrier.

As used herein, the term "antibody" (Ab) may be used interchangeably with the terms "polyclonal antibody" or "monoclonal antibody" (mAb), except in specific contexts as described below. These terms, as used herein, are meant to include intact molecules as well as antibody fragments (such as, for example, Fab and F(ab')$_2$ fragments) which are capable of specifically binding to tag7 polypeptide or a portion thereof. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

The antibodies of the present invention may be polyclonal or monoclonal, and may be prepared by any of a variety of methods. For example, polyclonal antibodies may be made by immunizing an animal with one or more of the tag7 polypeptides or portions thereof (including one or more tag7 epitope-bearing fragments) of the invention according to standard techniques (see, e.g., Harlow, E., and Lane, D., *Antibodies: A Laboratory Manual*, Cold Spring Harbor, N.Y.: Cold Spring Harbor Laboratory Press (1988); Kaufinan, P. B., et al., In: *Handbook of Molecular and Cellular Methods in Biology and Medicine*, Boca Raton, Fla.: CRC Press, pp. 468–469 (1995)). In the most preferred method, the antibodies of the present invention are monoclonal antibodies (or tag7 protein-binding fragments thereof). Such monoclonal antibodies can be prepared using hybridoma technology that is well-known in the art (Köhler et al., *Nature* 256:495 (1975); Köhler et al., *Eur. J. Immunol.* 6:511 (1976); Köhler et al., *Eur. J. Immunol.* 6:292 (1976); Hammerling et al., In: *Monoclonal Antibodies and T-Cell Hybridomas*, New York: Elsevier, pp. 563–681 (1981); Kaufman, P. B., et al., In: *Handbook of Molecular and Cellular Methods in Biology and Medicine*, Boca Raton, Fla.: CRC Press, pp. 444–467 (1995)).

Alternatively, antibodies capable of binding to tag7 polypeptides or fragments thereof may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, tag7 polypeptide-specific antibodies are used to immunize an animal, preferably a mouse. The splenocytes of such an animal are then used to produce hybridoma cells, and the hybridoma cells are screened to identify clones which produce an antibody whose ability to bind to the tag7 polypeptide-specific antibody can be blocked by the tag7 polypeptide antigen Such antibodies comprise anti-idiotypic antibodies to the tag7 polypeptide-specific antibody and can be used to immunize an animal to induce formation of further tag7 polypeptide-specific antibodies.

In another preferred embodiment of the invention, the present antibodies may be prepared as chimeric antibodies. According to the invention, such chimeric antibodies may comprise an antigen-binding domain (i.e., the region of the antibody binding to tag7) from a first species and one or more constant regions from a second species. See U.S. Pat. No. 4,816,567, which is directed to methods for the preparation of chimeric antibodies, the disclosure of which is incorporated herein by reference in its entirety.

It will be appreciated that Fab, F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, tag7 protein-binding fragments can be produced through the application of recombinant DNA technology or through synthetic chemistry.

The tag7 protein-specific antibodies of the present invention may be detectably labeled, most preferably with an enzyme, radioisotopic, non-radioactive isotopic, fluorescent, toxin, chemiluminescent or nuclear magnetic resonance (NMR) contrast agent label. Suitable examples of each of these types of labels are well-known to one of ordinary skill in the art. Typical techniques for binding a label to an antibody are provided, for example, by Kennedy et al., *Clin. Chim. Acta* 70:1–31 (1976), and Schurs et al., *Clin. Chim. Acta* 81:1–40 (1977), all of which methods are incorporated by reference herein.

In an additional preferred embodiment of the invention, the antibodies produced as described above may be covalently or non-covalently immobilized onto a solid support By "solid support" is intended any solid support to which an antibody can be immobilized, including but not limited to nitrocellulose, diazocellulose, glass, polystyrene, polyvinylchloride, polypropylene, polyethylene, dextran Sepharose, agar, starch, nylon, beads (including glass, latex, magnetic (including paramagnetic and superparamagetic) beads) and microtitre plates. Linkage of the antibodies of the invention to a solid support can be accomplished by attaching one or more ends of the antibody to the support. Attachment may also be made at one or more internal sites in the antibody. Multiple attachments (both internal and at the ends of the antibody) may also be used according to the invention. Attachment can be via an amino acid linkage group such as a primary amino group, a carboxyl group, or a sulfhydryl (SH) group or by chemical linkage groups such as with cyanogen bromide (CNBr) linkage through a spacer. For non-covalent attachments, addition of an affinity tag sequence to the antibody can be used such as GST (Smith, D. B., and Johnson, K. S. *Gene* 67:31 (1988)); polyhistidines (Hochuli, E. et al., *J. Chromatog.* 411:77 (1987)); or biotin. Alternatively, an indirect coupling agent such as Protein A or Protein G (available commercially, e.g., from Sigma Chemical Co, St. Louis, Mo.) which binds to the Fc region of antibodies may be attached to the solid support and the antibodies of the invention attached thereto by simply incubating the antibodies with the solid support containing the immobilized Protein A or Protein G. Such affinity tags may be also used for the reversible attachment of the antibodies of the present invention to the support.

Uses

The isolated tag7 polynucleotides, polypeptides and antibodies of the invention are useful in a variety of methods, for example in industrial, clinical and research settings. Included among these uses are the use of the present anti-tag7 antibodies in the determination of tag7 expression or production by isolated cells or tissues, or by cells and tissues in an animal, according to standard immunological techniques that will be familiar to one of ordinary skill. In addition, the polynucleotides and polypeptides of the invention may be used in therapeutic methods for inhibiting the growth or progression of a tumor in an animal. Analogously, the present polynucleotides and polypeptides may be used in methods of treating a cancer in an animal (preferably a mammal such as a human) suffering from a cancer or a tumor.

Inhibition of Tumor and Cancer Cell Growth

The present tag7 polynucleotides and polypeptides may be used in methods, provided by the invention, for inhibiting the growth of a tumor or cancer cell. In one preferred such aspect, the polynucleotides and polypeptides of the invention may be used to induce apoptosis in tumor or cancer cells. It will be understood by those of ordinary skill, however, that inhibition of growth of a cancer or tumor may proceed by cytostatic mechanisms (i.e., by inducing growth arrest or cell cycle arrest, including inducing differentiation, without actually killing the tumor or cancer cell) or cytocidal mechanisms (i.e. by inducing cell death, whether direct or indirect, including via induction of apoptosis, cytotoxicity, cytolysis, etc.).

Methods according to this aspect of the invention may comprise one or more steps which are designed to inhibit the growth of a tumor cancer cell, whether in vitro, in vivo or ex vivo (i.e., in a tissue section removed from the body of an animal that may or may not be replaced into the animal following treatment to inhibit tumor cell growth). In one preferred such embodiment of the invention, one or more isolated nucleic acid molecules comprising a polynucleotide encoding tag7 may be introduced into the tumor, or more preferably into a mammalian cell, to inhibit the growth of the tumor. Preferred nucleic acid molecules for use in this approach include a nucleic acid molecule comprising a polynucleotide having a nucleic acid sequence at least about 65% identical, or more preferably at least about 70%, 75%, 80%, 85%, 90%, 95% or 99% identical, to a reference sequence such as (a) the nucleotide sequence set forth in SEQ ID NO:1; (b) a nucleotide sequence encoding a tag7 polypeptide having the complete amino acid sequence set forth in SEQ ID NO:2; (c) a nucleotide sequence encoding a mature tag7 polypeptide having the amino acid sequence at positions about 20 to about 182 in SEQ ID NO:2; (d) the nucleotide sequence of a polynucleotide hybridizing under stringent conditions to a polynucleotide having a nucleotide sequence as set forth in SEQ ID NO:1; or (e) the nucleotide sequence of a polynucleotide hybridizing under defined conditions to a polynucleotide having a nucleotide sequence as set forth in SEQ ID NO:1. Particularly preferred are such nucleic acid molecules wherein the introduction of the nucleic acid molecule into the mammalian cell inhibits the growth of the tumor. In a particularly preferred embodiment, this approach includes a nucleic acid molecule comprising a polynucleotide having a nucleic acid sequence as set forth in SEQ ID NO:3; or (b) a nucleotide sequence encoding a tag7 polypeptide having the amino acid sequence set forth in SEQ ID NO:4.

In such an approach, one or more of the above-described isolated nucleic acid molecules may be incorporated into a vector or virion suitable for introducing the nucleic acid molecule into cells of the mammal to be treated, to form a transfection vector. Suitable vectors or virions for this purpose include those derived from retroviruses, adenoviruses and adeno-associated viruses. Techniques for the formation of the transfection vector comprising the tag7-encoding nucleic acid molecule are well-known in the art, and are generally described in "Working Toward Human Gene Therapy," Chapter 28 in *Recombinant DNA, 2nd Ed.*, Watson, J. D. et al., eds., New York: Scientific American Books, pp. 567–581 (1992), and in the references cited therein. Other suitable techniques for introducing tag7-encoding nucleic acid molecules are non-viral gene transfer techniques well known in the art, such as methods based on receptor-mediated endocytosis, as disclosed in WO 93/07283, liposomes, cationic lipids, etc. In an alternative approach, the isolated nucleic acid molecules may be introduced into the cell by other methods which will be familiar to one of ordinary skill in the art, including for example electroporation, transduction, transformation, calcium phosphate treatment, "gene gun", hypotonic poration and resealing, and the lice. By undertaking the above-described approaches, the level of tag7 protein expression is increased in the cell being treated, thereby inhibiting the growth of the tumor or inducing apoptosis in the tumor cells.

In another preferred method of the invention, a mammalian tumor may be inhibited from growing by being contacted with a composition comprising one or more of the above-described isolated tag7 polypeptides of the invention. Suitable isolated tag7 polypeptides for use in this aspect of the invention include those having an amino acid sequence at least about 65%, more preferably at least about 70%, 75%, 80%, 85%, 90%, 95% or 99%, identical to a reference sequence such as (a) the amino acid sequence encoded by an isolated nucleic acid molecule having a nucleotide sequence as set forth in SEQ ID NO:1; (b) the complete amino acid sequence of the tag7 polypeptide as set forth in SEQ ID NO:2; (c) the amino acid sequence of the mature tag7 polypeptide having the amino acid sequence as set forth at positions about 20 to about 182 in SEQ ID NO:2; (d) the amino acid sequence of a polypeptide encoded by a polynucleotide hybridizing under stringent hybridization conditions to a polynucleotide having the nucleotide sequence set forth in SEQ ID NO:1; or (e) the amino acid sequence of a polypeptide encoded by a polynucleotide hybridizing under defined hybridization conditions to a polynucleotide having the nucleotide sequence set forth in SEQ ID NO:1. Alternatively, these methods of the invention may advantageously use a fragment of one or more of the polypeptides described in (a), (b), (c), (d) or (e) above. Particularly preferred for use in the present methods are such tag7 polypeptides or fragments thereof wherein contacting the mammalian cell with the polypeptide or fragment inhibits the growth of the tumor.

In a preferred embodiment, the isolated tag7 polypeptides for use in this aspect of the invention include those having an amino acid sequence encoded by an isolated nucleic acid molecule having a nucleotide sequence as set forth in SEQ ID NO:3 or (b) the amino acid sequence of the tag7 polypeptide as set forth in SEQ ID NO:4, or fragments thereof.

Compositions for use in this aspect of the invention may optionally further comprise one or more additional compounds, such as a pharmaceutically acceptable carrier or excipient suitable for use with the isolated tag7 polypeptides contained in the compositions. By a "pharmaceutically acceptable carrier or excipient" is meant a non-toxic solid, semisolid or liquid filler, diluent, encapsulating material or formulation auxiliary of any type. The carrier may also contain minor amounts of additives such as substances that enhance isotonicity and chemical stability, which are well-known in the pharmaceutical are. Thus, the invention also provides pharmaceutical compositions comprising one or more of the isolated tag7 polypeptides of the invention and a pharmaceutically acceptable carrier or excipient therefor.

By undertaking the above-described approach, the tag7 polypeptide acts directly (e.g., via a cell surface or intracellular receptor) or indirectly (e.g., via transmembrane signalling or by inducing the action of one or more second messengers) to inhibit the growth of, or induce apopotosis in, the mammalian cell.

Mammalian cells that may be treated according to the present methods in order to inhibit a tumor from growing, or to induce tumor cells to undergo apoptosis, include those obtained from any mammal, including but not limited to mice, rats, monkeys, sheep, cows, horses, dogs, cats, guinea pigs, rabbits, and most particularly humans. Although any mammalian cell may be inhibited from growing by the above-described methods, these methods are particularly well-suited to inhibit the growth of, or induce apoptosis in, tumor or other cancer cells. Included among the types of tumor or cancer cells that are advantageously inhibited from growing by the methods of the invention are carcinoma cells (particularly liver carcinoma cells, ovarian carcinoma cells, breast carcinoma cells, cervical carcinoma cells, lung carcinoma cells, prostatic carcinoma cells, gastric carcinoma cells, bladder carcinoma cells, testicular carcinoma cells, colorectal carcinoma cells, pancreatic carcinoma cells, oral cavity carcinoma cells, squamous cell carcinoma cells, head and neck carcinoma cells and teratocarcinoma cells), sarcoma cells particularly Kaposi's sarcoma cells, fibrosarcoma cells and osteosarcoma cells), melanoma cells and leukemia cells.

Therapeutic Uses

The isolated nucleic acid molecules and polypeptides of the invention may also be used therapeutically, for example in treating a cancer in an animal suffering therefrom. In such approaches, the goal of the therapy is to delay or inhibit the progression or growth of the cancer or tumor, to delay or inhibit the metastasis of the cancer or tumor, and/or to induce remission of the cancer or tumor.

*Gene Therapy.* In a first such aspect of the invention, the animal suffering from cancer may be treated by introducing into the animal one or more of the isolated nucleic acid molecules of the invention comprising a polynucleotide encoding a tag7 polypeptide or a fragment thereof particularly a polynucleotide that is 90% or 95% identical to one or more of the reference nucleotide sequences described above. This approach, known generically as "gene therapy," is designed to increase the level of tag7 gene expression in the cells making up the cancer or tumor and thereby to inhibit or delay the growth, progression or metastasis, or to induce the remission, of the tumor or cancer. Analogous gene therapy approaches have proven effective or to have promise in the treatment of other mammalian diseases such as cystic fibrosis (Drumm, M. L. et al., *Cell* 62:1227–1233 (1990); Gregory, R. J. et al., *Nature* 347:358–363 (1990); Rich, D. P. et al., *Nature* 347:358–363 (1990)), Gaucher disease (Sorge, J. et al., *Proc. Natl. Acad. Sci. USA* 84:906–909 (1987); Fink, J. K. et al., *Proc. Natl. Acad. Sci. USA* 87:2334–2338 (1990)), certain forms of hemophilia (Bontempo, F. A. et al., *Blood* 69:1721–1724 (1987); Palmer, T. D. et al., *Blood* 73:438–445 (1989); Axelrod, J. H. et al., *Proc. Natl. Acad. Sci. USA* 87:5173–5177 (1990); Armentano, D. et al., *Proc. Natl. Acad. Sci. USA* 87:6141–6145 (1990)) and muscular dystrophy (Partridge, T. A. et al., *Nature* 337:176–179 (1989); Law, P. K. et al., *Lancet* 336:114–115 (1990); Morgan, J. E. et al., *J. Cell Biol.* 111:2437–2449 (1990)), as well as in other treatments for certain cancers such as metastatic melanoma (Rosenberg, S. A. et al., *Science* 233:1318–1321 (1986); Rosenberg, S. A. et al., *N. Eng. J. Med.* 319:1676–1680 (1988); Rosenberg, S. A. et al., *N. Eng. J. Med.* 323:570–578 (1990)).

In a preferred such approach, one or more isolated nucleic acid molecules of the invention, comprising a polynucleotide having a nucleotide sequence at least 90% or at least 95% identical to the above-described reference nucleotide sequences, is introduced into or administered to the animal that is suffering from the cancer. Such isolated nucleic acid molecules may be incorporated into a vector or virion suitable for introducing the nucleic acid molecules into the cells or tissues of the animal to be treated, to form a transfection vector. Suitable vectors or virions for this purpose include those derived from retroviruses, adenoviruses and adeno-associated viruses. Alternatively, the nucleic acid molecules of the invention may be complexed into a molecular conjugate with a virus (e.g., an adenovirus or an adeno-associated virus) or with viral components (e.g., viral capsid proteins).

Techniques for the formation of vectors or virions comprising the tag7-encoding nucleic acid molecules are well-known in the art, and are generally described in "Working Toward Human Gene Therapy," Chapter 28 in *Recombinant DNA*, 2nd Ed., Watson, J. D. et al., eds., New York: Scientific American Books, pp. 567–581 (1992). In addition, general methods for construction of gene therapy vectors and the introduction thereof into affected animals for therapeutic purposes may be obtained in the above-referenced publications, the disclosures of which are specifically incorporated herein by reference in their entirety. In one such general method, vectors comprising the isolated polynucleotides of the present invention are directly introduced into the cells or tissues of the affected animal, preferably by injection, inhalation, ingestion or introduction into a mucous membrane via solution; such an approach is generally referred to as "in vivo" gene therapy. Alternatively, cells, tissues or organs, particularly those containing cancer cells or tumors, may be removed from the affected animal, and placed into culture according to methods that are well-known to one of ordinary skill in the art; the vectors comprising the tag7 polynucleotides may then be introduced into these cells or tissues by any of the methods described generally above for introducing isolated polynucleotides into a cell or tissue, and, after a sufficient amount of time to allow incorporation of the tag7 polynucleotides, the cells or tissues may then be re-inserted into an affected animal. Since the introduction of the tag7 gene is performed outside of the body of the affected animal, this approach is generally referred to as "ex vivo" gene therapy. One type of ex vivo gene therapy may also be referred to as "immunotherapy" or, more specifically "cancer vaccine". It elicits an immune response in the treated animal, thus eliminating the tumor cells. In the experiments of the present invention, it has been shown that vaccination of animals with tumor cells expressing tag7 protects the animals against a subsequent challenge with unmodified tumor cells. In a preferred embodiment, the present invention comprises a tumor vaccine based on tag7 expressing tumor cells. Such cells may be, as described above, autologous, i.e. derived from the individual to be treated, or they may be allogeneic, i.e. from one or more different individuals, e.g. cells from different established cell lines.

For both in vivo and ex vivo gene therapy, the isolated tag7 polynucleotides of the invention may alternatively be operatively linked to a regulatory DNA sequence, which may be a tag7 promoter or an enhancer, or a heterologous regulatory DNA sequence such as a promoter or enhancer derived from a different gene, cell or organism, to form a genetic construct as described above. This genetic construct may then be inserted into a vector, which is then directly introduced into the affected animal in an in vivo gene therapy approach, e.g., by intratumoral administration (i.e., introduction of the nucleic acid molecule or vector directly into a tumor in an animal, for example by injection), or into the cells or tissues of the affected animal in an ex vivo approach. In another preferred embodiment, the genetic construct of the invention may be introduced into the cells or tissues of the animal, either in vivo or ex vivo, in a molecular conjugate with a virus (e.g., an adenovirus or an adeno-associated virus) or viral components (e.g., viral capsid proteins; see WO 93/07283). Alternatively, transfected host cells, which may be homologous or heterologous, may be encapsulated within a semi-permeable barrier device and implanted into the affected animal, allowing passage of tag7 polypeptides into the tissues and circulation of the animal but preventing contact between the animal's immune system and the transfected cells (see WO 93/09222). These approaches result in increased production of tag7 by the treated animal via (a) random insertion of the tag7 gene into the host cell genome; or (b) incorporation of the tag7 gene into the nucleus of the cells where it may exist as an ertrachromosomal genetic element. General descriptions of such methods and approaches to gene therapy may be found, for example, in U.S. Pat. No. 5,578,461; WO 94/12650; and WO 93/09222.

Regardless of the approach used, however, use of these methods of the present invention will result in the increased production of tag7 by the cells and tissues of the treated animal, such that the cancer or tumor progression, growth or metastasis will be delayed or inhibited, or such that the cancer or tumor will go into remission or be cured.

Protein Therapy. In another preferred therapeutic approach provided by the present invention, an animal suffering from a cancer may be treated by administration of a composition comprising one or more of the isolated tag7 polypeptides of the invention to the affected animal, wherein such administration inhibits the progression, growth or metastasis, or induces the remission, of the cancer or tumor. In one such approach, the isolated tag7 polypeptides are administered to the animal in the form of the above-described pharmaceutical compositions. In another such approach, the compositions administered to the animal may comprise one or more of the isolated tag7 polypeptides having an amino acid sequence at least about 65%, or more preferably at least about 70%, 75%, 80%, 85%, 90%, 95% or 99%, identical to one or more of the above-described reference amino acid sequences. Thus, the invention further provides methods of treating an animal suffering from a cancer comprising administering to such an animal a pharmaceutical composition comprising a therapeutically effective amount of one or more isolated tag7 polypeptides of the invention and optionally a pharmaceutically acceptable carrier or excipient therefor.

The tag7 polypeptide-containing compositions should be formulated and dosed in a fashion consistent with good medical practice, taking into account the clinical condition of the individual patient (especially the side effects of treatment with tag7 polypeptide alone), the site of delivery of the tag7 polypeptide composition, the method of administrations the scheduling of administration, and other factors known to practitioners. The "therapeutically effective amount" of the tag7 polypeptide for purposes herein is thus determined by such considerations.

As a general proposition, the total therapeutically effective amount of tag7 polypeptide administered parenterally per dose will be in the range of about 0.01 $\mu$g/kg/day to about 1000 $\mu$g/kg/day of patient body weight, although, as noted above, this will be subject to therapeutic discretion. More preferably, this dose is at least 0.1 $\mu$g/kg/day, and most preferably for humans between about 0.1 and about 100 $\mu$g/kg/day for the polypeptide. If given continuously, the tag7 polypeptide may be administered either by 1–10 injections per day or by continuous subcutaneous infusion, for example, using a mini-pump. An intravenous bag solution may also be employed. The key factor in selecting an appropriate dose is the result obtained, as measured, for example, by increases in the circulating tag7 level or by determining a decrease in tumor growth or metastasis or in remission of the cancer. Other useful measures of determining therapeutic effectiveness are known to one of ordinary skill in the art. The length of treatment needed to observe changes, and the interval following treatment for responses to occur, may vary depending on the desired effect.

Pharmaceutical compositions for use in such methods comprise one or more of the isolated tag7 polypeptides of the present invention and may optionally comprise a pharmaceutically acceptable carrier or excipient therefor, as described above. The tag7 polypeptides, and the pharmaceutical compositions of the present invention, may be administered by any means that achieve their intended purpose of delaying or inhibiting the progression, growth or metastasis, or inducing the remission, of a cancer or a tumor in an affected animal. For example, administration may be by intratumoral, oral ocular, otical, rectal, parenteral, subcutaneous, intravenous, intramuscular, intraperitoneal, intravaginal, topical (as by powders, ointments, drops or transdermal patch), bucal, intrathecal or intracranial routes, as an oral or nasal spray or as ocular or intraotic drops. The term "parenteral" as used herein refers to modes of administration which include intravenous, intramuscular, intraperitoneal, intrasternal, subcutaneous and intraarticular injection and infusion. The dosage administered will be dependent upon the age, health, and weight of the recipient, kind of concurrent treatment, if any, frequency of treatment, and the nature of the effect desired. Compositions within the scope of the invention include all compositions wherein the tag7 polynucleotides or polypeptides are contained in an amount which is effective to achieve inhibition or delaying of the growth, progression or metastasis of a tumor or cancer, or the induction of remission or curing of the cancer or tumor. While individual needs may vary from one animal to another, determination of optimal ranges of effective amounts of each component is within the ability of the clinician of ordinary skill.

The tag7 polypeptide-containing compositions may also be administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919; EP 0 058 481), copolymers of L-glutamic acid and gamma-ethyl-L-glutamate (Sidman, U., et al., *Biopolymers* 22:547–556 (1983)), poly (2-hydroxyethyl methacrylate) (Langer, R., et al., *J. Biomed. Mat. Res.* 15:167–277 (1981); Langer, R., *Chem. Tech.* 12:98–105 (1982)), ethylene vinyl acetate (Langer et al., Id.) and poly-D(-)-3-hydroxybutyric acid (EP 0 133 988). Sustained-release tag7 polypeptide compositions may also include liposomally entrapped or absorbed tag7 polypeptides, which may be prepared by any of a variety of methods that have been well-described in the art (See U.S. Pat. Nos. 4,485,045 and 4,544,545; Epstein et al., *Proc. Natl. Acad. Sci.* (*USA*) 82:3688–3692 (1985); Hwang et al., *Proc. Natl. Acad. Sci.* (*USA*) 77:4030–4034 (1980); EP 0 036 676; EP 0 052 322; EP 0 088 046; EP 0 102 324; EP 0 142 641; EP 0 143 949; DE 3,218,121; and JP 83-118008).

For parenteral administration, in one embodiment, the tag7 polypeptides are formulated generally by mixing them at the desired degree of purity, in a unit dosage injectable form (solution, suspension, or emulsion), with a pharmaceutically acceptable carrier, Le, one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the tag7 polypeptides of the invention uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as are liposomes.

The tag7 polypeptide is typically formulated in such vehicles at a concentration of about 0.01 mg/ml to about 100 mg/ml, preferably about 0.1 to about 10 mg/ml, at a pH of about 3 to 8. It will be understood that the use of certain of the foregoing excipients, carriers, or stabilizers may result in the formation of tag7 polypeptide salts.

The tag7 polypeptides to be used for therapeutic administration must be sterile. Sterility is readily accomplished by filtration through sterile filtration membranes (e.g., 0.2 micron membranes) or by gamma or ultraviolet irradiation according to art-known techniques. Therapeutic tag7 polypeptide compositions generally are placed into a container having a sterile access port, for example, an intravenous solution bag or vial having a stopper pierceable by a hypodermic injection needle.

The therapeutic compositions comprising the tag7 polypeptides of the invention ordinarily may be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous tag7 polypeptide solution, and the resulting mixture is lyophilized. The infusion solution is prepared by reconstituting the lyophilized tag7 polypeptide using U.S.P. water that is suitable for injection.

A variety of cancers may be treated in animals by these therapeutic methods of the invention. Cancers suitably treated by these methods include, but are not limited to, carcinomas, sarcomas, melanomas and leukemias, particularly those described above. The methods of the invention are particularly well-suited for treating cancers in any animal, preferably in mammals and most particularly in humans.

It will be readily apparent to one of ordinary skill in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

General Discussion

To search for genes that are selectively expressed in tumors with high metastatic potential, a pair of tumors of identical origin and differing in their metastatic properties was chosen. Two substrains of the highly metastatic cancer VMR (which has a broad organ spectrum of metastasis and a frequency of metastasis to the liver no greater than 5%) were isolated in previous studies (Senin, V. M., *Vestn. Akad. Med. Nauk. SSSR* 0(5):85–91 (1984)): the VMR-0 line (frequency of metastasis to the liver of about 0%) and the VMR-L line (frequency of metastasis to the liver of about 100%). In contrast to the CSML-0 and CSML-100 tumor lines, none of these VMR tumors expresses the previously cloned mtsl gene which is transcribed in the majority of tumors (Grigorian, M. S., et al., *Genetika (USSR)* 25(6):993–1000 (1989)), making the search for other genes that participate in the process of metastasis reasonable. If one considers the tumors obtained in accordance with previously proposed models (Fidler, I. J., and Hart, I. R., *Science* 217:998–1001 (1982)), it is evident that the VMR-L tumor may derive from a metastatic subpopulation of cells which was present in the initial VMR tumor at a very low level and which had a relatively short life span (Kerbell, K. S., *Adv. Cancer Res.* 55:87–131 (1990)).

This probable similar origin of the pair of tumors studied here offers the possibility of using the "differential RNA display" technique to identify metastasis-associated genes. In gross, the genetic differences between the VMR-0 and VMR-L tumors were insignificant, confirming their common origin to a certain degree. Nevertheless, it was possible by means of this approach to isolate several fragments of DNA corresponding to differentially expressed RNAs in the VMR-0 and VMR-L tumors. Analysis of the isolated fragments using Northern hybridization with total RNA from these tumors made it possible to assign the majority of the fragments to the class of known repeat sequences (the IAR element, etc.). However, several of the fragments obtained could not be so assigned and were therefore of undoubted interest.

Figure 2:
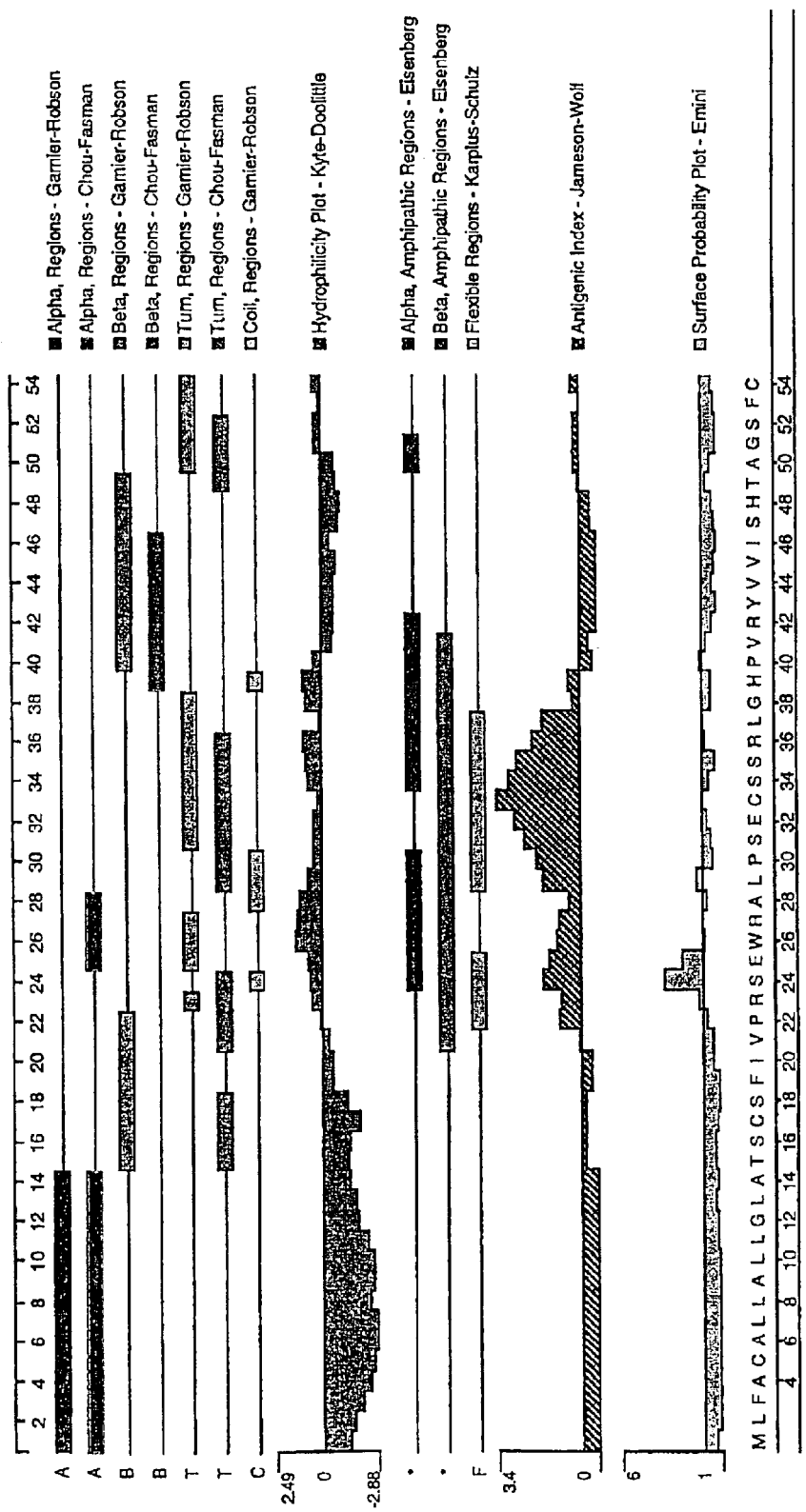
FIG. 2 is a composite graph of various structural characteristics of the tag7 polypeptide, indicating (based on the primary amino acid structure of the polypeptide): likely regions of alpha helix, beta sheet, beta turn and alpha coil structure; likely alpha and beta amphipathic regions; hydrophilicity of the polypeptide; antigenic index of the polypeptide; and probability of cell-surface localization of the polypeptide.
Figure 2:
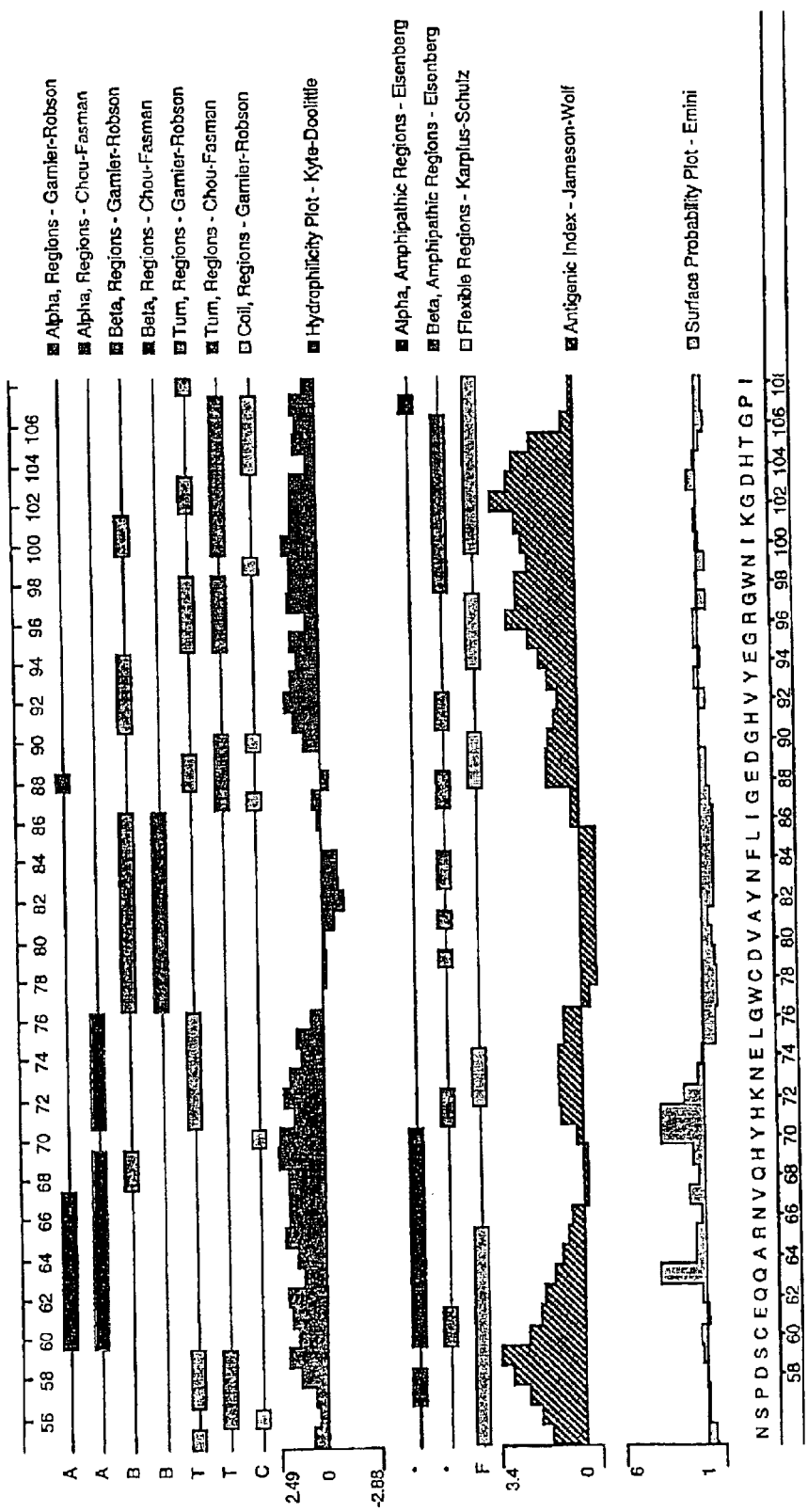
Figure 2:
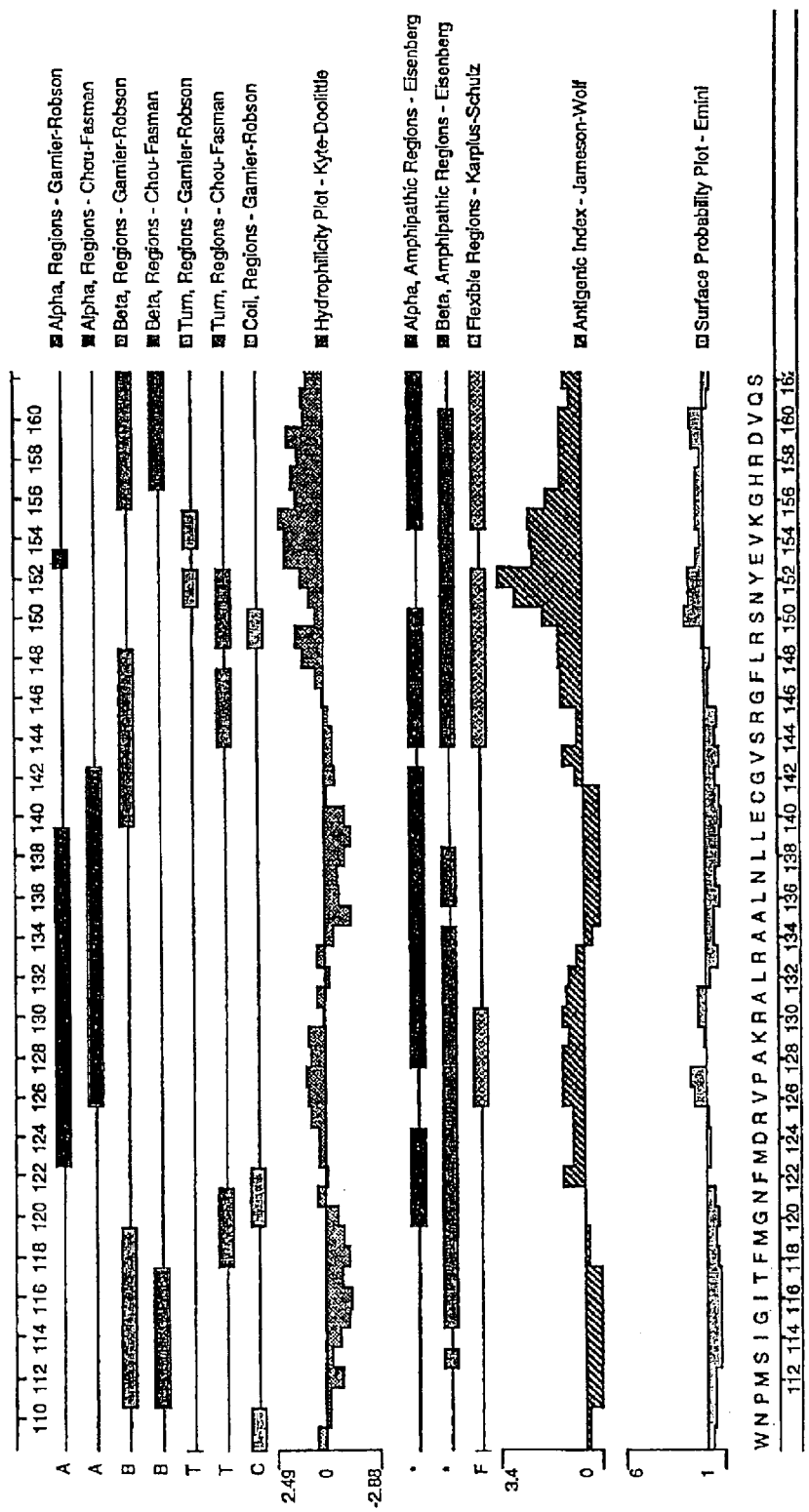
Figure 2:
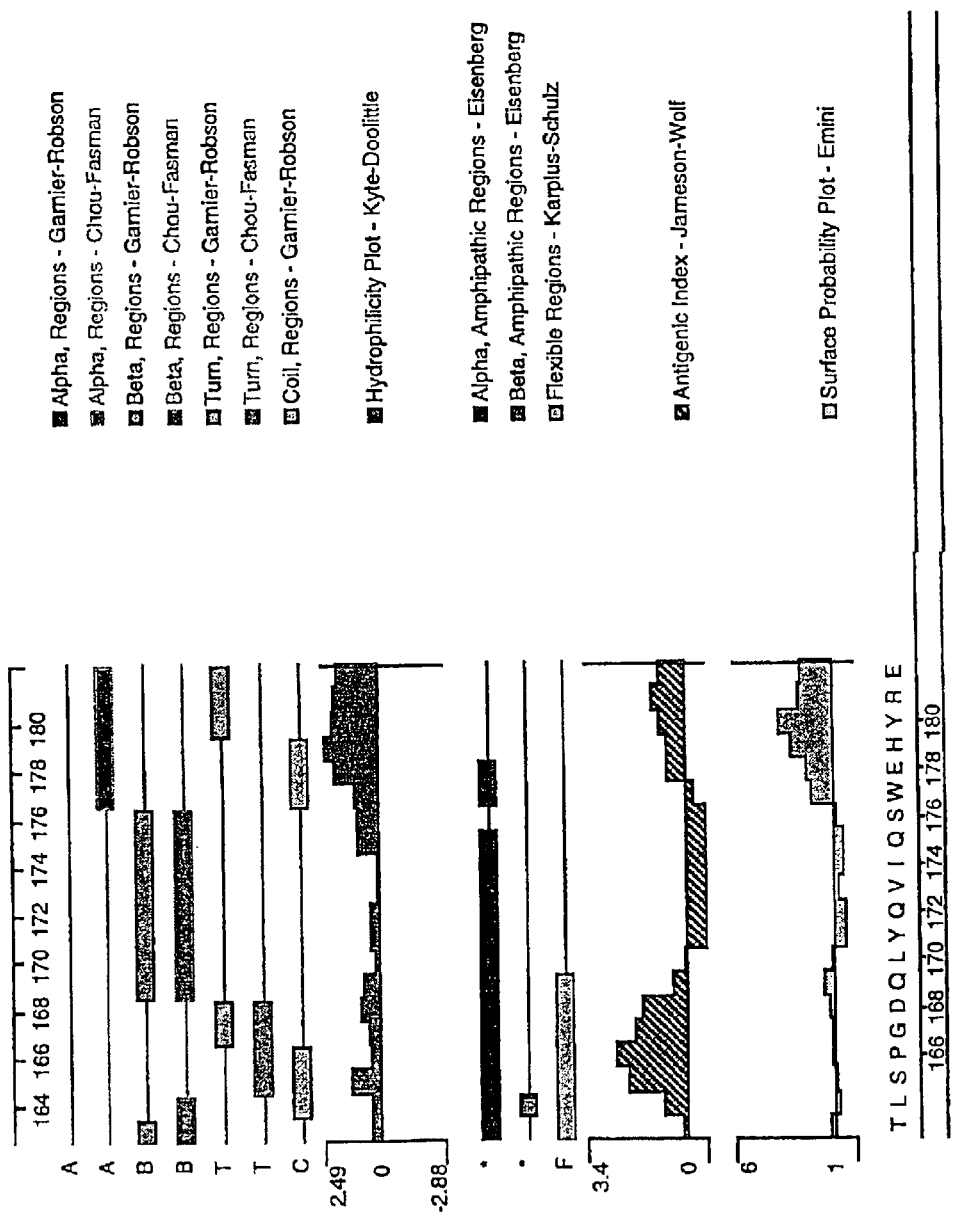

One such fragment isolated and characterized here is the tag 7 gene which exhibits a very high level of transcription in the liver-metastasizing VMR-L tumor (see FIG. 2). Sequence analysis showed that the PCR fragment was flanked on both sides by the 5' terminal primer 5'-AATCGGGCTG-3' (SEQ ID NO:6). When the nucleotide sequence of a cDNA clone from the total VMR-L cDNA library was analyzed, a sequence which is homologous to this primer over a length of eight bp was found at a distance of 52 nucleotides from the 3' poly A+ tail of the cloned cDNA. It is likely that the traditional oligo-dT primer could be used in the "differential RNA display" technique instead of the 3' terminal primer, and only the 5' terminal primers could be varied; such an approach would probably decrease the number of fragments obtained, but would simultaneously increase the resolving capacity of the gel.

Those errors which arise in the numerous cycles of the PCR may be classified as deficiencies of the technique. When the nucleotide sequence of the fragment obtained in the PCR and the cDNA of the tag7 clone were compared, it was found that 44 nucleotides at the 5' end of the amplified fragment do not coincide with the analogous segment of the sequence of the clone of the cDNA.

Computer analysis of the full-length sequence of the murine tag7 cDNA revealed two open reading frames (ORFs), corresponding to polypeptides of approximately 182 amino acids and 91 amino acids in length. Both translation starts satisfied the averaged Kozak sequence (Kozak, M., *J. Cell Biol.* 108:229–241 (1989)) to different degrees.

However, in the case of the longer ORF, the number of nucleotides coinciding with the translation consensus is greater than for the shorter ORF, and it is probably the first methionine in particular that is the site of translation initiation. In addition, the methionine in the +37 to +39 bp position of the full-length cDNA is closer to the 5' end, and consequently is more favorable for translation initiation (Kozak, M., *J. Cell Biol.* 108:229–241 (1989)). However, translation of a functional tag7 polypeptide could also be initiated from the second methionine.

The molecular weight of the predicted tag7 polypeptide (182 amino acid residues; SEQ ED NO:1) is about 20 KDa. In order to search for homologies with previously described sequences, the tag7 nucleotide sequence and the predicted amino acid sequence of its product were analyzed in the GENE and SWISSPROT data banks by means of the FASTA (Heidelberg, Germany) and BLAST (Washington, D.C., USA) homology-searching programs. No substantial homologies with previously known sequences were found, with the exception of an insignificant homology of a hydrophobic segment (between 2 and 12 amino acid residues), at the N-terminus of the predicted tag7 polypeptide, with the β chain of the human T-cell receptor. This hydrophobic region is also homologous to the signal sequences of some proteins (for example, the precursors of calreticulin, osteocalcin and extracellular globin III). The presence of a hydrophobic region at the N-terminus of the predicted tag7 polypeptide suggests that this polypeptide may have a transmembrane localization or may be secreted.

The expression of tag7 was not found to correlate with the organ-specificity of metastasis; the tag7 gene was transcribed not only in the cells of the liver-metastasizing VMR-L tumor, but also in the cells of the ovary-metastasizing VMR-Ov tumor. Among normal organs, the maximal level of expression of the tag7 gene was observed in the cells of those organs in which basal membrane cells have a high relative proportion. This correlation may not be purely coincidental, but may reflect the role that the basal membrane plays in the metastatic process (Stetler-Stevenson, W. G., et al., *Ann. Rev. Cell Biol.* 9:541–573 (1993)). It is interesting that the level of expression of the tag7 gene in metastasizing tumors is much higher than in the same cells in culture. This result is the converse of recently reported results from studies of gene expression in primary and cultured cancer cells (Zhang, L., et al., *Science* 276:1268–1271 (1997)), and may represent a response to the interaction of tumor cells with host cells of the basal membrane, for example in the process of the invasion of the basal membrane by metastatic tumor cells. The participation of cells of the stroma in regulating the expression of tag7, as occurs, for example, in stromelysin-3 gene expression (Basset, P., et al., *Nature* 348:699–704 (1990)), also cannot be excluded.

Also of interest is the observation that the level of transcription of the tag7 gene is several times lower in cells of the CSML-0 tumor than in VMR-L cells, whereas when strains of these same tumors are converted to culture, the picture changes markedly. Specifically, upon culturing these cells, the level of transcription of the tag7 gene in VMR-L cells declines, while it increases in CSML0 cells and exceeds by several-fold the level of tag7 expression in cultured VMR-L cells. A somewhat lower level tag7 transcription was observed in cultured MT1 TC1 cells in comparison to cultured CSML0 cells. Such a change in the level of transcription of the tag7 gene in cultured VMR-L cells may be explained by the fact that this culture is not monoclonal, and the proportion of the subpopulation of metastasizing cells in the culture therefore may be fairly low (Fidler, I. J., and Hart, I. R., *Science* 217:998–1001 (1982); Senin, V. M., *Vestn. Akad. Med. Nauk. SSSR* 0(5):85–91 (1984)). The heterogeneity of a culture CSML-0 cells, on the other hand, has been established by D. A. Kramer (personal communication). It is particularly interesting to note that the transcription of the tag7 gene was observed in cultures of cells of tumors which are of epithelial origin and have only low (5–10%) metastatic potential. However, of the 13 cell lines with varied metastatic properties that were investigated, only in cells of the VMR-L line did the transcription of the tag7 gene correlate with the marked metastatic potential of this tumor.

During the last decade a number of TNF-related cytokines have been identified and cloned. A proteolytically released form of TNF-α is a well-known soluble cytokine. In addition, the soluble form of the Fas ligand has been reported to be produced by activated peripheral T lymphocytes (Tanaka, M., et al., *EMBO J.* 14:1129–1135 (1995)) and a murine thymoma cell line was shown to secrete soluble CD40 ligand (Armitage, G., et al., *Eur. J. Immunol.* 22:2071–2076 (1992)). Due to its structural similarities with other TNF-related cytokines, tag7 may be a new member of this growing family.

The chromosome location of tag7 offers a possible insight into the in vivo role of tag7. Cytogenetic band 7A3 has been genetically linked with lupus-like nephritis in the MRL and New Zealand hybrid models of systemic lupus erythematosus (SLE) (Morel, L., et al., *Immunity* 1:219–229 (1994); Kono, D. H., et al., *Proc. Natl. Acad. Sci. USA* 91:10168–10172 (1994)). Although SLE is unlikely to involve mutations with severe functional alterations, gene knockout experiments may provide insight into the possible role of tag7 in this pathogenic process.

The localization of tag7 RNA essentially to the lymphoid organs is intriguing considering the cytotoxic effect of the soluble protein. It is evident that the main step in regulation cascade occurs at the posttranscriptional level. Even insignificant changes in tag7 mRNA production results in changes in the overall amount of protein synthesized and its secretion. It is therefore possible that differences in signaling capacity of the soluble versus the membrane-bound form of this ligand may be involved.

One of the biological activities of tag7 known from the present studies is its involvement in the in vitro induction of apoptosis in certain cell lines. Apoptosis or the process of programmed cell death is necessary for the normal development and homeostasis of an organism. Fragmentation of DNA into ~180 bp multimers is one of the changes that occurs during apoptosis.

Also of interest is the finding that VMR-0 tag7-transfected tumors grew significantly more slowly than did the parental VMR-0 tumors. A number of cytokines have been shown to be able to induce tumor rejection if produced locally by the tumor cell after gene transfer (Hock, H., et al., *Proc. Natl. Acad. Sci. USA* 90:2774–2778 (1993)). Different cytokines are known to activate heterogeneous transient tumor-suppressive mechanisms but always require CD8[+] cells for complete tumor rejection. Recently, a strong anti-tumor effect of human LT-α in a mouse experimental model has been described (Qin, Z., and Blankenstein, T., *Cancer Res.* 55:4747–4751 (1995)). A complex immunological mechanism which involves both T cells and B cells has been implicated in tumor rejection. LT-α was shown to be less toxic to animals than TNF and at least as effective as TNF (Qin, Z., et al., *Blood* 85:2779–2785 (1995)). No toxic effects of tag7-transfected cells were observed in mice, nor was any direct cytotoxic activity of clones transfected with tag7 construct detected in the L929 cytotoxic assay. Although tag7 activity in the conditioned medium of the clones was below the detection limit, the clone which produced lower amounts of tag7 RNA grew faster in syngeneic mice. A tumor-growth inhibitory effect of locally released tag7 is most likely indirect and can be reversed by injection of anti-tag7 antibodies. This was further supported by an experiment in which tumor growth of the parental VMR-0 line and co-injected 4SX cells was monitored. Even when twice the normal amount of cells was injected the rate of tumor growth was significantly reduced. Eventually, complete tumor reduction or remission could be achieved by higher amounts of tag7 secretion.

The inhibition of tumor cell growth mediated by tag7 does not seem to involve T lymphocytes, because in the absence of T cells (e.g., in nude mice) tag7-producing cells grew more slowly than in syngeneic mice (E. V. Korobko, unpublished observations). Despite these findings, however, the involvement of other cell types in the tag7-induced antitumor response cannot be ruled out.

Since gene transfer into tumor cells has been a valuable tool to assess the antitumor effect of various cytokines and antitumor, the antitumor effect of tag7 by introducing its cDNA into Tag7-negative tumor cells was investigated. A number of cytokines has been shown to be able to induce tumor rejection if produced locally by the tumor cell after gene transfer. Different cytokines activated heterogeneous transient tumor-suppressive mechanisms but always required CD8$^+$ cells for complete tumor rejection. Recently, a strong antitumor effect of human LT-α in mouse experimental model has been described. A complex immunological mechanism that involves T as well as B cell was implied in tumor rejection. LT-α was shown to be less toxic to animals than TNF and at least as effective as TNF. Tag7 was recently described as secreted by lymphocytes protein, cytotoxic for a limited number of target cells. In present invention, no toxic effects of Tag7 transfected cells in mice were detected. Moreover, the inventor were unable to detect direct cytotoxic activity of some clones transfected with Tag7 construct in L929 cytotoxic assay and had to relay on the level of Tag7 mRNA. Although Tag7 activity in the conditioned medium of the clones was below the detection limit, the clone that produced lower amounts of Tag7 RNA grew faster on syngenetic mice. A tumor-growth inhibitory effect of locally released Tag7 is indirect and was reversed by anti-Tag7 antibodies injection. This was further supported by an experiment in which tumor growth of parental VMR-0 and 4SX cells co-injected together was monitored. Even when doubled amount of cells was injected the rate of tumor growth was significantly reduced. Eventually, complete tumor rejection could be achieved by higher amounts of Tag7 secretion. Tumor rejection after co-implantation of parental and modified cells at the same site suggests that Tag7 effect is at least locally limited and is induced by some nonspecific host response that also rejects bystander tumor cells. However, transient expression of Tag7 in melanoma M3 cells established protective immunity in a distant site. These results suggest that the antitumor effect of Tag7 is not locally limited and induce some specific host response that also rejects remote tumor cells.

Although the inventors did not detect any differences in proliferation between parental VMR-0 and stably transfected clones in vitro, results of histological and electron microscopy showed significant reduction in proliferation of modified tumors mainly due to apoptosis of modified cells. Sensitivity of the tumor cells to Tag7 in vitro was not required for this since the tumor cells were resistant to the secreted Tag7 in culture. However, the data do not exclude the possibility that the tumor cells when grown in vivo were susceptible to the secreted Tag7.

Tag7-based tumor suppression seems not to involve T lymphocytes, because in the absence of T cells (e.g., in nude mice) Tag7 producing cells grew even with a lower rate than in syngenetic mice; thus T cells most likely were not essential for this inhibitory effect. Apparently it indicates that the mechanism involved may be efficient against tumors lacking tumor-specific rejection antigens and therefore may be useful for treating nonantigenic tumors.

Immunohistochemical analysis revealed that modified tumor cells attracted CD45R positive cells, presumably B lymphocytes, although growth rate in SCID mice (in the absence of B cells) showed only significant differences in comparison with T cell negative mice (nude). These results indicate that apparently Tag7 recruits B cells and activates their cytotoxic machinery leading to apoptosis of tumor cells. Induction of protective immunity by Tag7 suggests that the transfer of tag7 might be an effective therapeutic strategy.

Having fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

EXAMPLES

Materials and Methods

The following materials and methods were generally used in all of the Examples.

Tumors and Cell Lines

The metastasizing (VMR-L) and non-metastasizing (VMR-0) lines of mouse mammary gland cancer, were bred as transplants in A/Sn mice. In the case of VMR-0, the transplantation was done with tumor material; in the case of the VMR-L line, with cells from metastases from the liver. A tumor, 1 cm in diameter, developed at the injection site 2–3 weeks after the intramuscular injection of 5×10$^5$ cells. L929 cells were obtained from American Type Culture Collection (ATCC Number: CRL-2148; Rockville, Md.). Cells of the VMR-0, VMR-L, VMR-Lym (Senin, V. M., *Vestn. Akad. Med. Nauk. SSSR* 0(5):85–91 (1984)), CSML0, CSML-100 (Senin, V. M., et al. *Experim. Oncol. (USSR)* 5(63):35–39 (1983)), Line 1, LL Met, 10 T½, MT1, TC1, MT1 TC3 (Barnett, S. C., and Eccles, S. A., *Exp. Metast.* 2(1):15–36 (1984)), RAC 5E, RAC 34E, RAC 10P, RAC 311C (Sonnenberg, A., et al., *Cancer Res.* 46:5913–5922 (1986)) and L929 cell lines were grown in a 5% CO2 atmosphere in DMEM medium containing 10% fetal bovine serum (FBS) and 100 units/ml each of penicillin and streptomycin.

M3-mouse metastatic melanoma cell line (ATCC CCL 53.1): Cells were cultured at RPMI 1640 medium containing 5% FBS 100 u/ml penicillin, 100 u/ml streptomycin, 10 mM HEPES.

For in vivo studies, VMR-0 cells were transfected using DOTAP transfection reagent (Boehringer Mannheim) according to the manufacturer's recommendations. Cells were grown in medium containing G418 for two weeks before selection of individual clones.

Mouse splenocytes, thymocytes, monocytes and peritoneal macrophages were isolated as described previously (Klaus, G. G. B., *Lymphocytes: A Practical Approach*, Klaus, G. G. B., Ed., Oxford, UK: IRL Press, Chapter 1 (1988)). Cells were cultured in RPMI-1640 medium containing 5% FBS, 100 units/ml each of penicillin and streptomycin and 10 mM HEPES. In some studies, cells were activated by bacterial lipopolysaccharide (LPS) in serum-free medium for varying time periods.

LPS-stimulated VMR-0 and VMR-L cells and conditioned media were obtained as previously described (Sheehan, K. C., et al., *J. Immunol.* 142:3884–3893 (1989)). Briefly, VMR-L cells were treated with LPS (6 µg/ml) for 18 hrs at 37° C. in serum-free medium, and cell-free supernatants were purified by centrifugation and used for cytotoxic analysis or immunological studies.

Extraction of RNA

Total cell RNA was extracted by the guanidine isothiocyanate method (Chomczynski, P., and Sacchi N., *Anal. Biochem.* 162:156–159 (1987)). Polyadenylated mRNA was extracted by two chromatography cycles on oligo-(dT) cellulose (Maniatis, T., et al., *Molecular Cloning: A Laboratory Manual*, Cold Spring Harbor, N.Y.: Cold Spring Harbor Laboratory Press, p. 545 (1982)).

Removal of Chromosomal DNA from the RNA Preparations

Fifty micrograms of total RNA were incubated for 30 min at 37° C. with 10 units of DNase I and a buffer containing 10 mM TRIS-HCl, pH 8.3, 50 mM KCl, and 1.5 mM $MgCl_2$ in the presence of 10 units of human placental ribonuclease inhibitor.

Differential Display of mRNA

Differential display of mRNA was performed by the standard technique (Liang, P., and Pardee, A. B., *Science* 257:967–971 (1992)). Briefly, cDNA was obtained from 0.2 µg of mRNA by the reverse transcription reaction using the T12 AC primer (5'-TTTTTTTTTTTTAC-3') (SEQ ID NO:5) and Moloney Murine Leukemia Virus (M-MuLV) reverse transcriptase. T12AC and two short random 5' oligonucleotide primers (primer 1:5'-AATCGGGCTG-3' (SEQ ID NO:6); primer 2: 5'-AGTCAGCCAC-3' (SEQ ID NO:7)) were used as the 3' primers in two different combinations in the course of the polymerase chain reaction (PCR). Amplified cDNAs were separated by electrophoresis in 6% polyacrylamide gels containing 7 M urea.

Electrophoresis and Hybridization

The electrophoresis of RNA was performed in 1.2% agarose gel in the presence of 6% formaldehyde and 50 mM phosphate buffer (Maniatis, T., et al., *Molecular Cloning: A Laboratory Manual*, Cold Spring Harbor, N.Y.: Cold Spring Harbor Laboratory Press, p. 545 (1982)). Up to 20 µg of total RNA were applied to each lane. Following electrophoresis the RNA was blotted from the gels onto nylon filters (Hybond-N, Amersham, England) and probed by hybridization with $^{32}$P-labeled cDNAs (Southern, E. M., *J. Mol. Biol.* 98:503–517 (1975)). EcoRI/XhoI fragments from the longest cDNA clone were labeled by random priming with the Random Primed Labeling kit (Boehringer Mannheim, Austria) according to manufacturer's instructions and used as hybridization probes. To equalize the amount of RNA loaded on each lane, hybridization with GAPDH DNA probe was performed. Hybridization was performed as described (Maniatis, T., et al., *Molecular cloning: A Laboratory Manual*, Cold Spring Harbor, N.Y.: Cold Spring Harbor Laboratory Press, p. 545 (1982)).

For hybridization of tag7 to human tissues, a Human Immune System Multiple Tissue Northern™ Blot II (Clontech) was probed with the $^{32}$P-labeled tag7 cDNA prepared as described above. The blot contained approximately 2 µg of polyA+ RNA per lane from the following human tissues: spleen, lymph node, thymus, peripheral blood leukocytes, bone marrow and fetal liver. The blot was then hybridized under defined hybridization conditions as follows: the blot was prehybridized at 65° C. for two hours in Church buffer (0.5 M sodium phosphate (pH 7.2), 7% SDS, 1 mM EDTA); probe was denatured at 95° C. for five minutes and added to 7 ml of fresh Church buffer for hybridization; hybridization was performed at 55° C., and the blot was washed three times at 50° C. for 15 minutes each in Church wash buffer (40 mM sodium phosphate (pH 7.2), 1% SDS). Blots were then exposed to x-ray film for 24 hours.

Cloning and Determination of the Nucleotide Sequence of cDNA Fragments

The amplified PCR products were cloned into the pGEM-T vector (Promega, USA). The nucleotide sequence was determined by the Sanger technique (Sanger, F., et al., *Proc. Natl. Acad. Sci. USA* 74:5463–5467 (1977)), and automatically using an Automated Sequenator (Applied Biosystems) according to the manufacturer's suggested protocols.

Construction of the cDNA Library

Double-stranded cDNA was synthesized on poly(A)$^+$ RNA isolated from VMR-L tumors using ZAP-cDNA Gigapack Cloning kit (Stratagene) in accordance with the manufacturer's recommendations, and was cloned into the λ ZAP vector at the EcoRI and XhoI sites. A cDNA fragment of 390 bp was used as probe for Northern hybridization and screening of the library was performed following standard techniques (Maniatis, T., et al., *Molecular Cloning: A Laboratory Manual*, Cold Spring Harbor, N.Y.: Cold Spring Harbor Laboratory Press, p. 545 (1982)). Positive clones were purified and the inserts excised as pBluescript clones using helper phage as described by the manufacturer. Some clones were sequenced using Sequenase Version 2.0 sequencing kit (USB-Amersham) and synthetic oligonucleotide primers (Applied Biosystems 391 DNA Synthesizer). A genomic library was constructed in the λ FIX II vector (Stratagene) and screened according to standard procedures (Sambrook, J., et al., *Molecular Cloning: A Laboratory Manual*, 2nd Ed., Cold Spring Harbor, N.Y.: Cold Spring Harbor Laboratory Press (1989)). The inserts were subcloned in the pGEM7Z vector and partially sequenced as described above.

Oligonucleotides were synthesized corresponding to the 5' and 3' ends of the coding regions of the mouse tag7 gene with BamHI and HindIII restriction sites appended to the ends of oligonucleotides. The coding region of the gene was amplified by standard PCR techniques, cut with BamHI and HindIII, and inserted in frame into the BamHI and HindIII sites of the pQES30 expression vector (Qiagen).

The full size tag7 cDNA fragment was cut out from the pBluescript clone with XbaI and XhoI restriction enzymes and subcloned in the pBK-CMV mammalian expression vector (Stratagene) into the NheI and XhoI sites.

Chromosomal Mapping of the Tag7 gene

Fluorescent in situ hybridization on mouse metaphase chromosomes was performed commercially by Genome Systems, Inc. (St. Louis, Mo.).

Immunological Methods

E. coli-produced recombinant tag7 (rtag7) protein was expressed in M15[pREP4] (Qiagen) and purified on Ni-NTA agarose (Qiagen) as recommended by the manufacturer. Rabbit antibodies raised against rtag7 were affinity purified on a Sepharose (Pharmacia; Piscataway, N.J.) column containing rtag7 immobilized as recommended by the manufacturer. SDS-polyacrylamide gel electrophoresis, immunoprecipitation, and immunoblotting were performed according to standard procedures (Sambrook, J., et al., *Molecular Cloning: A Laboratory Manual*, 2nd Ed., Cold Spring Harbor, N.Y.: Cold Spring Harbor Laboratory Press (1989)).

Tag7 Cytotoxicity Assay and Neutralization of Cytotoxic Activity

As a source of the native form of the rag7 protein, the culture medium conditioned by LPS-stimulated VMR-L cells was used. L929 cells were cultured in 96-well plates at a density of $3 \times 10^4$ cells per well. After overnight incubation, cells were treated with actinomycin D (1 µg/ml) for two hours at 37° C. in serum-free medium. After that, 100 µl per well of the LPS-stimulated VMR-L conditioned medium or LPS-containing medium were added. Where indicated, recombinant human tumor necrosis factor-α (rhTNF; Sigma) was added at a concentration 100 ng/ml in a volume 100 µl per well. To determine cell death, a CytoTox 96 Assay kit (Promega) was used or cells were stained with trypan blue and the coded samples were counted microscopically in a blinded fashion with a minimum of 100 cells scored for each group.

Neutralization of the cytotoxic effect of the tag7 protein or rhTNF was performed using affinity purified polyclonal rabbit anti-tag7 and polyclonal anti-hTNF (Sigma) antibodies. Polyclonal antibodies were added to the LPS-induced VMR-L conditioned medium at a final concentration of 2 µg/ml and the cytotoxic effect was determined as described above.

DNA Fragmentation Analysis

DNA fragmentation analysis was performed as described (Tian, Q., et al., *Cell* 67:629–639 (1991)) with modifications. Briefly, $2 \times 10^6$ L929 cells were preincubated with actinomycin D (1 µg/ml) for two hours at 37° C. in serum-free medium and subsequently incubated with LPS-induced VMR-L conditioned medium or with rhTNF for five hours. Cell were harvested and lysed in 20 mM Tris-HCl (pH 8.0), 10 mM EDTA (TE buffer) containing 0.8% Triton X-100. After centrifugation, DNA from supernatants was precipitated at −20° C. with isopropanol in the presence of NaCl. Precipitated DNA was resuspended in TE buffer, treated with RNase A and fragments were resolved by electrophoresis on 1.8% agarose gels in TE buffer.

Animal Studies

For studies of the effects of tag7 on in vivo tumor progression, six- to ten- week-old A/Sn mice were used. Exponentially growing cells were harvested, washed in PBS and injected subcutaneously into the dorsal region of mice in a volume of 0.2 ml PBS. Tumor size was measured in millimeters using a caliper and was recorded as described (Hock, H., et al., *Proc. Natl. Acad. Sci. USA* 90: 2774–2778 (1993)). To neutral the tag7 activity in vivo, 100 µg of anti-tag7 affinity purified antibodies were injected subcutaneously, together with $10^6$ tumor cells, on day 0 and then the same amount of antibodies was injected at the tumor site in 0.2 ml PBS on days 2, 4, 6, and 8. Control animals were injected with PBS alone on the same days.

Example 1

Identification of Genes Differentially Expressed in Tumors with Differing Metastatic Potential The "differential RNA display" technique (Liang, P., and Pardee, A. B., *Science* 257:967–971 (1992)) was used in the present study to identify genes with a different level of expression in two related lines of tumors differing in their metastatic characteristics.

Figure 3:
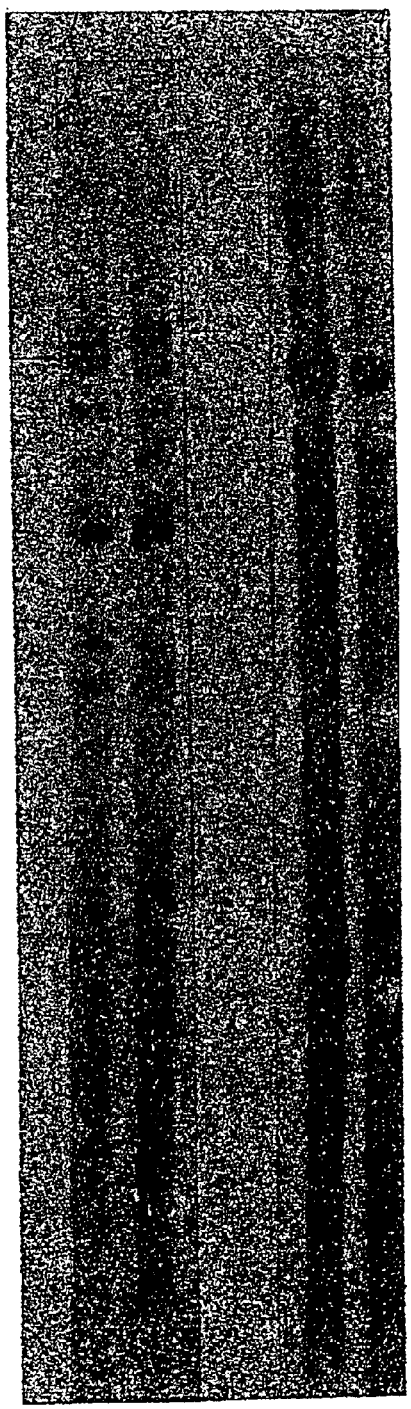
FIG. 3 is an autoradiograph comparing the results of differential display analysis of mRNA of non-metastasizing VMR-0 tumor cells (lanes 1, 3) and liver-metastasizing VMR-L tumor cells (lanes 2, 4). The cDNAs were obtained from 0.2 mg of RNA by reverse transcription with Moloney Murine Leukemia Virus (M-MuLV) reverse transcriptase in the presence of the T12AC primer (5'-TTTTTTTTTTTAC-3') (SEQ ID NO:5) and two different 10-base oligonucleotide primers: 5'-AATCGGGCTG-3' (SEQ ID NO:6; lanes 1, 2); and 5'-AGTCAGCCAC-3' (SEQ ID NO:7; lanes 3,4). Differences in the mRNA populations between the two different cell types are indicated by arrows.
Figure 4:
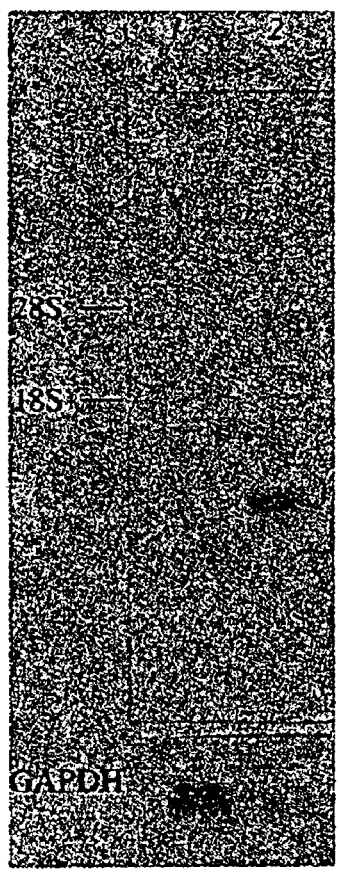
FIG. 4 is an autoradiograph of a Northern blot hybridization of reamplified cDNA samples of rag7 with total RNA obtained from VMR-0 tumor cells (lane 1) and VMR-L tumor cells (lane 2). The relative amount of material in each lane was evaluated from the intensity of the hybridization signal from the cDNA of the gene of glyceraldehyde-3-phosphate dehydrogenase (GAPDH).

The spectrum of cDNA fragments expressed in mouse tumors that are non-metastasizing (VMR-0) and that metastasize to the liver (VMR-L), obtained by the "differential RNA display" technique, is shown in FIG. 3. The spectrum of cDNA fragments amplified in the presence of the same pair of primers was found to be essentially identical for both tumor lines. However, when a large number of combinations of primers was analyzed it was possible to identify differences in the expression of some RNA sequences (FIG. 3, arrows). DNA fragments which had no analogs in the neighboring lane were eluted from the gel, amplified in the presence of the same pair of primers and cloned. Differences in the levels of expression of the RNA sequences in the two tumor lines analyzed were examined by means of Northern hybridization of the cloned fragments with total RNA from the two tumors. Two fragments that hybridized differentially to RNA from VMR-0 cells versus that from VMR-Liv cells were obtained as a result of this analysis; these fragments were designated tag7 (FIG. 4) and tag6 (data not shown). The tag7 transcript was found to be well-represented in mRNA isolated from the highly metastatic VMR-L tumor line (FIG. 4, lane 2), but was not detectable in mRNA obtained from the non-metastatic VMR-0 tumor line (FIG. 4, lane 1).

Based on the Northern hybridization results, the length of the tag7 transcript was determined to be approximately 750 nucleotides. The nucleotide sequence of the murine tag7 gene (SEQ ID NO:1) was determined by Sanger sequencing and automated sequencing, and is shown in FIG. 1. The tag7 gene was found to be flanked on both sides by the same 5'-AATCGGGCTG-3' (SEQ ID NO:6) primer used in the PCR. Since this sequence had no homologies with known genes (determined by searches of the GenBank and EMBL genetic databases), the full-length cDNA of this gene was cloned. The cDNA library obtained from reverse transcription of total mRNA from the VMR-Liv tumor line contained approximately 800,000 clones. Fifty-two clones containing a cDNA of the tag7 gene were selected through hybridization with a $^{32}$P-labeled tag7 fragment. The nucleotide sequence was determined for several clones by Sanger sequencing and by automated sequencing, and the tag7 coding sequence of the most extended clone is presented in FIG. 1 (SEQ ID NO:1). The sequence of this clone and of the fragment obtained in the differential display were found to be practically identical. The nucleotide sequence of the coding segment of the tag7 clone was found to be 549 bp (FIG. 1; SEQ ID NO:1), and encoded a polypeptide of 182 amino acid residues (FIG. 1; SEQ ID NO:2).

Analysis of the predicted amino acid sequence of the murine tag7 polypeptide (FIG. 1; SEQ ID NO:2) indicates that there is an extensive stretch of highly hydrophobic amino acids at the N-terminus of the polypeptide that presumably acts as a membrane-anchoring domain, followed by a potential secretory signal sequence (between amino acid residues 20 and 22). Protein database searches (FASTA program from IntelliGenetics and BLAST from NCBI) revealed no significant similarity between the tag7 polypeptide and previously reported gene products. A mouse genomic library was constructed in λ FIX II vector, screened, and the genomic structure of tag7 was established. The murine tag7 gene was found to span 8 Kb, to consist of three exons and to contain a non-consensus TATA box (not shown). The mRNA start site was mapped using primer extension (data not shown) revealing two initiation starts separated by four nucleotides about 22 bp downstream of the TATA box, probably due to the non-consensus structure of the latter. Computer analysis of approximately 200 bp of the upstream sequence (Signal Scan) revealed a number of potential binding sites for some known transcription factors, such as Ets-1, NF-κb Sp-1 and myoD. The order of these binding sites and the distance from the mRNA start site were very close to the control region of the mouse LT-β gene (Pokholok, D. K, et al., *Pros Natl. Acad. Sci. USA* 92:674–678 (1994)). Furthermore, the 5' untranslated region of the tag7 mRNA was found to be rather short, which is typical for lymphotoxin genes.

These similarities between the genomic structures of tag7 and mouse LT-β encouraged a more detailed amino acid sequence analysis that revealed the existence of four regions in the extracellular domain of the tag7 polypeptide that bore structural similarity to the extracellular domains of other TNF family members. In the first two regions the level of identity with other TNF-related ligands was found to be high (data not shown), especially in residues buried in the β-sheet interior (Smith, C., et al., *Cell* 76:959–962 (1994)). The fourth domain showed less homology but the buried residues were still conservative. The tag7 was also found to be rich in cysteine residues and, as does LT-α (Aggarwal, B. B., et al., *J. Biol. Chem.* 260:2334–2339 (1985)), to contain four methionine residues. The distance between the presumptive transmembrane domain and the receptor binding domain intag7 was approximately the same (about 20 amino acids) as for LT-α (25 amino acids) and TNF-α (31 amino acids).

To further elucidate the three-dimensional structure of the tag7 polypeptide, and to determine its relation to the cell membrane and potential antigenic regions of the polypeptide, Kyte-Doolittle hydrophilicity and Jameson-Wolf antigenic index plots of the tag7 polypeptide were constructed using the PROTEAN computer program (DNASTAR, Inc.; Madison, Wis.). As shown in FIG. 2, the tag7 polypeptide contains a string of highly hydrophobic amino acid residues at the N-terminus (at approximately residues 1 through about 20), most likely representing an N-terminal signal sequence of approximately 20 amino acids in length. In addition, the antigenic index plot (FIG. 2) identified at least four potential epitope-bearing regions of the tag7 polypeptide, at amino acids 20–40, amino acids 55–75, amino acids 90–110 and amino acids 145–160, with a fifth potential weakly antigenic region at amino acids 120–130.

Example 2

Figure 5:
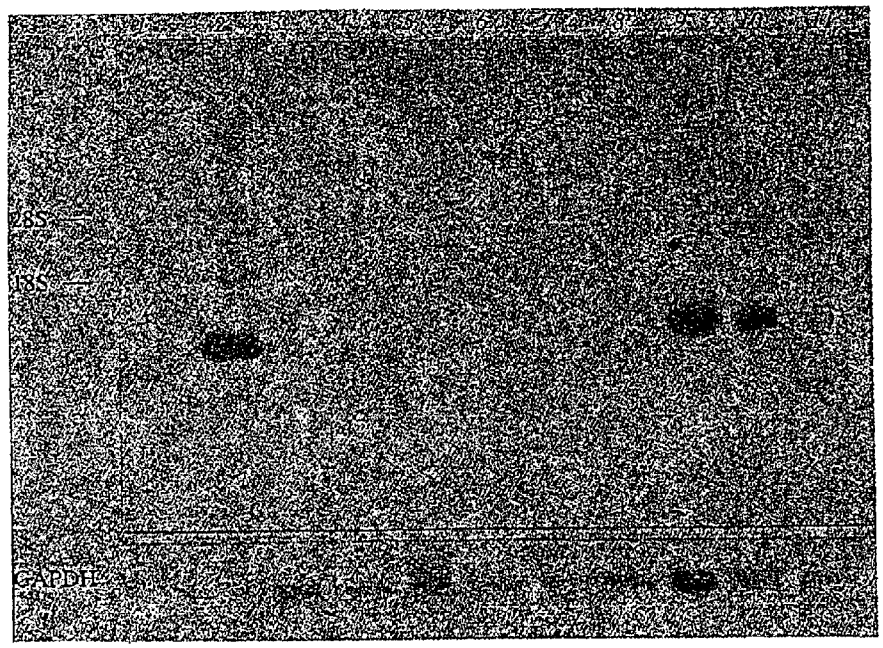
FIG. 5 is an autoradiograph of a Northern blot hybridization of total RNA isolated from various organs of a healthy mouse, probed with $^{32}$P-labeled DNA of the tag7 clone. Lane 1: VMR-0 cells; Lane 2: VMR-L cells; Lane 3: primary liver; Lane 4: primary thymus; Lane 5: primary ovary; Lane 6: primary heart; Lane 7: primary brain; Lane 8: primary kidney; Lane 9: primary spleen; Lane 10: primary lung; Lane 11: primary skin. GAPDH was the labeled probe used as a standard as in FIG. 2.

Analysis of the Transcription of the Murine Tag7Gene in Various Normal and Tumor Cells and Tissues in Mice To examine the levels of tag7 transcription in various normal and tumor cells and tissues, total RNA was isolated from various organs of healthy mice and probed via hybridization with $^{32}$P-labeled tag7 DNA. As shown in FIG. 5, the highest level of tag7 transcription in healthy mouse tissues was observed in the spleen and lungs, while lower levels were seen in the brain and thymus. The tag7 transcript was found to have the same length in all these organs—about 750 nucleotides, comprising the 549 bp coding segment plus additional 5' and 3' untranslated regions including a 3' polyA+ tail (not shown). No expression of tag7 was observed in liver or any other organs examined, even after prolonged exposure of autoradiograms. Together, these results indicate that the expression of the cloned tag7 gene in mouse is highly tissue-specific.

Figure 6:
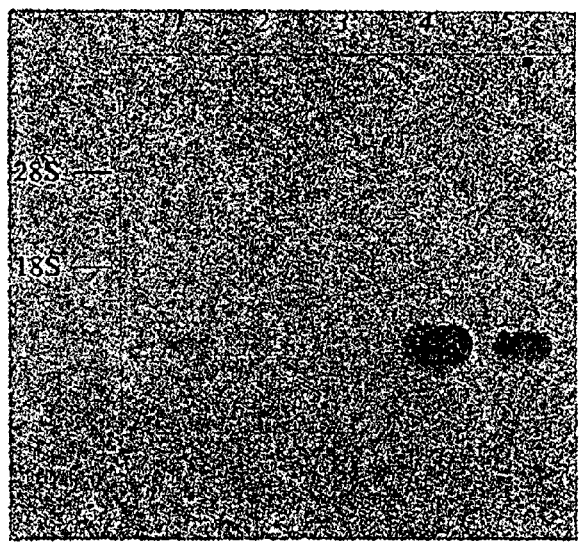
FIG. 6 is an autoradiograph of a Northern blot hybridization of total RNA isolated from various mouse cell lines, probed with $^{32}$P-labeled DNA of the tag7 clone. Lane 1: CSML-0 cells; Lane 2: CSML-100 cells; Lane 3: VMR-0 cells; Lane 4: VMR-L cells; Lane 5: VMR-Ov cells.

Upon examining various tumor cell lines, however, the transcription of the tag7 gene was found not to be limited to the metastatic VMR-L line. Expression of tag7 was also observed in other highly metastasizing tumor lines of the VMR family, particularly the VMR-Ov tumor (FIG. 6). The tag7 gene was also transcribed at a low level in the CSML-0 line, in which the frequency of metastasis to the lungs is about 5%.

To elucidate the association of the tag7 gene with the process of metastasis, RNAs from various cultures of cells of tumors of varied metastatic potential, organ-specificity of metastasis and origin were hybridized with the cDNA fragment of the tag7 gene; results are shown in Table 1.

TABLE 1

Investigated Cell Lines and the Level of Transcription of the murine tag7 Gene in These Lines

| Cell Culture | Frequency of Metastasis (organ-specificity), % | Level of Transcription of the tag7 Gene |
|---|---|---|
| VMR-0 - culture obtained from the VMR-0 tumor | 0 | — |
| VMR-L - culture obtained from the VMR-L tumor | 97 (liver) | + |
| CSML-0 - culture obtained from a mouse mammary adenocarcinoma | 5 (liver) | ++++ |
| CSML-100 - culture obtained from a mouse mammary carcinosarcoma | 100 (lungs) | — |
| Line 1 - pulmonary carcinoma | 100 (lungs) | — |
| LL Met - Lewis pulmonary carcinoma | 100 (lungs) | — |
| 10T½ - immortalized fibroblasts | — | — |
| MT1 TC1 - culture obtained from a mouse primary mammary adenocarcinoma | 10–25 (lungs) | ++ |
| MT1 TC3 - culture obtained from a mouse primary mammary adenocarcinoma | 100 (lungs, liver, kidneys, heart, lymph nodes, adrenals, ovaries) | — |
| RAC 5E    cultures obtained from a primary adenocarcinoma induced by the RIII variant of MMTV | Do not metastasize spontaneously | — |
| RAC 34E | | — |
| RAC 10P | | — |
| RAC 311C | | — |

Interestingly, these results demonstrate that when the tumor strains were converted into lines of transplantable cultures, a change in the level of transcription of/the tag7 gene was observed in vitro: transcription of the tag7 gene decreased significantly in the VMR-L cell line, while a moderate level of tag7 expression was observed in the CSML0 cell line. The tag7 gene was transcribed at a fairly high level in the MT1 TC1 line, a culture obtained from a primary mouse mammary adenocarcinoma which metastasizes to the lungs in 10–25% of cases.

Figure 7:
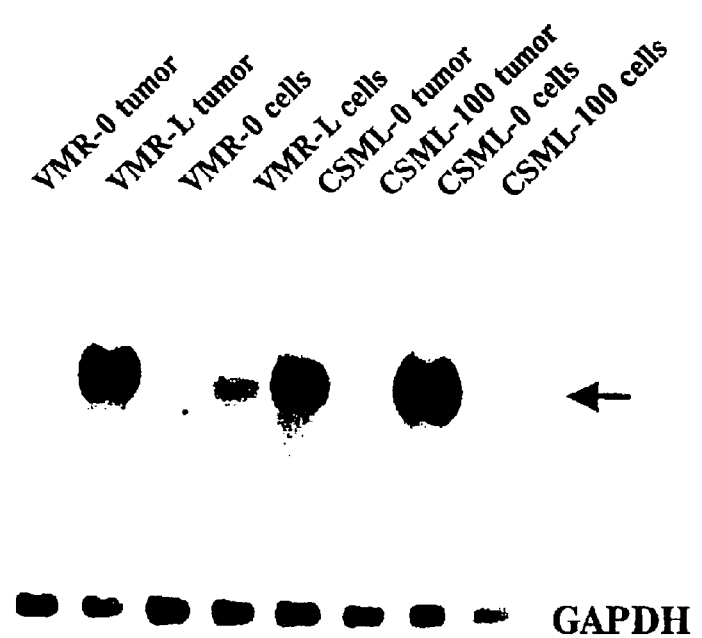
FIG. 7 is an autoradiograph of a Northern blot hybridization of total RNA isolated from various primary mouse tumors and the corresponding tumor cell lines, probed with $^{32}$P-labeled DNA of the tag7 clone.
Figure 8:
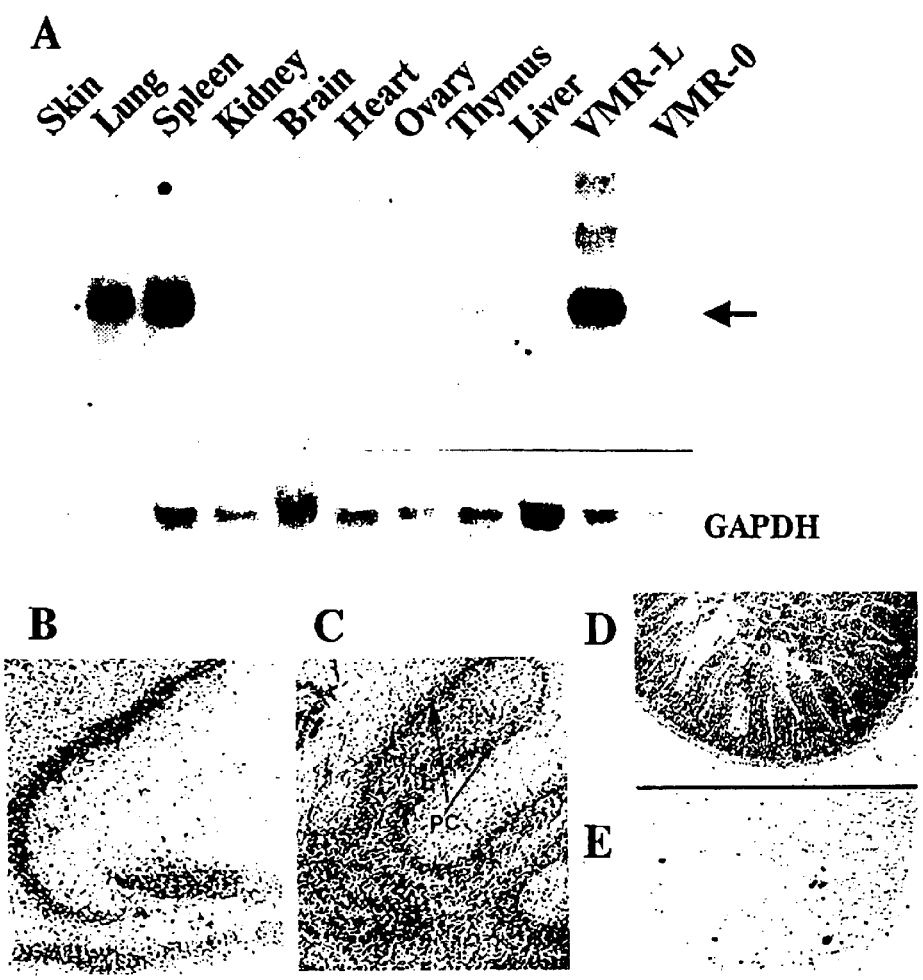
FIG. 8 is a composite of photographs demonstrating the tissue distribution of tag7 transcripts in mouse tissues.

Northern hybridization was used to more closely examine the correlation between tag7 mRNA expression and the metastatic properties of tumors. However, no correlation was observed upon hybridization of CSML0 and CSML-100 tumor total RNA (FIG. 7). Moreover, the expression of the tag7 gene appeared to be specific in this pair for the tumor with a low metastatic capacity, CSML-0. More intriguing was the confirmation the above observation that the tag7 mRNA level dramatically altered after the establishment of a primary tumor as a cell culture. There was also no correlation between the metastatic potential and tag? mRNA expression in other tested murine tumor cell lines (data not shown).

To determine the tissue distribution of tag7 transcription, Northern blot analyses and in situ hybridization were performed. Northern hybridization of several adult mouse tissues (FIG. 8A) revealed the highest level of tag7 transcription in lung and spleen, a detectable level in brain and thymus, and no or just a low level of the mRNA expression in other tissues tested. However, in situ hybridization on sections of selected organs allowed the detection of tag7 transcripts in specific areas of brain and intestine (FIG. 8B–E).

The level of tag7 transcription in hematopoietic and lymphoid cells, which are known to be a major source of cytokines of the TNF family, was also examined. Mouse splenocytes and resident peritoneal macrophages displayed a constitutively high level of tag7 mRNA (FIG. 9). Stimulation with IL-2 or phytohemagglutinin did not lead to a significant increase of the tag7 mRNA content in thymocytes and macrophages in the time course studied (data not shown). In mouse splenocytes cultured with LPS the level of tag7 transcription decreased within the first hours of activation, after which a small induction in tag7 mRNA transcription was observed (maximal at 24 hours post-stimulation) (FIG. 9). Northern blot analysis of the murine B cell lymphoma cell line WEHI-231 and the T cell lymphoma line LBRM-33 did not reveal any detectable level of tag7 transcription in the presence or absence of PMA, LPS or calcium ionophore for 20 hours (data not shown).

Example 3

Chromosomal Mapping of Murine Tag7

To determine chromosomal localization of tag7 in the mouse genome, metaphase chromosomes were analyzed by fluorescent in situ hybridization. A total of 80 metaphase cells were analyzed, with 62 exhibiting tag7-specific labeling. In these experiments, the specific labeling of the centromeric region of chromosome 7 was observed (data not shown). Measurements often specifically labeled chromosomes 7 demonstrated that the tag7 signal is located at a position that is about 9% of the distance from the centromere, an area that corresponds to band 7A3.

Example 4

Expression of Soluble Murine Tag7 in Cell Lines and Lymphoid Cells

To study tag7 expression at the protein level, rabbit polyclonal antibodies raised against the rtag7 were used in Western blotting analysis. While the tag7 protein was undetectable in cultured VMR-L cells and in culture media conditioned by these cells, a high level of the tag7 protein was detected in LPS-stimulated VMR-L cell conditioned medium (FIG. 10A). These results suggest that, as do TNF and LT-α, the tag7 protein may exist in two forms: soluble and cell-associated. A presumptive cell surface form of the protein was detected in the cellular extracts but most of the protein was secreted in the cultivation medium after LPS treatment. Although the increase in tag7 mRNA levels during activation was insignificant (data not shown), the levels of tag7 protein synthesis and secretion were relatively high. A similar pattern of gene expression was also observed for the tag7-expressing cell line CSML0 (data not shown). Freshly isolated mouse splenocytes contained a significant amount of cell-associated tag7 protein (FIG. 10B), which was increased by about five- to seven-fold upon LPS stimulation with a maximum at about 24 hours post-stimulation. Interestingly, these increased levels of tag7 protein expression coincided temporally with changes in protein localization: while most of the tag7 protein in splenocytes was found in a cell-associated form at early times after LPS stimulation, prolonged exposure of cells to LPS resulted not only in an increase in the overall amount of the protein but also in its secretion. The differences in the amount of the tag7 protein in non-activated VMR-L cells and splenocytes (FIG. 10A,B) may reflect the involvement of different mechanisms of gene activation between these two cell types, and/or the fact that splenocytes have already been activated in vivo prior to their isolation from the spleens

Example 5

DNA Fragmentation Induced by Soluble Murine Tag7

Tumor necrosis factor (TNF) has been shown to induce apoptosis in vitro in a variety of cell lines, in some cases via synergistic action with actinomycin D (Browning, J., and Ribolini, A., J. *Immunol.* 143:1859–1867 (1989); Larrick et al., 1990). The similarities between the structural organization of the tag7 gene and those of TNF-related cytokines, and the existence of a soluble form of the protein, suggested that the tag7 polypeptide may also trigger programed cell death.

To study this possibility for the soluble form of tag7, L929 cells were treated with conditioned supernatants from either unstimulated or LPS-stimulated VMR-L cells. Killing of target cells after incubation with 100 μl of conditioned supernatants was monitored by trypan blue staining. The results, shown in FIG. 11A, demonstrated that both TNF and tag7 killed L929 cells in the presence of actinomycin D, but only cell death induced by tag7 was inhibited by addition of anti- tag7 antibodies.

Since the process of apoptosis rapidly induces DNA fragmentation, the ability of the secreted form of tag7 to trigger apoptosis was examined using standard DNA fragmentation assays. Target L929 cells were treated with either conditioned supernatants of LPS-stimulated VMR-L cells, or with LPS-containing medium and recombinant TNF as controls. After a five hour incubation, fragmented DNA in the cellular cytoplasm was recovered and resolved by agarose gel electrophoresis. As shown in FIG. 11B, L929 cells were triggered to undergo apoptosis by treatment with the soluble form of the tag7 protein as evidenced by intranucleosomal DNA fragmentation. In contrast, control cells exhibited no DNA fragmentation These results indicate that tag7 treatment can induce apoptosis in certain tumor cells, and suggest that, as does TNF, tag7 may cause programmed cell death in other mammalian cells as well.

Example 6

Tumor Growth Inhibition Induced by Tag7 a) Generation of Tag7 Producing Cell Lines

Having demonstrated that tag7 can induce apoptosis in vitro, the effects of tag7 on tumor growth in vitro were next examined To facilitate these biological studies, full-size cDNA copies of the murine tag7 gene were subcloned in mammalian expression vectors. VMR-0 cells not constitutively expressing tag7 mRNA were genetically transformed with these vectors to produce tag7 mRNA; transfectants were selected for G418 resistance and cloned. A number of clones were analyzed with regard to the level of tag7 transcription, and two clones (4SX and 12SX) differing in the level of tag7 mRNA were selected for further analysis (FIG. 12A). The cDNA of tag7 was cloned into the vector pM5Gneo and stable transfection of VMR-0 cells was performed.

Modified cells were selected for G418 resistance, cloned, and analysed (clone 8SX). This vector allowed to obtain an amount of protein detectable by Western blot analysis (FIG. 12D, upper panel) and cytotoxicity of cell culture medium (lower panel), while under CMV promoter only tag7 mRNA was detected (clones 12SX, 4SX). For this experiment, conditioned medium of a 8SX clone was filtered through a 0.2 $\mu$m membrane and applied to the target cells (L 929 cells; 100 $\mu$l per well containing approximately $10^4$ cells). Cytotoxicity was measured after 5 hrs of incubation by Trypan Blue staining and the CytoTox Kit (Promega). However, pM5Gneo vector carried a part of myeloproliferative sarcoma virus gag-gene and cells mock-transfected by this vector was significantly more immunogenic in immunodeficient animals than control cells transfected with the pBK/CMV plasmid. Parental VMR cells and mock-transfected VMR-0 Neo cells did not produce a detectable level of the tag7 mRNA. Genetically modified VMR-0 cells did not show any obvious differences from the parental cells in either morphology or cell proliferation in vitro.

b) Expression of the tag7 Gene Suppresses the Growth of VMR-0 Cells in Vivo in Syngeneic Mice To determine whether tumor cells when transfected with tag7 are able to change their tumorigenicity, $10^6$ tag7 transfected and control cells were implanted subcutaneously (s.c.) into syngeneic A/Sn mice. The tag7 expressing cells grew much more slowly than the control cells (FIG. 12B: Open boxes—parental tumor cells VMR-0, closed tiangles—mock-transfected VMR-0, open circles—suppression of 4SX growth by injection of antiTag7 polyclonal antibodies in the site of cells, closed boxes—bystander effect of coinjection of parental (VMR-0) and tag7-modified (4SX) tumor cells, open triangles—growth rate of the clone 12SX, closed circules—growth rate of the clone 4SX. C—parental and modified (clone 4SX) tumors, dissected from singeneic animals.) and the rate of tumor growth suppression correlated with the level of tag7 mRNA and protein content. Parental and mock-transfected cells grew progressively in control animals.

FIG. 12C shows tumors formed by parental VMR-0 cells, dissected 4 weeks post injection, and tumors formed by 4SX cells, dissected 5 weeks post injection.

A most intriguing observation was the complete absence of hemorragic necrosis even when tumors reached a rather large size after 90 days p.i. whereas the parental and mock-transfected tumors started to be necrotic in less than two weeks p.i. This observation was further confirmed by histological analysis of tumors caused by injection of parental cells (VMR-0 cells) and tag7-modified cells (4SX cells). The antiproliferative effect of tumor growth was indirect because the tumor cells did not show altered growth kinetics in vitro. The indirect effect of tumor growth suppression in vivo is supported by co-implantation of 4SX cells with parental VMR-0 cells ($10^6$ each, $2\times10^6$ total) at the same s.c. site. Although the tumor growth inhibition was not as strong as with transfected cells only, it clearly demonstrated the bystander effect of unmodified tumor cells. To prove that loss of tumorigenicity resulted from Tag7 secretion modified tumor cells were injected s.c. into syngeneic mice together with polyclonal anti-Tag7 antibodies. Tumorigenicity of modified tumor cells was practically blocked by injections of anti-Tag7 antibodies in 2 days interval and the abolition of their administration by day 8 led to immediate restoration of the antiproliferative effect Injection of tag7-bearing tumor cells did not cause abnormalities (such as weight loss) in the host mice during the experimental period. This observation indicates that secreted Tag7 can induce antitumor effect on parental tumor cells without inducing systemic toxicity.

Example 7

Growth Rate of Modified Tumor Cells Depends on Immune Status of the Organism

To analyse possible cellular mechanisms involved in the tag7-induced antitumor response, transformed tumor cells were also analyzed in nude (T cell deficient) and SCID (T and B cell deficient) mice (FIG. 13). For this experiment only cells with a high tag7 level were used (4SX). The tumor size was monitored during a 40 day period. Parental and mock-transfected cells had quite similar growth kinetics in nude and SCID mice. The growth rate of modified tumors was suppressed in both models, however tumor size at the end of the trial period in SCID model was 50% larger than in nude mice. It indicates that the absence of B lymphocytes in SCID mice could play a role in the partial restoration of tumor growth rate.

FIG. 14 shows the nude mice challenged with tag7-modified VMR-0 cells (upper panel, clone 4SX) and with parental cells (lower panel).

Example 8

Tumor Rejection is Due to an Apoptotic Process in Modified Tumors

The rejection of tag7 transfectants was independent of cytotoxic T lymphocytes, because it was observed in T cell-deficient nude mice. To understand the underlying cellular mechanisms, histological and electron microscopy analysis of the tumor tissue of syngeneic animals was performed 3 weeks after injection. The control VMR-0 tumor showed a solid growth, with central necrotic areas. The incidence of mitotic cells was rather high, approximately 6–8% of cells were in mitosis and apoptotic cells in parental tumor were rare (Table 2 shows that the total differences in proliferative activity between parental and modified tumors were more than 50 fold).

TABLE 2

| Tumor | Mitosis | Apoptosis |
| --- | --- | --- |
| VMR-0 | 6–8% | 0.5–1% |
| 4SX | 2–3% | 8–10% |

Figure 15B:
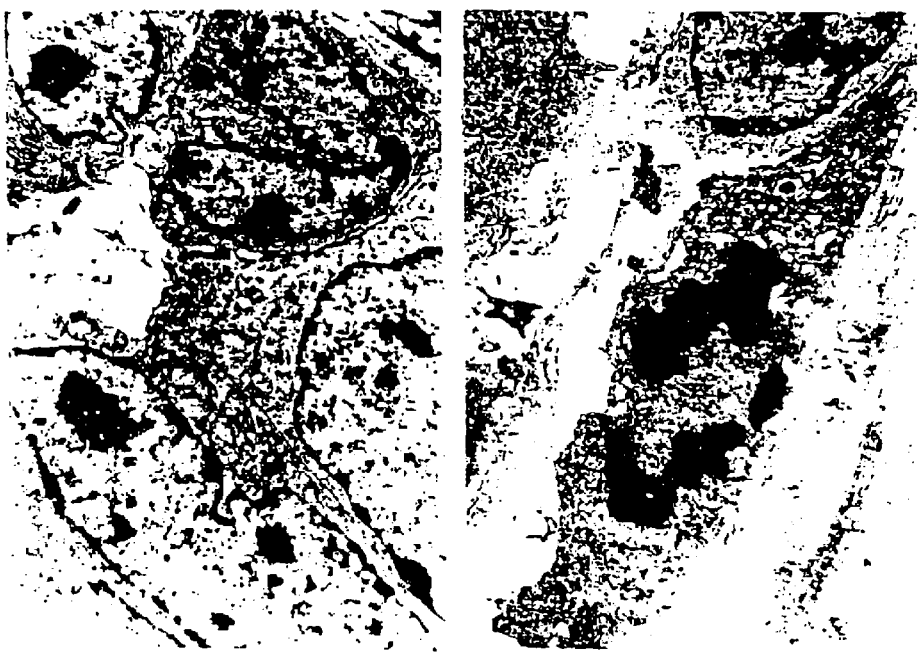
Figure 15C:
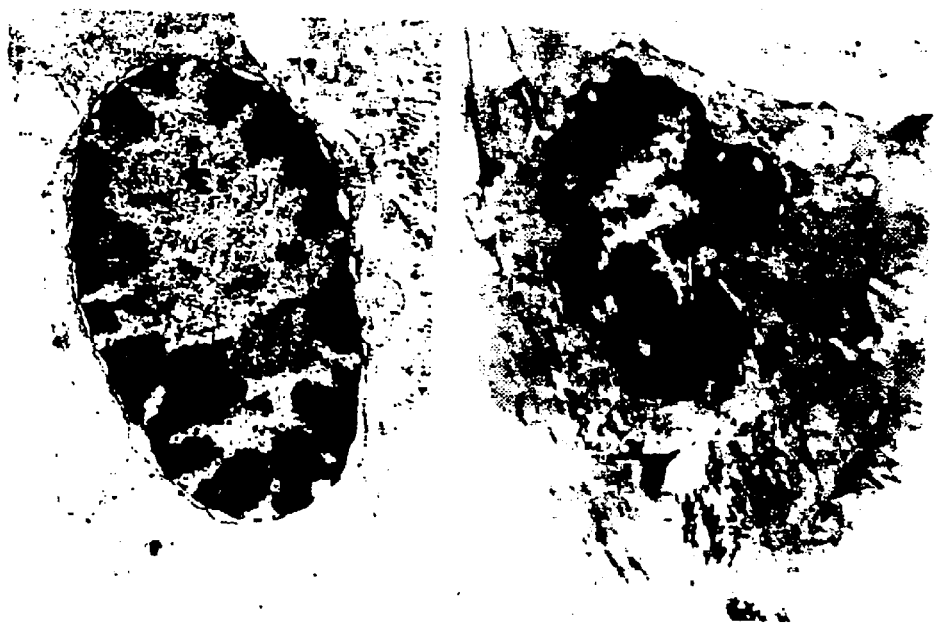

Modified tumors were scattered and devoid of necrotic foci. Electron microscopy analysis revealed that more than 8% of tumor cells had features characteristic for apoptosis, starting from aggregation of condensed chromatin, nuclei fragmentation, etc). The upper panel of FIG. 15A shows a histological section of a tumor formed by parental cells (VMR-0 cells), eosin/hematoxilyn stained. Arrows indicate mitotic cells. The lower panel of FIG. 15A shows a histological section of a tumor formed by tag7-modified cells (4SX cells), eosin/hematoxilyn stained. Arrows indicate apoptotic cells. FIG. 15B shows electon microscopy pictures of mitotic cells in a tumor formed by parental cells (VMR-0 cells); FIG. 15C shows electron microscopy pictures of apoptotic cells in a tumor formed by tag7-modified cells (4SX cells).

Example 9

B Cells Mediate Primary Tumor Rejection

Although in SCID mice modified tumor growth was also suppressed, average size of tumors was larger than in nude mice, implicating a role for B cells in apoptosis of modified tumor cells. To identify the effector cells, we performed immunohistological analysis of tumor tissue. Parental and tag7 modified tumor cells (4SX) were injected s.c. into syngeneic mice, tumor tissues were isolated 3 weeks later, and sections were stained with anti-CD45R/B220, -Gr-1, -CD8a, -CD4, -CD11b(Mac-1) antibodies. We did not observe a significant difference in tumor infiltrated granulocytes, macrophages or CD4+, CD8+ cells (data not shown) in parental and modified tumors. However, Tag7 producing tumors were heavily infiltrated by CD45R+ cells (FIG. 16A) i.e. presumably by B-lymphocytes. In contrast, in parental tumors CD45R+ positive cells were practically absent (FIG. 16B). Major infiltration occured at tumor border and in the areas where blood vessels were concentrated.

Example 10

Induction of Protective Immunity by Transient Expression of Tag7 in Mouse Melanoma M3 Cells (Prophylactic Model)

M3 mouse melanoma cells were transiently transfected with the tag7 expressing construct under the CMV promoter. One day after the transfections cells were harvested and implanted s.c. into syngeneic DBA/2 mice. A week after the implantation of the transfected tumor cells animals were challenged with parental M3 cells at distinct s.c. sites. The growth rate of the parental M3 cells was suppressed in animals into which tumor cells transfected with Tag7 expression construct had been implanted. Table 3 shows the tumor size of animals that had been vaccinated with either GM-CSF or tag7 transfected M3 cells (with non-transfected M3 cells as a control; the number of cells used for vaccination is given in the table) and subsequently challenged with $10^6$ parental M3 melanoma cells. The size of the tumors formed by parental M3 melanoma cells was monitored; it is given in the table in mm$^3$. The experiment showed that transient expression of Tag7 inhibited the growth of these tumors with at last the same efficiency as obtained with GM-CSF.

FIG. 17 shows the survival rate of DBA/2 mice in this experiment (open circles: 500.000 M3 cells per mouse; open squares: 500.000 GM-CSF-transfected M3 cells per mouse; filled squares: 500.000tag7-transfected M3 cells per mouse; filled circles: $10^6$ parental M3 cells per mouse.

TABLE 3

|  | WEEKS | | | | | |
| --- | --- | --- | --- | --- | --- | --- |
|  | 1 | 2 | 3 | 4 | 5 | 6 |
| M3 melanoma control | | | | | | |
| 500.000 cells/mouse | 0.0 | 150.8 | 858.0 | 2520.9 | 3668.5 | died |
| 100.000 cells/mouse | 0.0 | 372.9 | 2756.6 | 3893.1 | 6118.5 | died |
| M3 GM-CSF transfected | | | | | | |
| 500.000 cells/mouse | 0.1 | 9.8 | 95.3 | 154.1 | 568.4 | 890.3 |
| 100.000 cells/mouse | 0.0 | 78.7 | 265.4 | 397.8 | 621.9 | 745.4 |
| M3 Tag7 transfected | | | | | | |
| 500.000 cells/mouse | 0.0 | 17.8 | 66.9 | 149.9 | 353.1 | 515.0 |
| 100.000 cells/mouse | 0.0 | 33.0 | 81.0 | 99.6 | 352.2 | 495.6 |

Example 11

Identification of a Tag7 Homologue in Human Tissues

To determine if a homologue of the murine tag7 gene is expressed in humans, a commercial blot containing polyA+ RNA from various human immune tissues was probed with $^{32}$P-labeled murine tag7 cDNA probes. As shown in FIG. 18, the labeled tag7 probe hybridized to RNA from several human tissues. Most notably, strong hybridization was observed to a 1 Kb band from human bone marrow, a 2.00 Kb band from human fetal liver and a 2.1 Kb band from human lymph node. A somewhat weaker hybridization was observed to a 2.1 Kb band from human spleen and to 0.9 Kb bands from human fetal liver and a 1.0 Kb band from peripheral blood leukocytes. RNA isolated from human thymus was not hybridized by the labeled tag7 probe used in the current experiments. Together, these results indicate that a human homologue of tag7 exists and is expressed in a variety of human tissues.

Example 12

Isolation and Sequencing of Human Tag7

Northern blot analysis of human RNAs using murine tag7 as a probe had shown high expression of a human homolog in bone marrow (BM) and low expression in peripheral blood cells (PBLs) (Example 11).

A human BM library (Clontech, Human Bone Marrow 5'-STRETCH-PLUS cDNA cat.no. HL5005b) was screened according to the Clontech protocol with the murine tag7 cDNA as a probe. The probe was excised from the pX plasmid as a XhoI-EcoRI fragment, approx. 700 bp long. The purified band was labeled with P32 with high prime labeling kit (Boehringer Mannheim, cat. no. 1 585 584).

$1 \times 10^6$ phage plaques were screened. 25 positive clones could be detected in the first screening which were further plaque purified and analysed.

Lambda DNA of positive single colony clones was prepared with Qiagen lambda kit #12549. The inserts were excised by restriction enzyme digestion with NotI and cloned into the vector pGEM11f+. 3 clones contained human tag7 (clones #6,#12 and #13) one of which contained the complete cDNA (#13). The complete clone #13 contained a second cDNA upstream to the tag7 cDNA, coding for MRP-8, macrophage migration inhibitory factor (MIF)-related protein, Acc.no. X 006234. This protein is a calcium binding protein in macrophages. All 3 clones were sequenced. A fourth clone (#10) was sequenced directly from the lambda DNA by amplifying the insert by PCR prior to sequencing.

Within the obtained sequence, there was the open reading fame as set forth SEQ ID NO: 3, encoding tag7 according to the amino acid sequence of SEQ ID NO: 4.

The human tag7 polypeptide has, at its N-terminus, similarly to the murine tag7, a hydrophobic stretch of approximately 20 amino acids, which represents a putative signal sequence. It is routine for the person skilled in the art to determine the existence or the length of such leader sequence, respectively, by sequencing the N-terminus of the mature (natural or recombinant) tag7 polypeptide.

The alignment of the human and the mouse cDNA sequence (using the "Clustal method with Weighted residue weight table") reveals 77,2% similarity. On the protein level a similarity of 66.1% was determined by using the the "Clustal method with identity residue weight table".

Example 13

Expression of Recombinant Murine and Human tag7 a) Expression of Recombinant Murine Tag7 in *E.coli:*

For a first set of experiments, the expression plasmid designated tag7pDH13/12, which contains the STII leader and phoA promotor (pDH13 derived) and the expression plasmid designated tag7pDH15/1, with the STII leader and Trp promoter (pDH15 derived) were used.

To obtain the plasmids, the STII leader was fused to murine tag7 ("mutag7") in a SOE reaction ("splice overlap extension"; Horton, R. M., Hunt, H. D., Ho, S. N. Pullen, J. K, and Pease, L. R, Gene, 77: 61–68 (1989)) and a XhoI-PstI fragment was generated and cloned into the vectors pDH13 (U.S. Pat. No. 5,710,027) and and pDH15 respectively. pDH15 is identical to pDH13, only the phoA promotor has been exchanged to a synthetic Trp promoter. The Trp promotor is inducable with Indolacrylic acid. The STII leader replaced the putative leader sequence of mutag7, the first amino acid residues of mutag7 were SEWR (beginning at amino acid no. 24 of SEQ ID NO:2). The DNA fragments to be fused together were generated in two separate PCR reactions:

PCR1:
 forward primer EBI5141: 5'GAAAGGGCCTCGT-GATAC3' (SEQ ID NO: 8) backward primer. AC1= EBI8024:
 5'CAGGGCCCTCCACTCACTTGCATAG-GCATTTGTAGC3' (SEQ ID NO: 9)
The DNA template was pDH13.
PCR2:
 forward primer: AC2=EBI8025
 5'GCTACAAATGCCTATGCAAGTGAOTG-GAGGGCCCTG3' (SEQ ID NO: 10),
 backward primer EBI8203:
 5'GGCCGCTAGCCTGCAGTTATCACTCTCG-GTAGTGTTCCCAG3' (SEQ ID NO: 11)
DNA template was the pX-plasmid carrying mutag7 (SEQ ID NO:1).

The PCR fragments were run on a 1% agarose gel and purified with Qiagen Qiaex II. The purified PCR fragments were then fused together in the following SOB reaction:
 forward primer EBI5141
 backward primer: EBI8203
 DNA templates: purified PCR1 and PCR2 fragments.

The resulting SOE fragment was then digested with XhoI and PstI and cloned into pDH13 and pDH15, which had been digested with the same enzymes. pDH13 and pDH15 carry a human interferon alfa fragment as an insert, which was deleted by the XhoI-PstI digestion and replaced with the mutag7 SOE fragment E. coli DHα5 was transformed with the expression plasmids. E. coli extracts of the transformed bacteria were analysed for tag7 expression in Western blots.

For a further experiment, the expression plasmid designated pGEX-2TmuTag7/clone3 was used to express murine tag7 as a GST-tag7 fusion protein.

Synthetic oligonucleotides were designed to add restriction sites BamHI to the 5' end and EcoRII to the 3' end of the mutag7 cDNA in a PCR reaction. PCR reaction was performed with pX plasmid as DNA template and the primers:
 EBI8471 (contains the BamHI site) and EBI8472 (contains the EcoRI site)
 EBI8471: 5'GGCGGATCCGAGTGGAGGGCCCTGC-CATCC3' (SEQ ID NO: 12)
 EBI8472: 5'GGCGAATTCTTATCACTCTCGGTAGT-GTTC3' (SEQ ID NO: 13)

The PCR fragment was purified and digested with BamHI and EcoRI and cloned into the same sites of pGEX-2T (Pharmacia). The construction of the primers was chosen so that the first mutag7 residues fused to the GST protein were Glu Trp Arg Ala (beginning at aa position 25), thus omitting the putative leader sequence. E. coli w3110 was transformed with the plasmid pGEX-2T muTag7/clone3 and the expression of GST-murine tag7 was verified in a Western blot (FIG. 19). The Western blot shows a band of approximately 44.5 kD (26 kD GST plus 18.5 kD tag7) in lane a; lane b shows, as a positive control, murine tag7 from supernatants of CSML-0 cells at a MW of 18.5 kD).

b) Expression of Recombinant Murine Tag7 in CHO Cells

For these experiments, the expression plasmid designated tag 7+LpAD-CMV1, with endogeneous mutag7 leader (pAD-CMV1 derived) was used. Synthetic oligonucleotides were designed to add restriction sites BgIII to the 5' end and NheI to the 3' end of the mutag7 cDNA in a PCR reaction. PCR reaction was performed with pX plasmid as DNA template and the primers:
 EBI8233 (contains the BgIII site) and EBI8203 (contains the NheI site)
 EBI8233: 5'GGCCAGATCTCGTCCAGCATGTTGT-TGCCTGTGCT3' (SEQ ID NO: 14)

The PCR fragment was purified and digested with BgIII and NheI and cloned into pAD-CMV1 (EP393.438), which had been digested with BamHI-XbaI.

Stable cell lines of B16 and C26 expressing murine tag7 were generated: The plasmid tag 7 +L pAD-CMV1 was linearized with FspI and cotransfected with the plasmid pCI-neo (Promega) into CHO cells. Clones expressing murine tag7 were identified by Western blot analysis of the cell culture supernatants.

For further experiments, the expression plasmid designated Tag7+IgL-pAD-CMV1/2, with the synthetic immunoglobulin light chain leader (pAD-CMV1 derived) was used.

The synthetic immunoglobulin light chain leader of INPEP4+ leader plasmid was fused to mutag7 in a SOE reaction (splice overlapping extension) and a BgIII-NheI fragment was generated and cloned into the vector pAD-CMV1 (WO 93/11257). The immunoglobulin leader replaced the putative leader sequence of mutag7, the first amino acid residues of mutag7 were chosen EWRA. The DNA fragments to be fused together were generated in two separate PCR reactions:
PCR1:
 forward primer EBI8143: 5'GGCACCAAAAT-CAACGGGAC3' (SEQ ID NO: 15)
 backward primer.
 EBI8201:5 ° CAGGGCCCTCCACTCACATCGTG-CACCTGGG3' (SEQ ID NO: 16)
The DNA template was INPEP4+ leader
PCR2:
 forward primer. EBI8202:
 5'CCCAGGTGCACGATGTGAGTGGAGGGCCCTG3' (SEQ ID NO: 17)
 backward primer: EBI8203:
 5'GGCCGCTAGCCTGCAGTTATCACTCTCG-GTAGTGTTCCCAG3' (SEQ ID NO: 18)
DNA template was the pX-plasmid carrying mutag7.

The PCR fragments were run on a 1% agarose gel and purified with Qiagen Qiaex II. The purified PCR fragments were then fused together in the following SOE reaction:
 forward primer EBI8143
 backward primer: EBI8203
 DNA templates: purified PCR1 and PCR2 fragments.

The resulting SOE fragment was then digested with BgIII and NheI and cloned into pAD-CMV1, which had been digested with BamHI and NheI.

c) Expression of Recombinant Human Tag7 in CHO Cells:

For the expression of human tag7, the expression plasmid designated hutag7 pAD-CMV1/clone1, with endogeneous hutag7 leader (pAD-CMV1 derived), was constructed.

Synthetic oligonucleotides were designed to add restriction sites HindIII to the 5' end and EcoRI to the 3' end of the hutag7 cDNA in a PCR reaction. PCR reaction was performed with plasmid pGem hu Bone Marrow Tag7 #13/1 as DNA template and the primers: EBI8748 (contains the HindIII site) and EBI8749 (contains the EcoRI site)

EBI8748: 5'GGCCAAGCTTCCACCATGTCCCGC-CGCTCTATGCTG3' (SEQ ID NO: 19)

EBI8749: 5'GGCCGAATTCTTATCAGGGGGAGCGG-TAGTGTGG3' (SEQ ID NO: 20)

The PCR fragment was purified and digested with HindIII and EcoRI and cloned into the same sites of INPEP4 and pAD-CMV1, respectively.

Example 14

Preparation of Anti-mutag7 and of Anti-hutag7 Antisera

Two different peptides, derived from the mutag7 (murine tag7) sequence and two different peptides from the hutag7 (human tag7) sequence were synthesised:

mutag7 peptides peptide nemu-A: RSEWRALPSECSSRLGHPY (SEQ ID NO: 21)

peptide nemu-B: GEDGHVYEGRGWNIKGDHTGCY (SEQ ID NO: 22)

For immunisation the peptides were mixed (1:1).

hutag7 peptides peptide nehu-A: AQETEDPACCSPIVPRNEWKALA-SEY (SEQ ID NO: 23)

peptide nehu-B: GEDGLVYEGRGWNFTGCY (SEQ ID NO: 24)

For immunisation, the peptides were mixed (1:1).

Rabbits were immunised s.c.on day 1 and 21 with 500 µg peptide mix. On day 42, 250 µg peptide mix and on day 49, 200 µg peptide mix, respectively, were injected i.m. On day 50 and day 51, 250 µg peptide mix were injected iv. Blood was drawn on days 63, 70, 77 and 84.

Affinity purification of the anti-mutag7 and anti-hutag7 antisera.

Affinity columns were prepared by coupling the peptide mixes of mutag7 and hutag7 to separate Affi-Gel 10 (Biorad) columns under anhydrous coupling conditions. 20 ml of each polyclonal antiserum was purified on the corresponding column, washing buffer was 0,02M sodium-phophate, pH 7.4, Elution Buffer was 0,1 M Glycin, pH 2.5. The affinity purified antisera were dialysed in PBS, steril filtered, and stored at –20° C.

Example 15

Expression of Tag7 in Human Normal and Tumor Tissues

Immunohistochemical analysis of frozen tissue sections was performed as described recently Karl-Heinz Heider, Jobst Dämmrich, Petra Skroch-Angel Hans-Konrad Müller-Hermelink, Hans Peter Vollmers, Peter Herrlich and Helmut Ponta: "Differential expression of CD44 splice variants in intestinal and diffuse type human gastric adenocarcinomas and normal gastric mucosa". Cancer Res. 53, 4197–4203, 1993.). Briefly, frozen sections were incubated with the primary antibody (anti-Tag-7 rabbit antiserum, as prepared in Example 14, 10 µg/ml, or rabbit IgG control serum, 10 µg/ml) for 1 h at room temperature. Bound antibodies were detected using the avidin-biotin-peroxidase complex system (DAKO, Denmark). Evaluation of the staining was performed using a Zeiss Axioskop, staining intensity was divided into – (negative), + (weakly positive), and ++ (moderate to strongly positive).

Expression of the Tag-7 antigen in human normal and tumor tissues was investigated by immunohistochemistry. In normal tissues, positive staining was detected in all investigated tissues. In cerebellum and cerebral cortex single cells reacted weakly with the anti-Tag-7 antibody. Lymphatic cells in duodenum, spleen, and lymphnode were moderate to strongly positive. Staining was mostly confined to the cell membrane and intercellular space. In lung, both alveolar epithelium and vascular endothelium reacted strongly with the anti-Tag-7 antibody. Results are summarized in Table 4.

TABLE 4

Immunohistochemical analysis of human normal tissues with anti-Tag-7 antibodies

| Tissue | Tag-7 staining |
| --- | --- |
| cerebellum | single cells + |
| cerebral cortex | single cells + |
| duodenum | lymphocytes ++ |
| lung | alveolar epithelium ++; endothelium ++ |
| lymph node | subset of lymphocytes ++ |
| spleen | subset of lymphocytes ++ |

In all investigated tumor types positive staining with the anti-Tag-7 antibody was observed (Table 5). Staining in most cases was moderate to strong and mostly confined to the tumor stroma with a diffuse staining pattern (see FIG. 1). In renal cell carcinoma also infiltrating lymphocytes and vascular endothelium strongly reacted with the anti-Tag-7 antibody. Tumor cells in general showed no reactivity with anti-Tag-7 with the exception of colon adenocarcinoma where part of the tumor cells was positive (not shown).

TABLE 5

Immunohistochemical analysis of human tumor tissues with anti-Tag-7 antibodies

| Tissue | Tag-7 staining |
| --- | --- |
| breast adenocarcinoma | stroma + |
| colon adenocarcinoma | tumor islands/stroma ++ |
| lung adenocarcinoma | stroma ++ |
| lung squamous cell carcinoma | stroma ++ |
| renal cell carcinoma | stroma ++; lymphocytes/endothelium ++ |

FIG. 20 shows the immunohistochemical analysis of a lung adenocarcinoma with anti-Tag7-antibodies. Arrows indicate positive staining of the tumor stroma General Discussion To search for genes that are selectively expressed in tumors with high metastatic potential, a pair of tumors of identical origin and differing in their metastatic properties was chosen. Two substrains of the highly metastatic cancer VMR (which has a broad organ spectrum of metastasis and a frequency of metastasis to the liver no greater than 5%) were isolated in previous studies (Senin, V. M., Vestn. Akad. Med. Nauk. SSSR 0(5):85–91 (1984)): the VMR-0 line (frequency of metastasis to the liver of about 0%) and the VMR-L line (frequency of metastasis to the liver of about 100%). In contrast to the CSML-0 and CSML-100 tumor lines, none of these VMR tumors expresses the previously cloned mts1 gene which is transcribed in the majority of tumors (Grigorian, M. S., et al., *Genetika* (*USSR*) 25(6): 993–1000 (1989)), making the search for other genes that participate in the process of metastasis reasonable. If one considers the tumors obtained in accordance with previously proposed models (Fidler, I. J., and Hart, I. R., *Science* 217:998–1001 (1982)), it is evident that the VMR-L tumor may derive from a metastatic subpopulation of cells which was present in the initial VMR tumor at a very low level and which had a relatively short life span (Kerbell, K. S., *Adv. Cancer Res.* 55:87–131 (1990)).

This probable similar origin of the pair of tumors studied here offers the possibility of using the "differential RNA display" technique to identify metastasis-associated genes. In gross, the genetic differences between the VMR-0 and VMR-L tumors were insignificant, confirming their common origin to a certain degree. Nevertheless it was possible by means of this approach to isolate several fragments of DNA corresponding to differentially expressed RNAs in the VMR-0 and VMR-L tumors. Analysis of the isolated fragments using Northern hybridization with total RNA from these tumors made it possible to assign the majority of the fragments to the class of known repeat sequences (the IAR element, etc.). However, several of the fragments obtained could not be so assigned and were therefore of undoubted interest.

One such fragment isolated and characterized here is the tag7 gene which exhibits a very high level of transcription in the liver-metastasizing VMR-L tumor (see FIG. 2). Sequence analysis showed that the PCR fragment was flanked on both sides by the 5' terminal primer 5'-AATCGGGCTG-3' (SEQ ID NO:6). When the nucleotide sequence of a cDNA clone from the total VMR-L cDNA library was analyzed, a sequence which is homologous to this primer over a length of eight bp was found at a distance of 52 nucleotides from the 3' poly A+ tail of the cloned cDNA. It is likely that the traditional oligo-dT primer could be used in the "differential RNA display" technique instead of the 3' terminal primer, and only the 5' terminal primers could be varied; such an approach would probably decrease the number of fragments obtained, but would simultaneously increase the resolving capacity of the gel.

Those errors which arise in the numerous cycles of the PCR may be classified as deficiencies of the technique. When the nucleotide sequence of the fragment obtained in the PCR and the cDNA of the tag7 clone were compared, it was found that 44 nucleotides at the 5' end of the amplified fragment do not coincide with the analogous segment of the sequence of the clone of the cDNA.

Computer analysis of the full-length sequence of the murine tag7 cDNA revealed two open reading frames (ORFs), corresponding to polypeptides of approximately 182 amino acids and 91 amino acids in length. Both translation starts satisfied the averaged Kozak sequence (Kozak, M., *J. Cell Biol.* 108:229–241 (1989)) to different degrees. However, in the case of the longer ORF, the number of nucleotides coinciding with the translation consensus is greater than for the shorter ORF, and it is probably the first methionine in particular that is the site of translation initiation. In addition, the methionine in the +37 to +39 bp position of the full-length cDNA is closer to the 5' end, and consequently is more favorable for translation initiation (Kozak, M., *J. Cell Biol.* 108:229–241 (1989)). However, translation of a functional tag7 polypeptide could also be initiated from the second methionine.

The molecular weight of the predicted tag7 polypeptide (182 amino acid residues; SEQ ID NO:1) is about 20 KDa. ID order to search for homologies with previously described sequences, the tag7 nucleotide sequence and the predicted amino acid sequence of its product were analyzed in the GENE and SWISSPROT data banks by means of the FASTA (Heidelberg, Germany) and BLAST (Washington, D.C., USA) homology-searching programs. No substantial homologies with previously known sequences were found, with the exception of an insignificant homology of a hydrophobic segment (between 2 and 12 amino acid residues), at the N-terminus of the predicted tag7 polypeptide, with the β chain of the human T-cell receptor. This hydrophobic region is also homologous to the signal sequences of some proteins (for example, the precursors of calreticulin, osteocalcin and extracellular globin III). The presence of a hydrophobic region at the N-terminus of the predicted tag7 polypeptide suggests that this polypeptide may have a transmembrane localization or may be secreted.

The expression of tag7 was not found to correlate with the organ-specificity of metastasis; the tag7 gene was transcribed not only in the cells of the liver-metastasizing VMR-L tumor, but also in the cells of the ovary-metastasizing VMR-Ov tumor. Among normal organs, the maximal level of expression of the tag7 gene was observed in the cells of those organs in which basal membrane cells have a high relative proportion. This correlation may not be purely coincidental, but may reflect the role that the basal membrane plays in the metastatic process (Stetler-Stevenson, W. G., et al., *Ann. Rev. Cell Biol.* 9:541–573 (1993)). It is interesting that the level of expression of the tag7 gene in metastasizing tumors is much higher than in the same cells in culture. This result is the converse of recently reported results from studies of gene expression in primary and cultured cancer cells (Zhang, L., et al., *Science* 276:1268–1271 (1997)), and may represent a response to the interaction of tumor cells with host cells of the basal membrane, for example in the process of the invasion of the basal membrane by metastatic tumor cells. The participation of cells of the stroma in regulating the expression of tag7, as occurs, for example, in stromelysin-3 gene expression (Basset, P., et al., *Nature* 348:699–704 (1990)), also cannot be excluded.

Also of interest is the observation that the level of transcription of the tag7 gene is several times lower in cells of the CSML-0 tumor than in VMR-L cells, whereas when strains of these same tumors are converted to culture, the picture changes markedly. Specifically, upon culturing these cells, the level of transcription of the tag7 gene in VMR-L cells declines, while it increases in CSML-0 cells and exceeds by several-fold the level of tag7 expression in cultured VMR-L cells. A somewhat lower level tag7 transcription was observed in cultured MT1 TC1 cells in comparison to cultured CSML-0 cells. Such a change in the level of transcription of the tag7 gene in cultured VMR-L cells may be explained by the fact that this culture is not monoclonal, and the proportion of the subpopulation of metastasizing cells in the culture therefore may be fairly low (Fidler, I. J., and Hart, I. R., *Science* 217:998–1001 (1982); Senin, V. M., *Vestn. Akad. Med. Nauk. SSSR* 0(5):85–91 (1984)). The heterogeneity of a culture CSML-0 cells, on the other hand, has been established by D. A. Kamer (personal communication). It is particularly interesting to note that the transcription of the tag7 gene was observed in cultures of cells of tumors which are of epithelial origin and have only low (5–10%) metastatic potential. However, of the 13 cell lines with varied metastatic properties that were investigated, only in cells of the VMR-L line did the transcription of the tag7 gene correlate with the marked metastatic potential of this tumor.

During the last decade a number of TNF-related cytokines have been identified and cloned. A proteolytically released form of TNF-α is a well-known soluble cytokine. In addition, the soluble form of the Fas ligand has been reported to be produced by activated peripheral T lymphocytes (Tanaka, M., et al., *EMBO J.* 14:1129–1135 (1995)) and a murine thymoma cell line was shown to secrete soluble CD40 ligand (Armitage, G., et al., *Eur. J. Immunol.* 22:2071–2076 (1992)). Due to its structural similarities with other TNF-related cytokines, tag7 may be a new member of this growing family.

The chromosome location of tag7 offers a possible insight into the in vivo role of tag7. Cytogenetic band 7A3 has been genetically linked with lupus-like nephritis in the MRL and New Zealand hybrid models of systemic lupus erythematosus (SLE) (Morel, L., et al., *Immunity* 1:219–229 (1994); Kono, D. H., et al., *Proc. Natl. Acad. Sci. USA* 91:10168–10172 (1994)). Although SLE is unlikely to involve mutations with severe functional alterations, gene knockout experiments may provide insight into the possible role of tag7 in this pathogenic process.

The localization of tag7 RNA essentially to the lymphoid organs is intriguing considering the cytotoxic effect of the soluble protein. It is evident that the main step in regulation cascade occurs at the posttranscriptional level. Even insignificant changes in tag7 mRNA production results in changes in the overall amount of protein synthesized and its secretion. It is therefore possible that differences in signaling capacity of the soluble versus the membrane-bound form of this ligand may be involved.

One of the biological activities of tag7 known from the present studies is its involvement in the in vitro induction of apoptosis in certain cell lines. Apoptosis or the process of programed cell death is necessary for the normal development and homeostasis of an organism. Fragmentation of DNA into ~180 bp multimers is one of the changes that occurs during apoptosis.

Also of interest is the finding that VMR-0 tag7-transfected tumors grew significantly more slowly than did the parental VMR-0 tumors. A number of cytokines have been shown to be able to induce tumor rejection if produced locally by the tumor cell after gene transfer (Hock, H., et al., *Proc. Natl. Acad. Sci. USA* 90:2774–2778 (1993)). Different cytokines are known to activate heterogeneous transient tumor-suppressive mechanisms but always require CD8+ cells for complete tumor rejection. Recently, a strong antitumor effect of human LT-α in a mouse experimental model has been described (Qin, Z., and Blankenstein, T., *Cancer Res.* 55:4747–4751 (1995)). A complex immunological mechanism which involves both T cells and B cells has been implicated in tumor rejection. LT-α was shown to be less toxic to animals than TNF and at least as effective as TNF (Qin, Z., et al., *Blood* 85:2779–2785 (1995)). No toxic effects of tag7-transfected cells were observed in mice, nor was any direct cytotoxic activity of clones transfected with tag7 construct detected in the L929 cytotoxic assay. Although tag7 activity in the conditioned medium of the clones was below the detection limit, the clone which produced lower amounts of tag7 RNA grew faster in syngeneic mice. A tumor-growth inhibitory effect of locally released tag7 is most likely indirect and can be reversed by injection of anti-tag7 antibodies. This was further supported by an experiment in which tumor growth of the parental VMR-0 line and co-injected 4SX cells was monitored. Even when twice the normal amount of cells was injected the rate of tumor growth was significantly reduced. Eventually, complete tumor reduction or remission could be achieved by higher amounts of tag7 secretion.

The inhibition of tumor cell growth mediated by tag7 does not seem to involve T lymphocytes, because in the absence of T cells (e.g., in nude mice) tag7-producing cells grew more slowly than in syngeneic mice (E. V. Korobko, unpublished observations). Despite these findings, however, the involvement of other cell types in the tag7-induced antitumor response cannot be ruled out.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated nucleic acid molecule comprising a polynucleotide which encodes a polypeptide having a first amino acid sequence at least 95% identical to a reference amino acid sequence selected from the group consisting of (a) amino acids 1 to 182 of SEQ ID NO:2; and (b) amino acids 20 to 182 of SEQ ID NO:2, where in said nucleic acid molecule encodes a polypeptide which mediates apoptosis or inhibits tumor growth.

2. The nucleic acid molecule of claim 1, wherein said reference amino acid sequence is (a).

3. The nucleic acid molecule of claim 1, wherein said reference amino acid sequence is (b).

4. The nucleic acid molecule of claim 1, which encodes a polypeptide which generates antibody that specifically binds a protein consisting of amino acids 1 to 182 of SEQ ID NO:2.

5. The nucleic acid molecule of claim 1, which encodes a polypeptide which mediates apoptosis.

6. The nucleic acid molecule of claim 1, which encodes a polypeptide which inhibits tumor growth.

7. An isolated transfected host cell comprising the nucleic acid molecule of claim 1.

8. A method of producing the polypeptide encoded by the nucleic acid molecule of claim 1, said method comprising:
   (a) culturing a host cell comprising said nucleic acid molecule under conditions such that said polypeptide is expressed; and
   (b) isolating said polypeptide.

9. A vector comprising the nucleic acid molecule of claim 1.

10. The vector of claim 9, wherein said vector is an expression vector.

11. An isolated recombinant nucleic acid molecule consisting essentially of a polynucleotide encoding amino acids 145 to 160 of SEQ ID NO:2.

12. An isolated polypeptide comprising a first amino acid sequence at least 95% identical to a reference amino acid sequence consisting of (a) amino acids 1 to 182 of SEQ ID NO:2; and (b) amino acids 20 to 182 of SEQ ID NO:2, wherein said polypeptide mediates apoptosis or inhibits tumor growth.

13. The polypeptide of claim 12, wherein said reference amino acid sequence is (a).

14. The polypeptide of claim 12, wherein said first amino acid sequence is amino acids 1 to 182 of SEQ ID NO:2.

15. The polypeptide of claim 12, wherein said polypeptide generates antibody that specifically binds a protein consisting of amino acids 1 to 182 of SEQ ID NO:2.

16. The polypeptide of claim 12, wherein said polypeptide mediates apoptosis.

17. The polypeptide of claim 12, wherein said polypeptide inhibits tumor growth.

18. The polypeptide of claim 12, wherein said reference amino acid sequence is (b).

19. The polypeptide of claim 18, wherein said first amino acid sequence is amino acids 20 to 182 of SEQ ID NO:2.

20. An isolated nucleic acid molecule comprising a polynucleotide which encodes a polypeptide having a first amino acid sequence at least 95% identical to amino acids 1 to 191 of SEQ ID NO:4, wherein said nucleic acid molecule encodes a polypeptide which mediates apoptosis or inhibits tumor growth.

21. The nucleic acid molecule of claim 20, comprising a polynucleotide which encodes amino acids 1 to 191 of SEQ ID NO:4.

22. The nucleic acid molecule of claim 20, which encodes a polypeptide which generates antibody that specifically binds a protein consisting of amino acids 1 to 191 of SEQ ID NO:4.

23. The nucleic acid molecule of claim 20, which encodes a polypeptide which mediates apoptosis.

24. The nucleic acid molecule of claim 20, which encodes a polypeptide which inhibits tumor growth.

25. An isolated transfected host cell comprising the nucleic acid molecule of claim 20.

26. A method of producing the polypeptide encoded by the nucleic acid molecule of claim 20, said method comprising:
   (a) culturing a host cell comprising said nucleic acid molecule under conditions such that said polypeptide is expressed; and
   (b) isolating said polypeptide.

27. A vector comprising the nucleic acid molecule of claim 20.

28. The vector of claim 27, wherein said vector is an expression vector.

29. An isolated nucleic acid molecule comprising a polynucleotide sequence at least 95% identical to nucleotides 68 to 640 of SEQ ID NO:3, wherein said nucleic acid molecule encodes a polypeptide which mediates apoptosis or inhibits tumor growth.

30. The nucleic acid molecule of claim 29, comprising the polynucleotide sequence of nucleotides 68 to 640 of SEQ ID NO:3.

31. The nucleic acid molecule of claim 29, which encodes a polypeptide which generates antibody that specifically binds a protein consisting of amino acids 1 to 191 of SEQ ID NO:4.

32. The nucleic acid molecule of claim 29, which encodes a polypeptide which mediates apoptosis.

33. The nucleic acid molecule of claim 29, which encodes a polypeptide which inhibits tumor growth.

34. An isolated polypeptide comprising an amino acid sequence at least 95% identical to amino acids 1 to 191 of SEQ ID NO:4, wherein said polypeptide mediates apoptosis or inhibits tumor growth.

35. The polypeptide of claim 34, which generates antibody that specifically binds a protein consisting of amino acids 1 to 191 of SEQ ID NO:4.

36. The polypeptide of claim 34, which mediates apoptosis.

37. The isolated polypeptide of claim 34, which inhibits tumor growth.

38. The polypeptide of claim 34, comprising amino acids 1 to 191 of SEQ ID NO:4.

39. An isolated recombinant polypeptide consisting essentially of amino acids 145 to 160 of SEQ ID NO:2.

* * * * *

SEQUENCE LISTING

```
<160> NUMBER OF SEQ ID NOS: 24

<210> SEQ ID NO 1
<211> LENGTH: 549
<212> TYPE: DNA
<213> ORGANISM: Artificial Sequence
<220> FEATURE:
<221> NAME/KEY: CDS
<222> LOCATION: (1)..(549)
<223> OTHER INFORMATION: Description of Artificial Sequence: tag7 cDNA

<400> SEQUENCE: 1 atg ttg ttt gcc tgt gct ctc ctt gcc ctc ctg ggt ctg gca acc tcc      48
```

```
Met Leu Phe Ala Cys Ala Leu Leu Ala Leu Leu Gly Leu Ala Thr Ser
  1               5                  10                 15 tgc agt ttc atc gtg ccc cgc agt gag tgg agg gcc ctg cca tcc gag    96
Cys Ser Phe Ile Val Pro Arg Ser Glu Trp Arg Ala Leu Pro Ser Glu
             20                  25                  30 tgc tct agc cgc ctg ggg cac cca gtt cgc tac gtg gtg atc tca cac   144
Cys Ser Ser Arg Leu Gly His Pro Val Arg Tyr Val Val Ile Ser His
         35                  40                  45 aca gcc ggc agc ttc tgc aac agc ccg gac tcc tgt gaa cag cag gcc   192
Thr Ala Gly Ser Phe Cys Asn Ser Pro Asp Ser Cys Glu Gln Gln Ala
     50                  55                  60 cgc aat gtg cag cat tac cac aag aat gag ctg ggc tgg tgc gat gta   240
Arg Asn Val Gln His Tyr His Lys Asn Glu Leu Gly Trp Cys Asp Val
 65                  70                  75                  80 gcc tac aac ttc ctt att gga gag gac ggt cat gtc tat gaa ggc cga   288
Ala Tyr Asn Phe Leu Ile Gly Glu Asp Gly His Val Tyr Glu Gly Arg
                 85                  90                  95 ggc tgg aac atc aag ggt gac cac aca ggg ccc atc tgg aat ccc atg   336
Gly Trp Asn Ile Lys Gly Asp His Thr Gly Pro Ile Trp Asn Pro Met
             100                 105                 110 tct att ggc atc acc ttc atg ggg aac ttc atg gac cgg gta ccc gca   384
Ser Ile Gly Ile Thr Phe Met Gly Asn Phe Met Asp Arg Val Pro Ala
         115                 120                 125 aag cgg gcc ctc cgt gct gcc cta aat ctt ctg gaa tgt ggg gtg tct   432
Lys Arg Ala Leu Arg Ala Ala Leu Asn Leu Leu Glu Cys Gly Val Ser
     130                 135                 140 cgg ggc ttc ctg aga tcc aac tat gaa gtc aaa gga cac cgg gat gtg   480
Arg Gly Phe Leu Arg Ser Asn Tyr Glu Val Lys Gly His Arg Asp Val
145                 150                 155                 160 caa agc act ctc tct cca ggt gac caa ctc tat cag gtc atc caa agc   528
Gln Ser Thr Leu Ser Pro Gly Asp Gln Leu Tyr Gln Val Ile Gln Ser
                 165                 170                 175 tgg gaa cac tac cga gag tga                                       549
Trp Glu His Tyr Arg Glu
             180
```

<210> SEQ ID NO 2
<211> LENGTH: 182
<212> TYPE: PRT
<213> ORGANISM: Artificial Sequence
<220> FEATURE:
<223> OTHER INFORMATION: Description of Artificial Sequence: tag7 cDNA

<400> SEQUENCE: 2

```
Met Leu Phe Ala Cys Ala Leu Leu Ala Leu Leu Gly Leu Ala Thr Ser
  1               5                  10                 15

Cys Ser Phe Ile Val Pro Arg Ser Glu Trp Arg Ala Leu Pro Ser Glu
             20                  25                  30

Cys Ser Ser Arg Leu Gly His Pro Val Arg Tyr Val Val Ile Ser His
         35                  40                  45

Thr Ala Gly Ser Phe Cys Asn Ser Pro Asp Ser Cys Glu Gln Gln Ala
     50                  55                  60

Arg Asn Val Gln His Tyr His Lys Asn Glu Leu Gly Trp Cys Asp Val
 65                  70                  75                  80

Ala Tyr Asn Phe Leu Ile Gly Glu Asp Gly His Val Tyr Glu Gly Arg
                 85                  90                  95

Gly Trp Asn Ile Lys Gly Asp His Thr Gly Pro Ile Trp Asn Pro Met
             100                 105                 110

Ser Ile Gly Ile Thr Phe Met Gly Asn Phe Met Asp Arg Val Pro Ala
```

```
                    115                 120                 125
Lys Arg Ala Leu Arg Ala Ala Leu Asn Leu Leu Glu Cys Gly Val Ser
    130                 135                 140

Arg Gly Phe Leu Arg Ser Asn Tyr Glu Val Lys Gly His Arg Asp Val
145                 150                 155                 160

Gln Ser Thr Leu Ser Pro Gly Asp Gln Leu Tyr Gln Val Ile Gln Ser
                165                 170                 175

Trp Glu His Tyr Arg Glu
            180

<210> SEQ ID NO 3
<211> LENGTH: 718
<212> TYPE: DNA
<213> ORGANISM: Homo sapiens
<220> FEATURE:
<221> NAME/KEY: 5'UTR
<222> LOCATION: (1)..(67)
<221> NAME/KEY: CDS
<222> LOCATION: (68)..(643)
<221> NAME/KEY: 3'UTR
<222> LOCATION: (644)..(718)
<221> NAME/KEY: polyA_site
<222> LOCATION: (712)..(714)

<400> SEQUENCE: 3
ctgagttact gggcccagag gctgggcccc tggacatgta cctgcagcca ctatgtcccg     60 ccgctct atg ctg ctt gcc tgg gct ctc ccc agc ctc ctt cga ctc gga     109
        Met Leu Leu Ala Trp Ala Leu Pro Ser Leu Leu Arg Leu Gly
          1               5                  10 gcg gct cag gag aca gaa gac ccg gcc tgc tgc agc ccc ata gtg ccc     157
Ala Ala Gln Glu Thr Glu Asp Pro Ala Cys Cys Ser Pro Ile Val Pro
 15              20                  25                  30 cgg aac gag tgg aag gcc ctg gca tca gag tgc gcc cag cac ctg agc     205
Arg Asn Glu Trp Lys Ala Leu Ala Ser Glu Cys Ala Gln His Leu Ser
                 35                  40                  45 ctg ccc tta cgc tat gtg gtg gta tcg cac acg gcg ggc agc agc tgc     253
Leu Pro Leu Arg Tyr Val Val Val Ser His Thr Ala Gly Ser Ser Cys
             50                  55                  60 aac acc ccc gcc tcg tgc cag cag cag gcc cgg aat gtg cag cac tac     301
Asn Thr Pro Ala Ser Cys Gln Gln Gln Ala Arg Asn Val Gln His Tyr
         65                  70                  75 cac atg aag aca ctg ggc tgg tgc gac gtg ggc tac aac ttc ctg att     349
His Met Lys Thr Leu Gly Trp Cys Asp Val Gly Tyr Asn Phe Leu Ile
     80                  85                  90 gga gaa gac ggg ctc gta tac gag ggc cgt ggc tgg aac ttc acg ggt     397
Gly Glu Asp Gly Leu Val Tyr Glu Gly Arg Gly Trp Asn Phe Thr Gly
 95                 100                 105                 110 gcc cac tca ggt cac tta tgg aac ccc atg tcc att ggc atc agc ttc     445
Ala His Ser Gly His Leu Trp Asn Pro Met Ser Ile Gly Ile Ser Phe
                115                 120                 125 atg ggc aac tac atg gat cgg gtg ccc aca ccc cag gcc atc cgg gca     493
Met Gly Asn Tyr Met Asp Arg Val Pro Thr Pro Gln Ala Ile Arg Ala
            130                 135                 140 gcc cag ggt cta ctg gcc tgc ggt gtg gct cag gga gcc ctg agg tcc     541
Ala Gln Gly Leu Leu Ala Cys Gly Val Ala Gln Gly Ala Leu Arg Ser
        145                 150                 155 aac tat gtg ctc aaa gga cac cgg gat gtg cag cgt aca ctc tct cca     589
Asn Tyr Val Leu Lys Gly His Arg Asp Val Gln Arg Thr Leu Ser Pro
    160                 165                 170 ggc aac cag ctc tac cac ctc atc cag aat tgg cca cac tac cgc tcc     637
Gly Asn Gln Leu Tyr His Leu Ile Gln Asn Trp Pro His Tyr Arg Ser
```

-continued

```
          175                 180                 185                 190
ccc tga ggccctgctg atccgcaccc cattcctccc ctcccatggc caaaaacccc          693
Pro actgtctcct tctccaataa agatg                                              718
```

<210> SEQ ID NO 4
<211> LENGTH: 191
<212> TYPE: PRT
<213> ORGANISM: Homo sapiens

<400> SEQUENCE: 4

```
Met Leu Leu Ala Trp Ala Leu Pro Ser Leu Leu Arg Leu Gly Ala Ala
 1               5                  10                  15

Gln Glu Thr Glu Asp Pro Ala Cys Cys Ser Pro Ile Val Pro Arg Asn
            20                  25                  30

Glu Trp Lys Ala Leu Ala Ser Glu Cys Ala Gln His Leu Ser Leu Pro
        35                  40                  45

Leu Arg Tyr Val Val Ser His Thr Ala Gly Ser Ser Cys Asn Thr
    50                  55                  60

Pro Ala Ser Cys Gln Gln Gln Ala Arg Asn Val Gln His Tyr His Met
65                  70                  75                  80

Lys Thr Leu Gly Trp Cys Asp Val Gly Tyr Asn Phe Leu Ile Gly Glu
                85                  90                  95

Asp Gly Leu Val Tyr Glu Gly Arg Gly Trp Asn Phe Thr Gly Ala His
            100                 105                 110

Ser Gly His Leu Trp Asn Pro Met Ser Ile Gly Ile Ser Phe Met Gly
        115                 120                 125

Asn Tyr Met Asp Arg Val Pro Thr Pro Gln Ala Ile Arg Ala Ala Gln
    130                 135                 140

Gly Leu Leu Ala Cys Gly Val Ala Gln Gly Ala Leu Arg Ser Asn Tyr
145                 150                 155                 160

Val Leu Lys Gly His Arg Asp Val Gln Arg Thr Leu Ser Pro Gly Asn
                165                 170                 175

Gln Leu Tyr His Leu Ile Gln Asn Trp Pro His Tyr Arg Ser Pro
            180                 185                 190
```

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: DNA Primer

<400> SEQUENCE: 5

```
tttttttttt ttac                                                          14
```

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: DNA Primer

<400> SEQUENCE: 6

```
aatcgggctg                                                               10
```

<210> SEQ ID NO 7
<211> LENGTH: 10
<212> TYPE: DNA

```
<213> ORGANISM: Artificial Sequence
<220> FEATURE:
<223> OTHER INFORMATION: Description of Artificial Sequence: DNA Primer

<400> SEQUENCE: 7
agtcagccac                                                            10

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: DNA Primer

<400> SEQUENCE: 8
gaaagggcct cgtgatac                                                   18

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 9
cagggccctc cactcacttg cataggcatt tgtagc                               36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 10
gctacaaatg cctatgcaag tgagtggagg gccctg                               36

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: DNA Primer

<400> SEQUENCE: 11
ggccgctagc ctgcagttat cactctcggt agtgttccca g                         41

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: DNA Primer

<400> SEQUENCE: 12
ggcggatccg agtggagggc cctgccatcc                                      30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: DNA Primer

<400> SEQUENCE: 13
ggcgaattct tatcactctc ggtagtgttc                                      30
```

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 14
ggccagatct cgtccagcat gttgtttgcc tgtgct                               36

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: DNA Primer

<400> SEQUENCE: 15
ggcaccaaaa tcaacgggac                                                 20

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: DNA Primer

<400> SEQUENCE: 16
cagggccctc cactcacatc gtgcacctgg g                                    31

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: DNA Primer

<400> SEQUENCE: 17
cccaggtgca cgatgtgagt ggagggccct g                                    31

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: DNA Primer

<400> SEQUENCE: 18
ggccgctagc ctgcagttat cactctcggt agtgttccca g                         41

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 19
ggccaagctt ccaccatgtc ccgccgctct atgctg                               36

<210> SEQ ID NO 20
<211> LENGTH: 34
<212> TYPE: DNA
<213> ORGANISM: Artificial Sequence
<220> FEATURE:

-continued

```
<223> OTHER INFORMATION: Description of Artificial Sequence: DNA Primer

<400> SEQUENCE: 20
ggccgaattc ttatcagggg gagcggtagt gtgg                                34

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: mutag7
      peptide

<400> SEQUENCE: 21

Arg Ser Glu Trp Arg Ala Leu Pro Ser Glu Cys Ser Ser Arg Leu Gly
 1               5                  10                  15

His Pro Tyr

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: mutag7
      peptide

<400> SEQUENCE: 22

Gly Glu Asp Gly His Val Tyr Glu Gly Arg Gly Trp Asn Ile Lys Gly
 1               5                  10                  15

Asp His Thr Gly Cys Tyr
            20

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: hutag7
      peptide

<400> SEQUENCE: 23

Ala Gln Glu Thr Glu Asp Pro Ala Cys Cys Ser Pro Ile Val Pro Arg
 1               5                  10                  15

Asn Glu Trp Lys Ala Leu Ala Ser Glu Tyr
            20                  25

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: hutag7
      peptide

<400> SEQUENCE: 24

Gly Glu Asp Gly Leu Val Tyr Glu Gly Arg Gly Trp Asn Phe Thr Gly
 1               5                  10                  15

Cys Tyr
```